United States Patent
Kasdan et al.

(10) Patent No.: US 9,746,462 B2
(45) Date of Patent: Aug. 29, 2017

(54) SYSTEMS AND METHODS FOR DETECTING A BIOLOGICAL CONDITION

(71) Applicant: LEUKODX LTD., Jerusalem (IL)

(72) Inventors: Harvey Lee Kasdan, Jerusalem (IL); Julien Meissonnier, Jerusalem (IL); Yoav Zuta, Jerusalem (IL); Micha Rosen, Jerusalem (IL); Yael Himmel, Jerusalem (IL); Yehoshua Broder, Jerusalem (IL); Bruce Davis, Jerusalem (IL); Bruce Goldman, Jerusalem (IL); Boaz Giron, Jerusalem (IL); Zion Botesazan, Jerusalem (IL); Ellezer Blasberg, Jerusalem (IL); Ilan Semmel, Jerusalem (IL); Jacques Aschkenasy, Jerusalem (IL)

(73) Assignee: Leukodx Ltd., Jerusalem (IL)

( * ) Notice: Subject to any disclaimer, the term of this patent is extended or adjusted under 35 U.S.C. 154(b) by 0 days.

(21) Appl. No.: 14/646,603

(22) PCT Filed: Dec. 17, 2013

(86) PCT No.: PCT/IL2013/000093
§ 371 (c)(1),
(2) Date: May 21, 2015

(87) PCT Pub. No.: WO2014/097287
PCT Pub. Date: Jun. 26, 2014

(65) Prior Publication Data
US 2015/0293095 A1    Oct. 15, 2015

Related U.S. Application Data

(63) Continuation of application No. 13/716,246, filed on Dec. 17, 2012, now abandoned.
(Continued)

(51) Int. Cl.
*G01N 33/53* (2006.01)
*G01N 33/68* (2006.01)
(Continued)

(52) U.S. Cl.
CPC .......... *G01N 33/5302* (2013.01); *B01L 3/502* (2013.01); *B01L 3/5027* (2013.01);
(Continued)

(58) Field of Classification Search
CPC ............... G01N 33/5302; G01N 33/68; G01N 33/5091; G01N 33/569; G01N 33/56972;
(Continued)

(56) References Cited

U.S. PATENT DOCUMENTS 4,684,252 A * 8/1987 Makiguchi ........... G01N 21/253
356/328
5,408,314 A * 4/1995 Perry ........................ G01J 1/44
348/E5.081

(Continued)

FOREIGN PATENT DOCUMENTS

CN      101848765 A    9/2010
WO   2006055816 A2    5/2006
(Continued)

OTHER PUBLICATIONS

Written Opinion of the International Searching Authority for PCT/IL2013/000093.
(Continued)

*Primary Examiner* — Todd J Scherbel
*Assistant Examiner* — Guy Townsend
(74) *Attorney, Agent, or Firm* — Eva Leah Taksel

(57) ABSTRACT

The present invention provides self-contained systems, apparatus and methods for determining a chemical state, the system includes a stationary cartridge for performing the assay therein, the cartridge adapted to house at least one
(Continued)

reagent adapted to react with a sample; and at least one reporter functionality adapted to report a reaction of the at least one reagent with the sample to report a result of the assay, a mechanical controller including a first urging means adapted to apply a force externally onto the cartridge to release the at least one reagent; and at least one second urging means adapted to apply a removable force to induce fluidic movement in a first direction in the cartridge and upon removal of the force causing fluidic movement in an opposite direction to the first direction, an optical reader adapted to detect the reaction and a processor adapted to receive data from the optical reader and to process the data to determine said chemical state.

11 Claims, 52 Drawing Sheets

Related U.S. Application Data

(60) Provisional application No. 61/737,854, filed on Dec. 17, 2012, provisional application No. 61/737,856, filed on Dec. 17, 2012.

(51) Int. Cl.
*G01N 33/50* (2006.01)
*B01L 3/00* (2006.01)
*G01N 33/543* (2006.01)
*G01N 33/569* (2006.01)
*G01N 33/58* (2006.01)

(52) U.S. Cl.
CPC ..... *B01L 3/50273* (2013.01); *B01L 3/502715* (2013.01); *G01N 33/5091* (2013.01); *G01N 33/54386* (2013.01); *G01N 33/569* (2013.01); *G01N 33/56972* (2013.01); *G01N 33/582* (2013.01); *G01N 33/68* (2013.01); *G01N 33/6872* (2013.01); *B01L 2200/025* (2013.01); *B01L 2200/10* (2013.01); *B01L 2300/041* (2013.01); *B01L 2300/0654* (2013.01); *B01L 2300/0816* (2013.01); *B01L 2300/0867* (2013.01); *B01L 2300/0877* (2013.01); *B01L 2300/0883* (2013.01); *B01L 2300/123* (2013.01); *B01L 2300/18* (2013.01); *B01L 2400/0406* (2013.01); *B01L 2400/0481* (2013.01); *G01N 2333/70535* (2013.01); *G01N 2333/70596* (2013.01); *G01N 2800/26* (2013.01)

(58) Field of Classification Search
CPC ... G01N 33/502; B01L 3/50273; B01L 3/502; B01L 3/5027; B01L 3/502715
See application file for complete search history.

(56) References Cited

U.S. PATENT DOCUMENTS

| | | | |
|---|---|---|---|
| 6,168,948 B1 | 1/2001 | Anderson | |
| 6,551,841 B1* | 4/2003 | Wilding | B01J 19/0093 |
| | | | 422/400 |
| 2002/0113961 A1* | 8/2002 | Gamble | G01J 3/44 |
| | | | 356/301 |
| 2003/0153844 A1* | 8/2003 | Smith | A61B 10/0051 |
| | | | 600/573 |
| 2003/0170881 A1* | 9/2003 | Davis | B01L 3/502723 |
| | | | 435/287.2 |
| 2003/0175990 A1 | 9/2003 | Hayenga | |
| 2003/0194752 A1 | 10/2003 | Anderson | |
| 2003/0233827 A1 | 12/2003 | Kuo et al. | |
| 2004/0053290 A1* | 3/2004 | Terbrueggen | B01F 11/0071 |
| | | | 435/6.11 |
| 2005/0118723 A1* | 6/2005 | Padmanabhan | G01N 15/1404 |
| | | | 436/164 |
| 2005/0148093 A1 | 7/2005 | Chien | |
| 2005/0154268 A1* | 7/2005 | Hwang | A61B 5/14532 |
| | | | 600/316 |
| 2005/0221281 A1 | 10/2005 | Ho | |
| 2005/0255600 A1 | 11/2005 | Padmanabhan | |
| 2006/0134712 A1 | 6/2006 | Stromgren | |
| 2006/0269446 A1* | 11/2006 | Gilbert | B01L 3/502761 |
| | | | 422/400 |
| 2007/0281311 A1* | 12/2007 | Roth | G01N 33/54333 |
| | | | 435/6.11 |
| 2008/0176253 A1 | 7/2008 | Christodoulides | |
| 2012/0164627 A1 | 6/2012 | Battrell | |
| 2012/0177543 A1 | 7/2012 | Battrell | |
| 2013/0065269 A1* | 3/2013 | Nitta | G01N 21/274 |
| | | | 435/34 |
| 2013/0102087 A1 | 4/2013 | Kasdan | |
| 2013/0323825 A1* | 12/2013 | Sekino | G01N 21/6486 |
| | | | 435/287.2 |

FOREIGN PATENT DOCUMENTS

| | | |
|---|---|---|
| WO | 2011094577 A2 | 8/2011 |
| WO | 2011128893 A2 | 10/2011 |
| WO | 2012120506 A2 | 9/2012 |
| WO | 2012170711 A1 | 12/2012 |

OTHER PUBLICATIONS

International Search Report for PCT/IL2013/000093.
European patent Office Office Action Dated Jun. 2, 2017 for corresponding application (13 865 771.3-1554).

* cited by examiner

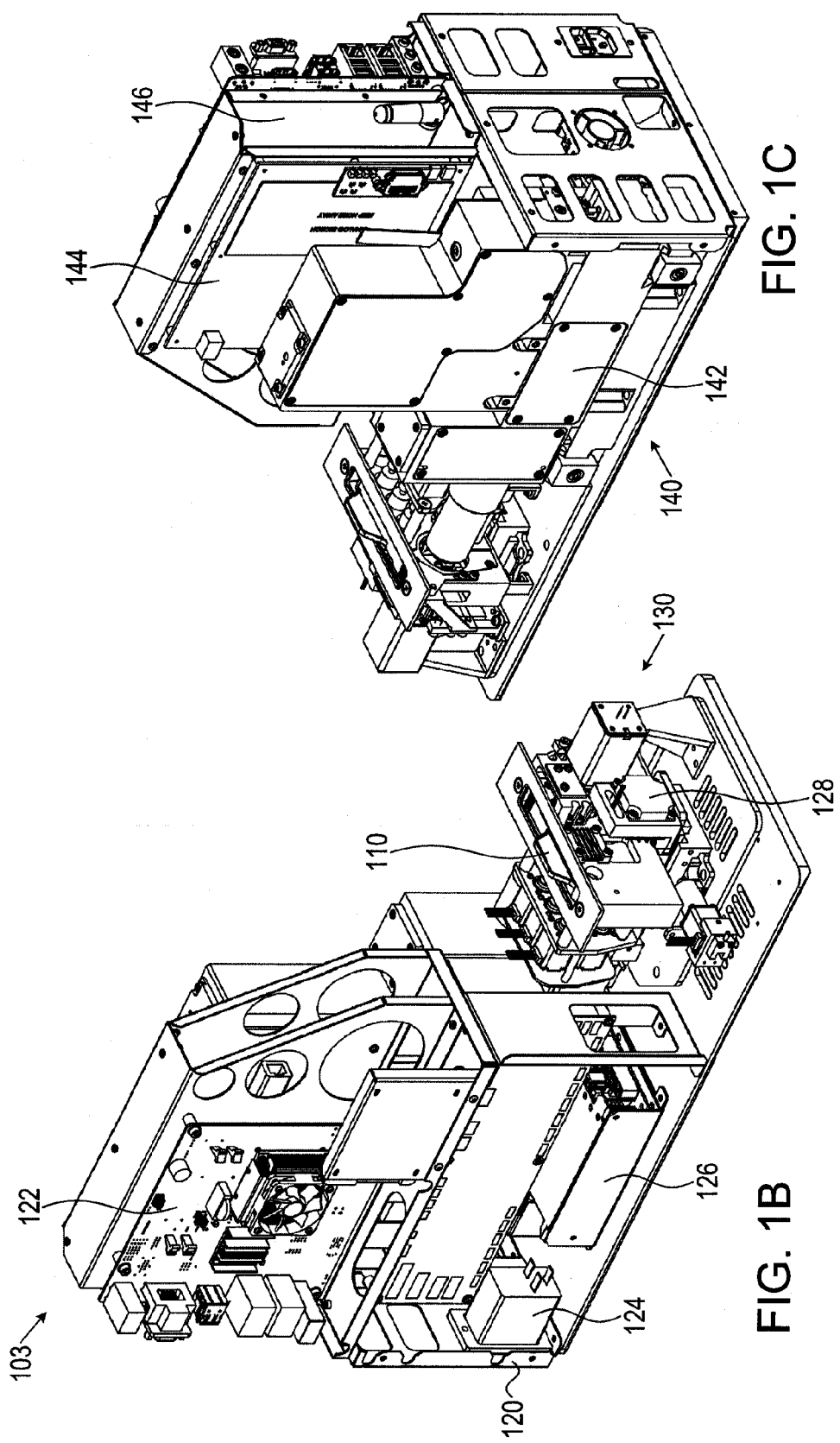

The setup for RGB lasters (Grayscale)

Solving for the fluor decomposition of the observed signal (pulse)

function [ x ] = FluorSolver( A, b )

```
%FluorSolver Solve for fluorophore composition of an observed 8-channel
%response
% Detailed explanation:
% This routine finds x, the solution of the equation Ax = b
% A is a matrix with 8 rows whose columns are normalized fluor
%         responses, i.e. the sum of the 8-elements in each column is 1.
% b is a column vector with 8-rows or a matrix of such column vectors
%         that is the observed response
% x is a column vector with the number of rows equal to the number of
%         columns A (number of possible fluors) if b is a column vector. If
%         b is a matrix, x is a matrix with with the number of rows equal to
%         the number of columns A and the number of columns equal to the
%         number of columns of b. Each column of b is the weighting of the
%         fluors in the columns of A that best match the observed fluor response.
% For example using a 6-element fluor representation
%      A' = [1 10 5 0 0 0;
%            1 5 10 4 0 0;
%            0 0 3 10 5 0;
%            0 0 10 7 3 2]
%A' =
%   1   10   5   0   0   0
%   1    5  10   4   0   0
%   0    0   3  10   5   0
%   0    0  10   7   3   2
%      b' = [1 11 5 0 0 0;
%            2 15 15 4 0 0;
%            2 20 13 10 5 0]
%b' =
%   1   11   5   0   0   0
%   2   15   15   4   0   0
%   2   20   13  10   5   0
%[ x ] = FluorSolver( A, b )
%x =
%   1.1191   1.0000   2.0000
%  -0.0416   1.0000   0.0000
%   0.0301   0.0000   1.0000
%  -0.0253  -0.0000  -0.0000
%
x = A\b;
end
```

FIG. 21A

Current fluor signature matrix A

| F488 | Noise | PE488 | SFR488 |
|---|---|---|---|
| 0.269784 | 0.125 | 0.005805 | 0 |
| 0.471087 | 0.125 | 0.015633 | 0 |
| 0.158544 | 0.125 | 0.318742 | 0 |
| 0.062158 | 0.125 | 0.396312 | 0 |
| 0.021845 | 0.125 | 0.156353 | 0 |
| 0.006157 | 0.125 | 0.072972 | 0 |
| 0.006048 | 0.125 | 0.024215 | 0.426647 |
| 0.004377 | 0.125 | 0.009968 | 0.573353 |

FIG. 21B

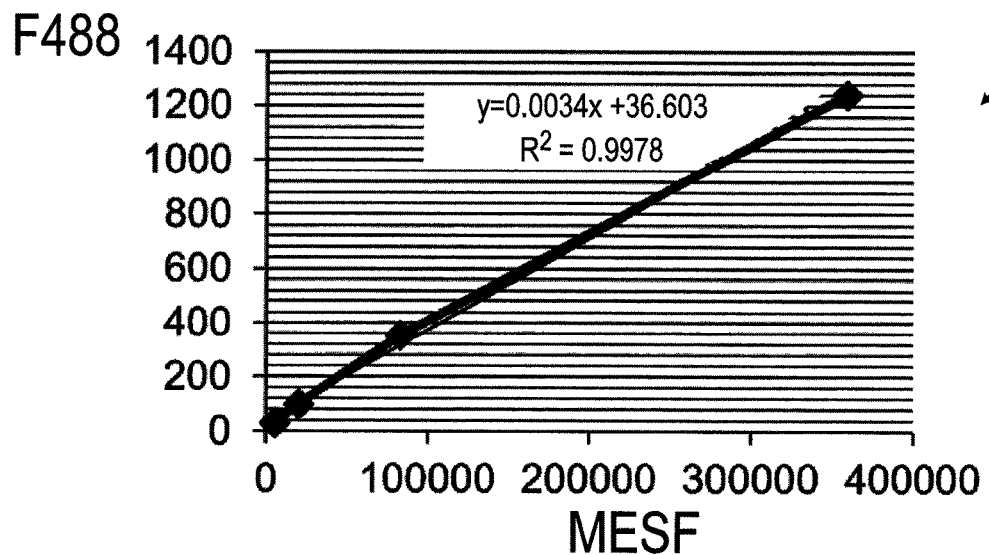
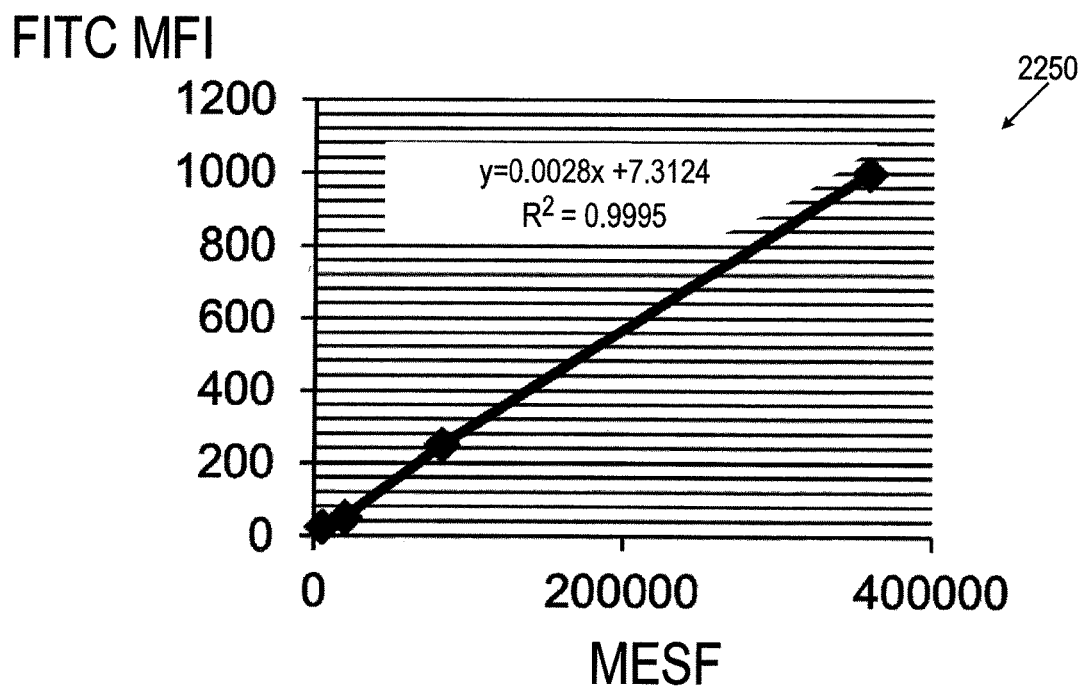
FIG. 22B

LINEAR FIT
F488N=463.95252+0.0118577 BeadMESF

SUMMARY OF FIT
RSquare                       0.986887
RSquare Adj                   0.980331
Root Mean Square Error        736.7946
Mean of Response              3944.267
Observation (or Sum Wgts)     4

ANALYSIS OF VARIANCE
| SOURCE | DF | SUM OF SQRS | MEAN SQR | F RATIO |
|---|---|---|---|---|
| Model | 1 | 81714622 | 81714622 | 150.5244 |
| Error | 2 | 1085733 | 542866.31 | Prob>F |
| C.Total | 3 | 82800355 | | 0.0066 |

PARAMETER ESTIMATES
| TERM | ESTIMATE | STD ERROR | t RATIO | PROB>|t| |
|---|---|---|---|---|
| Intercept | 463.95252 | 464.9579 | 1.00 | 0.4235 |
| BeadMESF | 0.0118577 | 0.00966 | 12.27 | 0.0066 |

LINEAR FIT
F488N=372.07609+0.0143173 BeadMESF

SUMMARY OF FIT
RSquare                    0.986889
RSquare Adj                0.995334
Root Mean Square Error     431.117
Mean of Response           4574.303
Observation (or Sum Wgts)  4

ANALYSIS OF VARIANCE

| SOURCE  | DF | SUM OF SQRS | MEAN SQR  | F RATIO  |
|---------|----|-------------|-----------|----------|
| Model   | 1  | 119130179   | 119130179 | 640.9608 |
| Error   | 2  | 371724      | 195861.87 | Prob>F   |
| C.Total | 3  | 119501903   |           | 0.0016   |

PARAMETER ESTIMATES

| TERM      | ESTIMATE  | STD ERROR | t RATIO | PROB>[t] |
|-----------|-----------|-----------|---------|----------|
| Intercept | 372.07609 | 272.0585  | 1.37    | 0.3048   |
| BeadMESF  | 0.0143173 | 0.000566  | 25.32   | 0.0016   |

| Waveband | F488 | Noise | PE488 | SFR488 | PEAF488 |
|---|---|---|---|---|---|
| 1: 500-524 | 0.269784 | 0.125 | 0.005805 | 0 | 0.006927 |
| 2: 525-549 | 0.471087 | 0.125 | 0.015633 | 0 | 0.016996 |
| 3: 550-574 | 0.158544 | 0.125 | 0.318742 | 0 | 0.038335 |
| 4: 575-599 | 0.062158 | 0.125 | 0.396312 | 0 | 0.040674 |
| 5: 600-624 | 0.021845 | 0.125 | 0.156353 | 0 | 0.364123 |
| 6: 625-649 | 0.006157 | 0.125 | 0.072972 | 0 | 0.340389 |
| 7: 650-674 | 0.006048 | 0.125 | 0.024215 | 0.426647 | 0.127784 |
| 8: 675-700 | 0.004377 | 0.125 | 0.009968 | 0.573353 | 0.064773 |

| Type No. | Anode Type | | Effective Area per Channel (mm) | Channel Pitch (mm) | Dynode Structure / No. of Stages | Weight (g) | Insulation Cover Material |
|---|---|---|---|---|---|---|---|
| H9530 SERIES | 8-Channel IUi near Array | 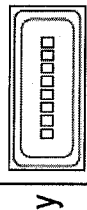 | 2.0x2.5 | 2.8 | MC/12 | 25.5 | P.O.M |
| H105158 SERIES | 16-Channel Linear Anay |  | 0.8 x 16 | 1 | MC110 | 49.0 | P.O.M |
| H7260 SERIES | 32-Channel Linear Anay |  | 0.8 x7 | 1 | MC/12 | 62.0 | P.O.M |
FIG. 28

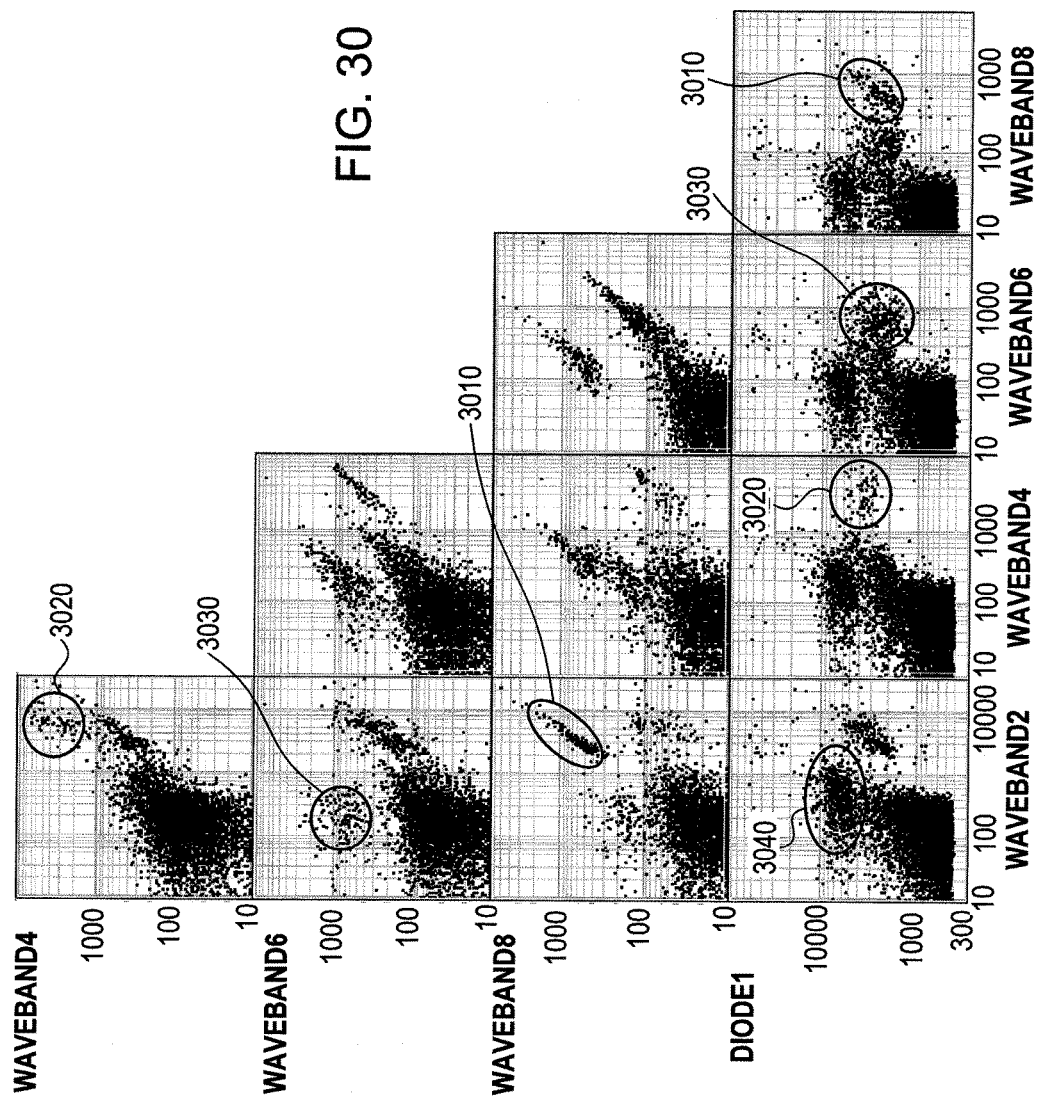

SYSTEMS AND METHODS FOR DETECTING A BIOLOGICAL CONDITION

CROSS REFERENCE TO RELATED APPLICATIONS

The present invention is a national phase of, and claims priority from PCT Application No. PCT/IL2013/000093, filed on Dec. 17, 2013, which claims priority from U.S. provisional patent application 61/737,854, to Kasdan et al, filed on Dec. 17, 2012, from U.S. provisional patent application 61/737,856, to Kasdan et al., filed on Dec. 17, 2012 and from U.S. patent application Ser. No. 13/716,246 filed on Dec. 17, 2012, incorporated herein by reference.

FIELD OF THE INVENTION

The present invention relates generally to apparatus and methods for detecting a biological condition, and more specifically to methods and apparatus for detecting a biological condition in small fluid samples.

BACKGROUND OF THE INVENTION

There are numerous medical conditions which are hard to diagnose. Often diagnosis by a physician is based on the physician's observation of combinations of symptoms in a patient. This sometimes leads to misdiagnosis. Furthermore, the patient's response to a treatment, whether drug or other modality is often followed up by physician's observation.

Many laboratory tests are performed in the diagnostic arena on a bodily specimen or fluid to determine a biological condition in a patient. However, these tests are performed off-line in diagnostic laboratories. Often, the laboratory services are only provided during a single 8-hour shift during the day and tend to be labor intensive. Some prior art publications in the field include, inter alia, U.S. Pat. No. 8,116,984, US2006215155 and US2012187117.

Despite the inventions mentioned hereinabove, there still remains an unmet need to provide improved apparatus and methods for detecting and diagnosing biological conditions in a patient.

SUMMARY OF THE INVENTION

It is an object of some aspects of the present invention to provide improved apparatus and methods for detecting and diagnosing biological conditions in a patient.

In some embodiments of the present invention, improved methods, apparatus and kits are provided for detecting and diagnosing a biological condition in a patient.

In other embodiments of the present invention, a method and kit is described for providing rapid detection of biological moieties in a sample from a patient.

In further embodiments of the present invention, a method and kit is disclosed for providing detection of biological moieties in a small fluid sample from a patient.

There is thus provided according to an embodiment of the present invention, a self-contained system for performing an assay for determining a chemical state, the system including;
 a) a stationary cartridge for performing the assay therein, the cartridge adapted to house at least one reagent adapted to react with a sample; and at least one reporter functionality adapted to report a reaction of the at least one reagent with the sample to report a result of the assay;
 b) a mechanical controller including;
  i. a first urging means adapted to apply a force externally onto the cartridge to release the at least one reagent;
  ii. at least one second urging means adapted to apply a removable force to induce fluidic movement in a first direction in the cartridge and upon removal of the force causing fluidic movement in an opposite direction to the first direction;
 c) an optical reader adapted to detect the reaction; and
 d) a processor adapted to receive data from the optical reader and to process the data to determine the chemical state.

Additionally, according to an embodiment of the present invention, the cartridge further includes an alignment means adapted to align a reading channel on the cartridge for a detection of the least one reporter functionality.

Furthermore, according to an embodiment of the present invention, the cartridge further comprises a plurality of fluidic open channels, all the channels in liquid communication with each other.

Moreover, according to an embodiment of the present invention, the cartridge is adapted to be sealed after receiving a fluid specimen and to pass a predetermined quantity of the sample through at least part of the plurality of fluidic open channels.

Further, according to an embodiment of the present invention, the cartridge further includes at least one inflatable deformable elastic chamber adapted to apply at least one of a negative pressure and a positive pressure in the fluidic channels.

Additionally, according to an embodiment of the present invention, the at least one deformable elastic chamber is adapted to further contact the at least one reagent stored in a sealed on-board storage chamber with a predetermined quantity of the sample in a reaction chamber to induce the reaction.

Further, according to an embodiment of the present invention, the a first urging means is disposed proximal to the on-board storage chamber such that upon movement is adapted to break a frangible seal on the storage chamber.

Yet further, according to an embodiment of the present invention, the alignment means adapted to align with a reading channel on the cartridge for a detection of a reaction in the predetermined quantity of the sample.

Additionally, according to an embodiment of the present invention, some of the plurality of fluidic open channels is of a cross-section of 0.1 to 2 mm$^2$.

Notably, according to an embodiment of the present invention, the predetermined quantity is of a volume of 10 to 500 microliters.

Furthermore, according to an embodiment of the present invention, the cartridge is adapted to contact a plurality of on-board reagents with the at least one of the sample and a reaction product.

In some cases, according to an embodiment of the present invention, the cartridge is adapted to induce cascaded sequential reactions of the plurality of on-board reagents, with the at least one of the sample and the reaction product.

Additionally, according to an embodiment of the present invention, the cartridge includes at least one reaction chamber of a volume of 200 to 10000 microliters.

Furthermore, according to an embodiment of the present invention, the system further includes a temperature control device external to the cartridge, the device being adapted to control a temperature of the reaction.

Additionally, according to an embodiment of the present invention, the cartridge has a shelf-life of 6 to 24 months.

Importantly, according to an embodiment of the present invention, the cartridge is valveless.

Notably, according to an embodiment of the present invention, the assay is a flow cytometric assay.

Additionally, according to an embodiment of the present invention, the chemical state is a biochemical state.

Furthermore, according to an embodiment of the present invention, the biochemical state is indicative of a biological condition.

Additionally, according to an embodiment of the present invention, the sample is a biological sample.

In some cases, according to an embodiment of the present invention, the biological sample is a bodily sample.

Moreover, according to an embodiment of the present invention, the bodily sample is selected from a the group consisting of blood, serum, plasma, urine, saliva, cerebrospinal fluid (CSF), serous fluid, peritoneal fluid and synovial fluid blood, urine, plasma, serum and saliva.

Additionally, according to an embodiment of the present invention, the cartridge is valveless.

Further, according to an embodiment of the present invention, the cartridge is a disposable microfluidics cartridge.

Yet further, according to an embodiment of the present invention, the sample is introduced to the cartridge via capillary action.

Additionally, according to an embodiment of the present invention, the cartridge includes at least one of the following elements;
  i. a reservoir;
  ii. a pump;
  iii. a conduit;
  iv. a miniaturized flow cell;
  v. a transport channel;
  vi. a reading channel;
  vii. a microfluidic element;
  viii. a compressed gas holding element;
  ix. a compressed gas releasing element;
  x. a nozzle element;
  xi. a mixing element;
  xii. a bellows element.
  xiii. software adapted to activate the elements according to a specific sequence; and
  xiv. hardware to activate the elements according to a specific sequence.

Additionally, according to an embodiment of the present invention, the at least one reagent disposed in the cartridge includes at least one of;
  a. at least one target antibody;
  b. at least one positive control identifying antibody; and
  c. at least one negative control identifying detection moiety.

Moreover, according to an embodiment of the present invention, the at least one reagent disposed in the cartridge includes at least one reference composition including at least one of;
  a. a target signal reference composition; and
  b. a reference identifier composition.

Additionally, according to an embodiment of the present invention, the at least one reagent disposed in the cartridge includes at least one of;
  a. a positive control moiety; and
  b. a negative control moiety.

Furthermore, according to an embodiment of the present invention, the at least one reagent disposed in the cartridge includes at least one sepsis biomarker.

There is thus provided according to another embodiment of the present invention, a method for determining a biological condition in a subject, the method including;
  a. incubating a sample from the subject in the system described herein for a predetermined period of time; and
  b. receiving an indication responsive to the at least one reporter functionality thereby providing an indication of the biological condition in the subject in accordance with the chemical state.

Additionally, according to an embodiment of the present invention, the biological condition is selected from blood diseases such as leukemia, thrombocytopenia, immune system disorders, local infections, urinary tract disorders, autoimmune diseases and sepsis.

Furthermore, according to an embodiment of the present invention, the indication is quantitative.

Moreover, according to an embodiment of the present invention, the method is completed within twenty minutes.

There is thus provided according to another embodiment of the present invention, a method for determining a biological condition in a mammalian subject, the method including;
  a. incubating a specimen from the subject with at least one composition in a system described herein, for a predetermined period of time to form at least one reaction product, when the subject has the biological condition; and
  b. receiving an indication of the at least one reaction product responsive to at least one reporter element in the system thereby providing the indication of the biological condition in the subject.

There is thus provided according to another embodiment of the present invention, an automated method of determining the presence or absence of sepsis in a subject, including;
  a. contacting a blood sample from the subject with a fluorescently-labeled binding moiety in the system as described herein, the moiety specific to a sepsis marker, wherein the volume of the blood sample is 50 µL or smaller; and
  b. detecting the presence, absence or level of the binding moiety in the sample, thereby determining the presence or absence of sepsis in the subject within twenty minutes.

Furthermore, according to an embodiment of the present invention, wherein the sepsis marker is CD64.

Additionally, according to an embodiment of the present invention, the sepsis marker is CD163.

Moreover, according to an embodiment of the present invention, the method further includes contacting the blood sample with a second fluorescently-labeled binding moiety specific for a second sepsis marker.

Further, according to an embodiment of the present invention, the sepsis marker is CD64 and the second sepsis marker is CD163.

There is thus provided according to another embodiment of the present invention, a method for performing an assay for determining a chemical state in a self-contained stationary cartridge, the method including;
  a. introducing a sample into the system described herein;
  b. reacting at least one reagent with the sample; and
  c. detecting a signal associated with at least one reporter functionality, the at least one reporter functionality adapted to report a reaction of the at least one reagent with the sample, thereby determining the chemical state.

Furthermore, according to an embodiment of the present invention, the method further includes forming at least one product and detecting a signal associated with the product.

Additionally, according to an embodiment of the present invention the assay is a flow cytometric assay.

Further, according to an embodiment of the present invention, the chemical state is a biochemical state.

Further, according to an embodiment of the present invention, the biochemical state is indicative of a biological condition.

Furthermore, according to an embodiment of the present invention, the sample is a biological sample.

Additionally, according to an embodiment of the present invention, the biological sample is a bodily sample.

Furthermore, according to an embodiment of the present invention, the bodily sample is selected from the group consisting of blood, serum, plasma, urine, saliva, cerebrospinal fluid (CSF), serous fluid, peritoneal fluid and synovial fluid.

Moreover, according to an embodiment of the present invention, the at least one reagent includes at least one of;
 a. a cell surface marker;
 b. a cell stain;
 c. a reagent bound to a solid support;
 d. a chemical indicator; and
 e. a biological cell indicator.

Furthermore, according to an embodiment of the present invention, the cell surface marker is selected from the group consisting of CD64, CD4, CD8, a stem cell indicator, a Minimal Residual Disease indicator and a lymphocyte subtype indicator.

Additionally, according to an embodiment of the present invention, the cell stain is selected from the group consisting of a white blood cell differential indicator, an apoptosis indicator.

Further, according to an embodiment of the present invention, the reagent bound to the solid support is selected from the group consisting of an immobilized enzyme, an immobilized substrate, a plasma protein bead, an antibody bead, an antigen bead and an ELISA assay.

Additionally, according to an embodiment of the present invention, the chemical indicator is selected from the group consisting of a color indicator, a turbidity indicator, a pH indicator, an adsorption indicator, an emission indicator and a chemical reaction indicator.

Furthermore, according to an embodiment of the present invention, the biological cell indicator is selected from the group consisting of a cell cycle stage indicator, a cell proliferation indicator, a cytokine indicator, a metabolic indicator and an apoptosis indicator.

Further, according to an embodiment of the present invention, the at least one reagent includes at least two reagents.

Moreover, according to an embodiment of the present invention, the at least two reagents include at least one of;
 a. a cell surface marker and a cell element stain;
 b. a cell surface marker and a plasma protein bead assay;
 c. a cell surface marker and a solution change marker;
 d. a cell element stain and a plasma protein bead assay; and
 e. a cell element stain and a solution change marker.

Furthermore, according to an embodiment of the present invention, the biological condition is selected from blood diseases such as leukemia, thrombocytopenia immune system disorders, local infections, urinary tract disorders, autoimmune diseases and sepsis.

There is thus provided according to another embodiment of the present invention, a method for forming a chemical reaction in a stationary cartridge, the method including;
 a. storing at least one composition in the cartridge described herein; and
 b. activating at least one inflatable chamber in the cartridge to provide at least one pressure force to the at least one reagent thereby inducing the chemical reaction.

There is thus provided according to an embodiment of the present invention, a kit for evaluating a biological condition in a patient, the kit comprising;
 a) a disposable element for receiving a biological specimen and for combining said specimen with at least one composition;
 b) at least one composition comprising at least one detector moiety adapted to react with said specimen to form a reaction product, when said patient has said biological condition; and
 c) at least one reporter element adapted to provide an indication of reaction product thereby providing the indication of the biological condition.

Additionally, according to an embodiment of the present invention, the kit further comprises;
 d) instructions for using the kit.

Furthermore, according to an embodiment of the present invention, the disposable element is a disposable cartridge.

Moreover, according to an embodiment of the present invention, the disposable cartridge is a disposable microfluidics cartridge.

Additionally, according to an embodiment of the present invention, the disposable microfluidics cartridge comprises at least one of the following elements:
 a) a reservoir;
 b) a pump;
 c) a conduit;
 d) a miniaturized flow cell;
 e) a transport channel;
 f) a microfluidic element;
 g) a compressed gas holding element;
 h) a compressed gas releasing element;
 i) a nozzle element;
 j) a mixing element;
 k) a bellows element;
 l) software adapted to activate said elements according to a specific sequence; and
 m) hardware to activate said elements according to a specific sequence.

Additionally, according to an embodiment of the present invention, the disposable microfluidics cartridge comprises at least two of the elements.

Additionally, according to an embodiment of the present invention, the disposable microfluidics cartridge comprises at least three of the elements.

Additionally, according to an embodiment of the present invention, the disposable microfluidics cartridge comprises at least four of the elements.

Additionally, according to an embodiment of the present invention, the disposable microfluidics cartridge comprises at least five of the elements.

Additionally, according to an embodiment of the present invention, the disposable microfluidics cartridge comprises at least ten of the elements.

Additionally, according to an embodiment of the present invention, the disposable microfluidics cartridge comprises at least twenty of the elements.

Additionally, according to an embodiment of the present invention, the disposable microfluidics cartridge comprises at least thirty of the elements.

According to an embodiment of the present invention, the microfluidics kit is configured to provide the rapid indication with one hour.

According to another embodiment of the present invention, the microfluidics kit is configured to provide the rapid indication with thirty minutes.

According to another embodiment of the present invention, the microfluidics kit is configured to provide the rapid indication with fifteen minutes.

According to another embodiment of the present invention, the microfluidics kit is configured to provide the rapid indication with ten minutes.

According to another embodiment of the present invention, the microfluidics kit is configured to provide the rapid indication with five minutes.

According to another embodiment of the present invention, the microfluidics kit is configured to provide the rapid indication with one minute.

According to another embodiment of the present invention, the microfluidics kit is configured to provide the rapid indication with thirty seconds.

According to another embodiment of the present invention, the microfluidics kit is configured to provide the rapid indication with ten seconds.

According to another embodiment of the present invention, the microfluidics kit is configured to provide the rapid indication with one second.

There is thus provided according to an embodiment of the present invention, a microfluidics assay kit for performing a rapid biological assay, the kit comprising;
  a) a disposable element comprising a reactant, the disposable element being adapted to receive a sample comprising a biological entity and for combining said reactant with said biological entity to form a reaction product; and
  b) at least one reporter element adapted to provide a rapid indication of disappearance of said reactant thereby providing rapid assay of the biological entity.

There is thus provided according to an embodiment of the present invention, a microfluidics assay kit for performing a rapid assay of a biological entity, the kit comprising;
  a) a disposable element comprising a reactant, the disposable element being adapted to receive a sample comprising the biological entity and for combining said reactant with said biological entity to form a reaction product; and
  b) at least one reporter element adapted to provide a rapid indication of appearance of said reaction product thereby providing rapid assay of the biological entity.

There is thus provided according to an embodiment of the present invention, a composition for evaluating a biological condition, the composition comprising;
  a. a sample composition comprising at least one of;
    i. a bodily specimen comprising a target moiety;
    ii. a positive control moiety; and
    iii. a negative control moiety;
  b. a detection composition comprising at least one of;
    i. at least one target antibody;
    ii. at least one positive control identifying antibody; and
    iii. at least one negative control identifying detection moiety or characteristic; and
  c. at least one reference composition comprising at least one of;
    i. a target signal reference composition; and
    ii. a reference identifier composition.

There is thus provided according to another embodiment of the present invention a composition for evaluating a biological condition, the composition comprising;
  a. a sample composition comprising at least one of;
    iii. a bodily specimen comprising a target moiety;
    iv. a positive control moiety; and
    v. a negative control moiety;
  b. an antibody composition comprising at least one of;
    vi. at least one target antibody (CD64 antibody);
    vii. at least one positive control identifying antibody (CD163); and
    viii. at least one negative control identifying antibody or characteristic; and
  c. at least one reference composition comprising at least one of;
    ix. a target signal reference composition; and
    x. a reference identifier composition.

Additionally, according to an embodiment of the present invention, the composition further comprises at least one conditioning moiety comprising;
  d. at least one lysis reagent; and
  e. at least one diluent.

Furthermore, according to an embodiment of the present invention, the biological condition is selected from a group consisting of blood diseases such as leukemia, thrombocytopenia immune system disorders, local infections, urinary tract disorders, autoimmune diseases and sepsis.

Moreover, according to an embodiment of the present invention the bodily specimen is selected from a group consisting of blood, serum, plasma, urine, saliva, cerebrospinal fluid (CSF), serous fluid, peritoneal fluid and synovial fluid.

According to another embodiment of the present invention, the target moiety includes a CD64 surface antigen on neutrophils.

Additionally, according to a further embodiment of the present invention, the positive control moiety includes monocytes and the negative control includes lymphocytes.

Additionally, according to an embodiment of the present invention, the target moiety is CD64 on neutrophils, the positive control moiety includes CD64 expression on monocytes, and the negative control moiety includes lymphocytes without CD64 expression.

Further, according to an embodiment of the present invention, the target indicator is bound to a signaling moiety on the at least one target antibody.

Yet further, according to an embodiment of the present invention, the at least one reference composition includes beads.

Additionally, according to an embodiment of the present invention, the beads include polystyrene microbeads.

Moreover, according to an embodiment of the present invention, the target antibody reference composition includes a first fluorescent signal and the reference identifier composition includes a second fluorescent signal.

Furthermore, according to an embodiment of the present invention, the first fluorescent signal includes FITC and the second fluorescent signal includes Starfire Red fluor.

There is thus provided according to an embodiment of the present invention, a method of quantifying a biomarker in a sample, comprising;
  a. contacting the sample with a fluorescently-labeled binding moiety that specifically binds to the biomarker;
  b. detecting a first fluorescent signal from at least a portion of the labeled sample;

c. detecting a second fluorescent signal from a population of fluorescently-labeled particles, wherein the population includes a known fluorescent intensity over a fixed time; and d. normalizing the first fluorescent signal to the second fluorescent signal, thereby quantifying the biomarker, wherein the normalizing includes using a device comprising software capable of comparing the first and second fluorescent signal.

Furthermore, according to an embodiment of the present invention, the biomarker is a sepsis biomarker.

Moreover, according to an embodiment of the present invention, the biomarker is CD64 or CD163.

Additionally, according to an embodiment of the present invention, the sample is a blood sample.

According to another embodiment of the present invention, the fluorescent label of the binding moiety and the fluorescent label of the particles is the same fluorescent label.

Further, according to an embodiment of the present invention, the binding moiety is an antibody.

According to an embodiment of the present invention, the software is capable of recognizing a specific lot of fluorescently-labeled particles.

Moreover, according to an embodiment of the present invention, the individual fluorescent signals include at least one first fluorescent signal and at least one second fluorescent signal.

Additionally, according to an embodiment of the present invention the fluorescently-labeled binding moiety targets a first cell population and a second cell population in the sample.

According to another embodiment of the present invention the detection of binding of the binding moiety to the second cell population provides an internal positive control for the sample.

Furthermore, according to an embodiment of the present invention, the binding moiety is anti-CD64 antibody and the first cell population includes polymorphonuclear leukocytes.

Yet further, according to an embodiment of the present invention, the second cell population includes monocytes.

According to an embodiment of the present invention, the method further comprises the step of determining the presence of at least one cell population in the sample that is not bound by the binding moiety, thus providing an internal negative control for the sample.

There is thus provided according to another embodiment of the present invention, a composition for evaluating a biological condition, the composition comprising;
a. a sample comprising at least one of;
  i. a bodily specimen comprising a target moiety;
  ii. a positive control moiety; and
  iii. a negative control moiety;
b. an antibody composition comprising at least one of;
  iv. at least one target antibody;
  v. at least one positive control identifying antibody; and
  vi. at least one negative control identifying antibody or characteristic; and
c. at least one reference composition comprising at least one of;
  vii. a target antibody reference composition; and
  viii. a reference identifier composition.

According to an embodiment of the present invention, the composition further comprises at least one conditioning moiety comprising;
a) at least one lysis reagent; and
b) at least one diluent.

There is thus provided according to another embodiment of the present invention, a method of determining the presence or absence of sepsis in a subject, the method including;
a) contacting a blood sample from the subject with a fluorescently-labeled binding moiety specific to a sepsis marker, wherein the volume of the blood sample is 50 µL or smaller; and
b) detecting the presence, absence or level of the binding moiety in the sample, thereby determining the presence or absence of sepsis in the subject.

There is thus provided according to another embodiment of the present invention, a method of quantifying a biomarker in a sample, comprising;
a) contacting the sample with a fluorescently-labeled binding moiety that specifically binds to the biomarker;
b) detecting a first fluorescent signal from at least a portion of the labeled sample;
c) detecting a second fluorescent signal from a population of fluorescently-labeled particles, wherein the population includes a known fluorescent intensity over a fixed time; and
d) normalizing the first fluorescent signal to the second fluorescent signal, thereby quantifying the biomarker, wherein the normalizing includes using a device comprising software capable of comparing the first and second fluorescent signal.

According to some embodiments, the sample may be liquid, according to other embodiments, the sample may be a colloid or suspension. According to further embodiments, the sample may be a solid, such as in a powder or crystal form.

Typical turnaround times for diagnostic prior art assays are 30-120 minutes. Often, the time lost in waiting for laboratory results can lead to a further deterioration in a patient, and sometimes death. In some cases, the physician has to act without having the laboratory results. This can lead to providing the patient with the wrong treatment. The present invention provides rapid assays to save lives and provide fast correct treatments to a patient.

There is thus provided according to an embodiment of the present invention automated method of determining the presence or absence of sepsis in a subject, including;
a) contacting a blood sample from the subject with a fluorescently-labeled binding moiety specific to a sepsis marker, wherein the volume of the blood sample is 50 µL or smaller; and
b) detecting the presence, absence or level of the binding moiety in the sample, thereby determining the presence or absence of sepsis in the subject within twenty minutes.

Additionally, according to an embodiment of the present invention, the sepsis marker is CD64.

Furthermore, according to an embodiment of the present invention, a second sepsis marker is CD163.

Moreover, according to an embodiment of the present invention, the method further includes contacting the blood sample with a second fluorescently-labeled binding moiety specific for a second sepsis marker.

Further, according to an embodiment of the present invention, the sepsis marker is CD64 and the second sepsis marker is CD163.

Additionally, according to an embodiment of the present invention, the binding moiety is an antibody.

Moreover, according to an embodiment of the present invention, the detecting step is performed in a device capable of receiving the sample and capable of detecting the binding moiety.

Additionally, according to an embodiment of the present invention, the method further includes the step of calibrating the device by detecting a population of the fluorescently-labeled particles.

According to another embodiment of the present invention, the particles include the same fluorescent label as the fluorescently-labeled binding moiety.

Additionally, according to an embodiment of the present invention, the method further includes a second population of particles that include the same fluorescent label as the second fluorescently-labeled binding moiety.

Moreover, according to an embodiment of the present invention, the method further includes performing an internal calibration after the detecting the fluorescently-labeled binding moiety.

Notably, according to an embodiment of the present invention, the calibration is completed in less than 5 minutes.

According to some embodiments, the particles are microbeads.

Additionally, according to an embodiment of the present invention, the method is performed in less than 15 minutes.

Furthermore, according to an embodiment of the present invention, the method, further includes the step of determining the presence of at least one cell population in the sample that is not bound by the binding moiety, thus providing an internal negative control for the sample.

The present invention will be more fully understood from the following detailed description of the preferred embodiments thereof, taken together with the drawings.

BRIEF DESCRIPTION OF THE DRAWINGS

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a simplified three dimensional front view of a system for detecting a biological condition, in accordance with an embodiment of the present invention;

FIG. 1B is a simplified three dimensional inner front view of a reader assembly for detecting a biological condition, in accordance with an embodiment of the present invention;

FIG. 1C is a simplified three dimensional inner rear view of a reader assembly for detecting a biological condition, in accordance with an embodiment of the present invention;

FIG. 2A is a simplified blown up diagram of an optical reader assembly for detecting a biological condition, in accordance with an embodiment of the present invention;

FIG. 2B is another simplified blown up diagram of a photomultiplier tube of the optical reader assembly for detecting a biological condition, in accordance with an embodiment of the present invention;

FIG. 3A shows a reader optics assembly, a cartridge handling unit, and a forward scatter detection unit, in accordance with an embodiment of the present invention;

FIG. 3B shows a right side view of a reader optics assembly, in accordance with an embodiment of the present invention;

FIG. 3C shows a left side view of a reader optics assembly, in accordance with an embodiment of the present invention;

FIG. 3D is a forward scatter detection assembly, in accordance with an embodiment of the present invention;

FIG. 3E is a side view of the forward scatter detection assembly, in accordance with an embodiment of the present invention;

FIG. 4A shows a cutaway view of a reader assembly, in accordance with an embodiment of the present invention;

Figure 1A:
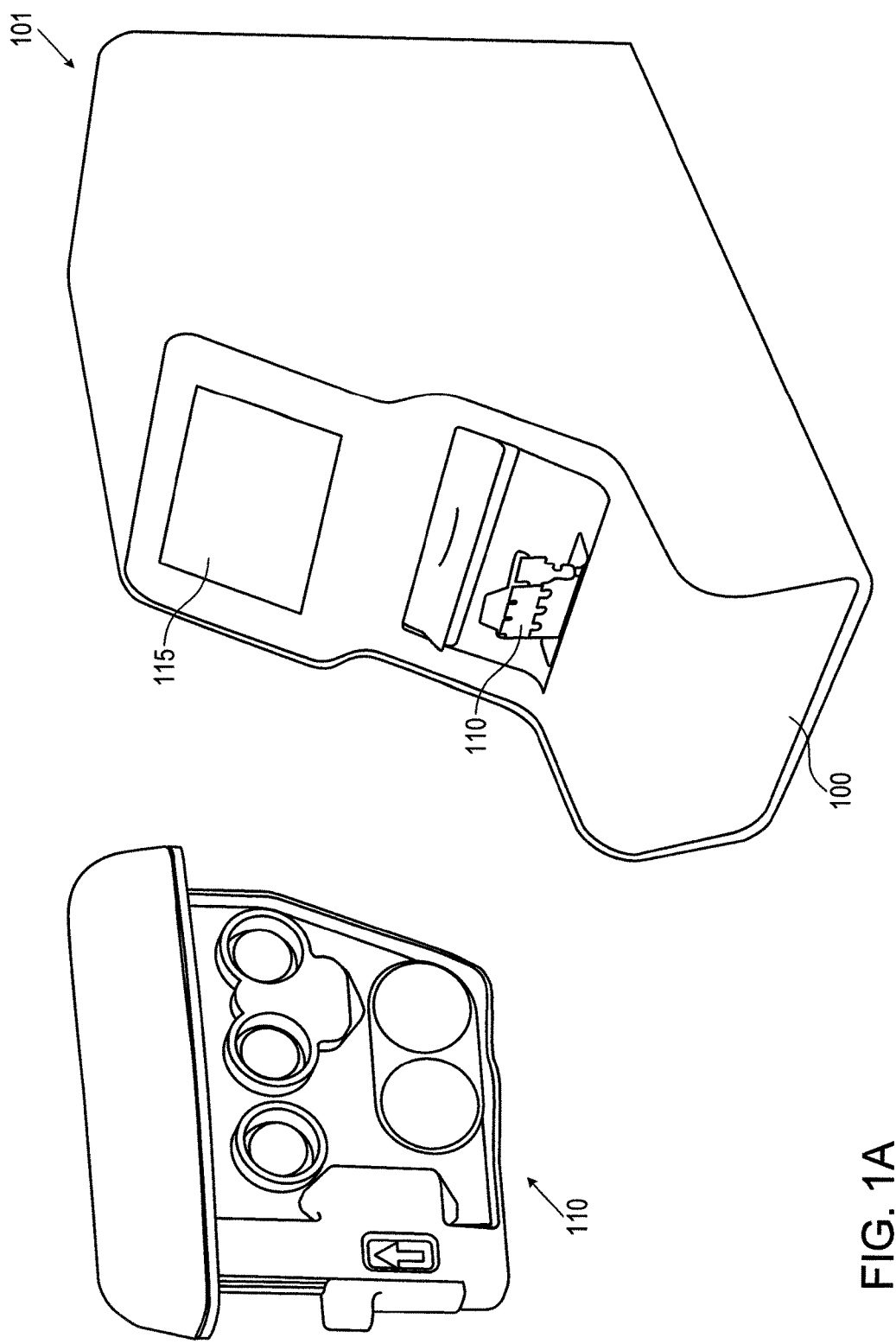
Figure 4A:
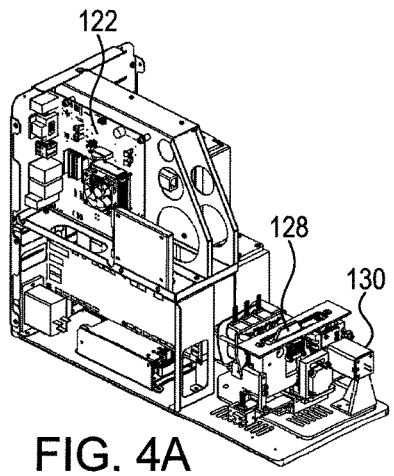
Figure 4B:
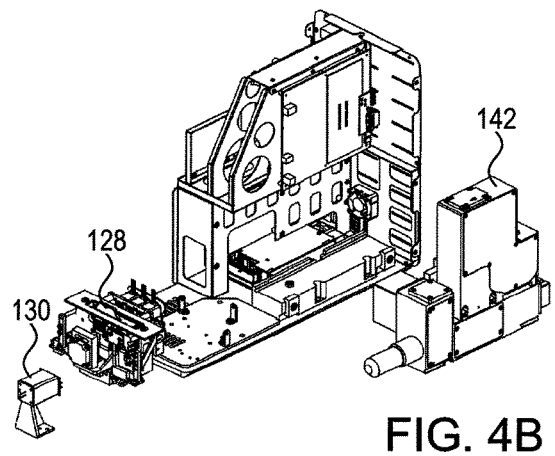
Figure 4C:
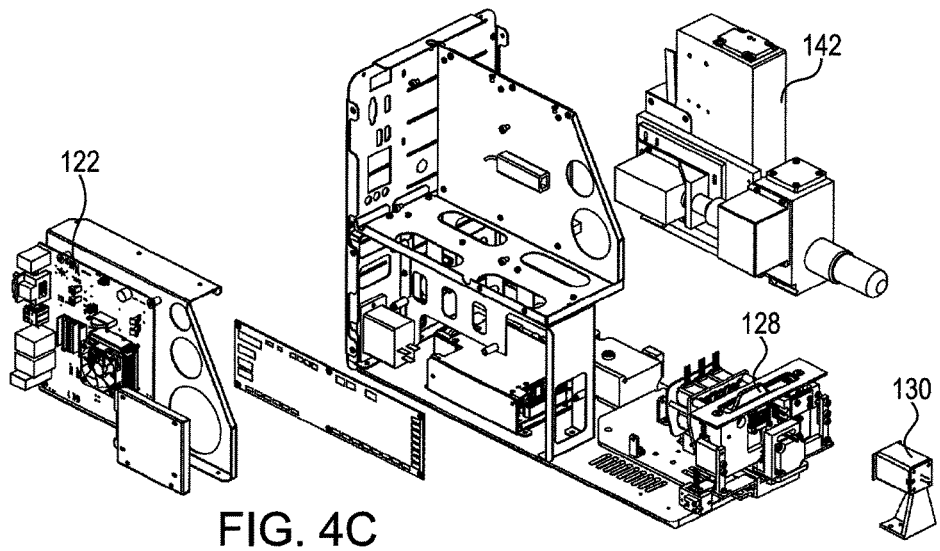
Figure 4D:
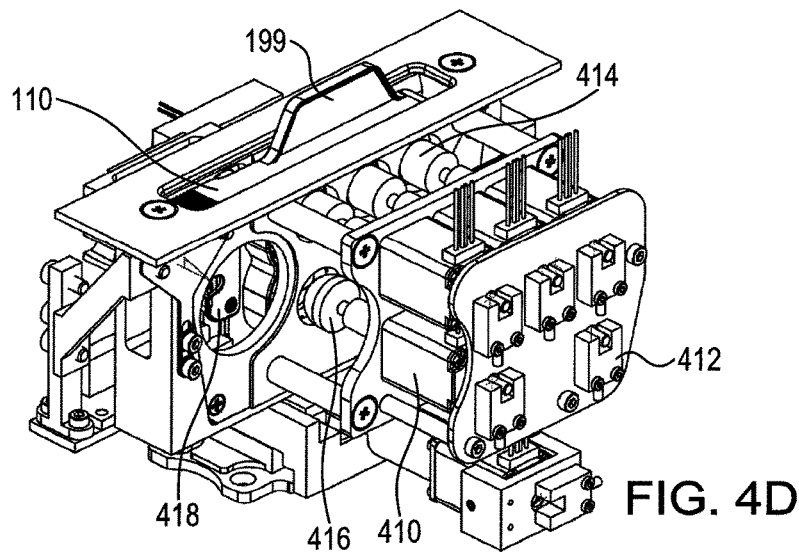
Figure 4E:
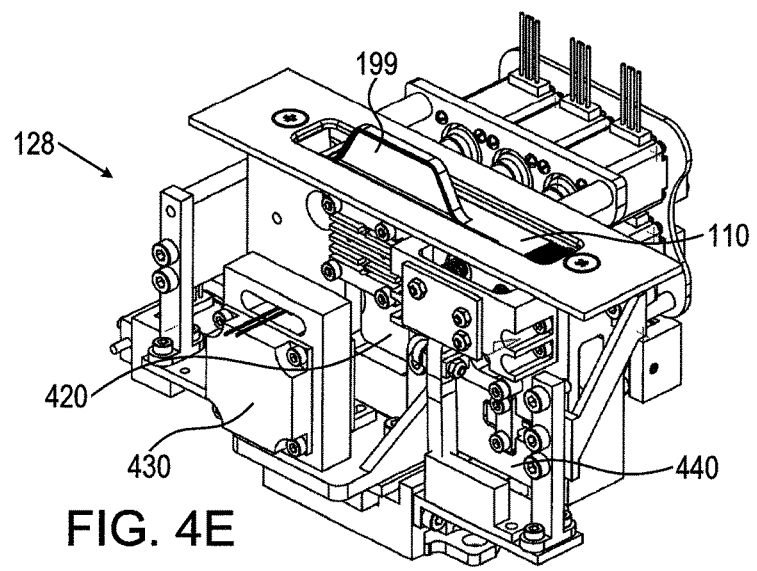
Figure 5:
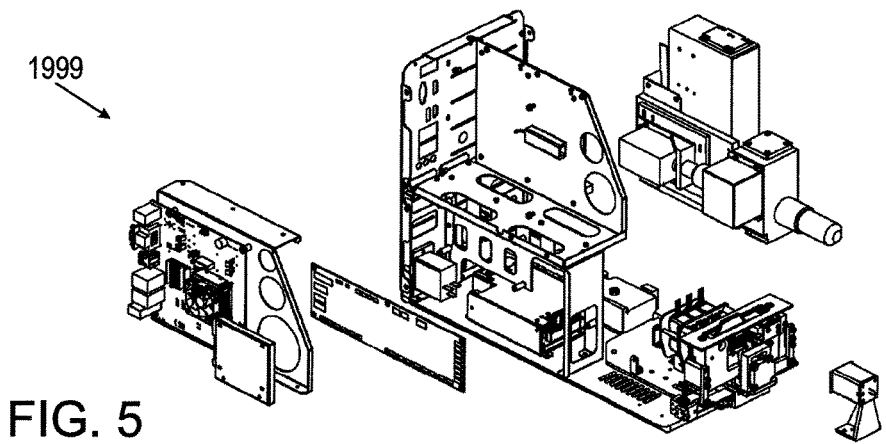
Figure 6:
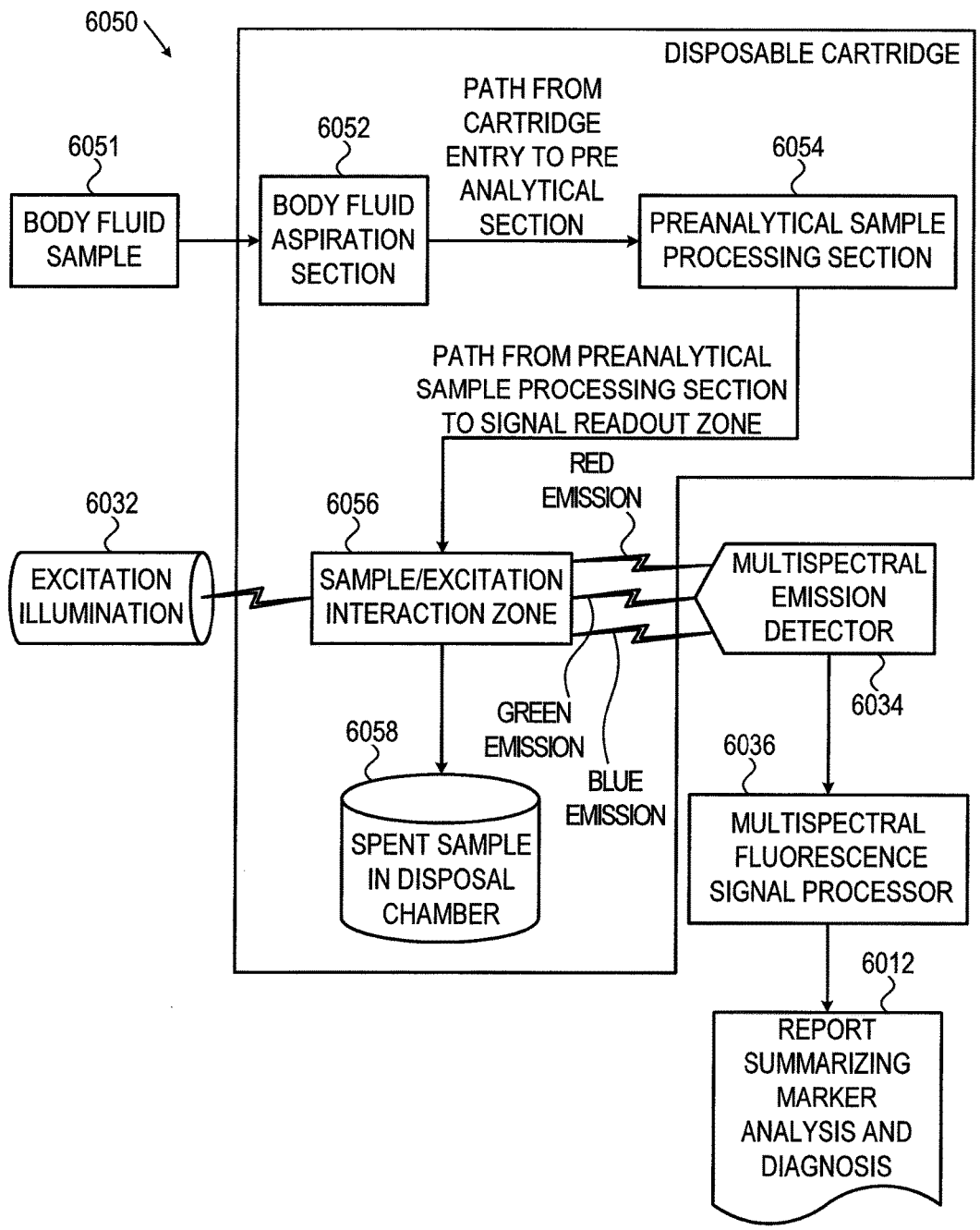
Figure 7A:
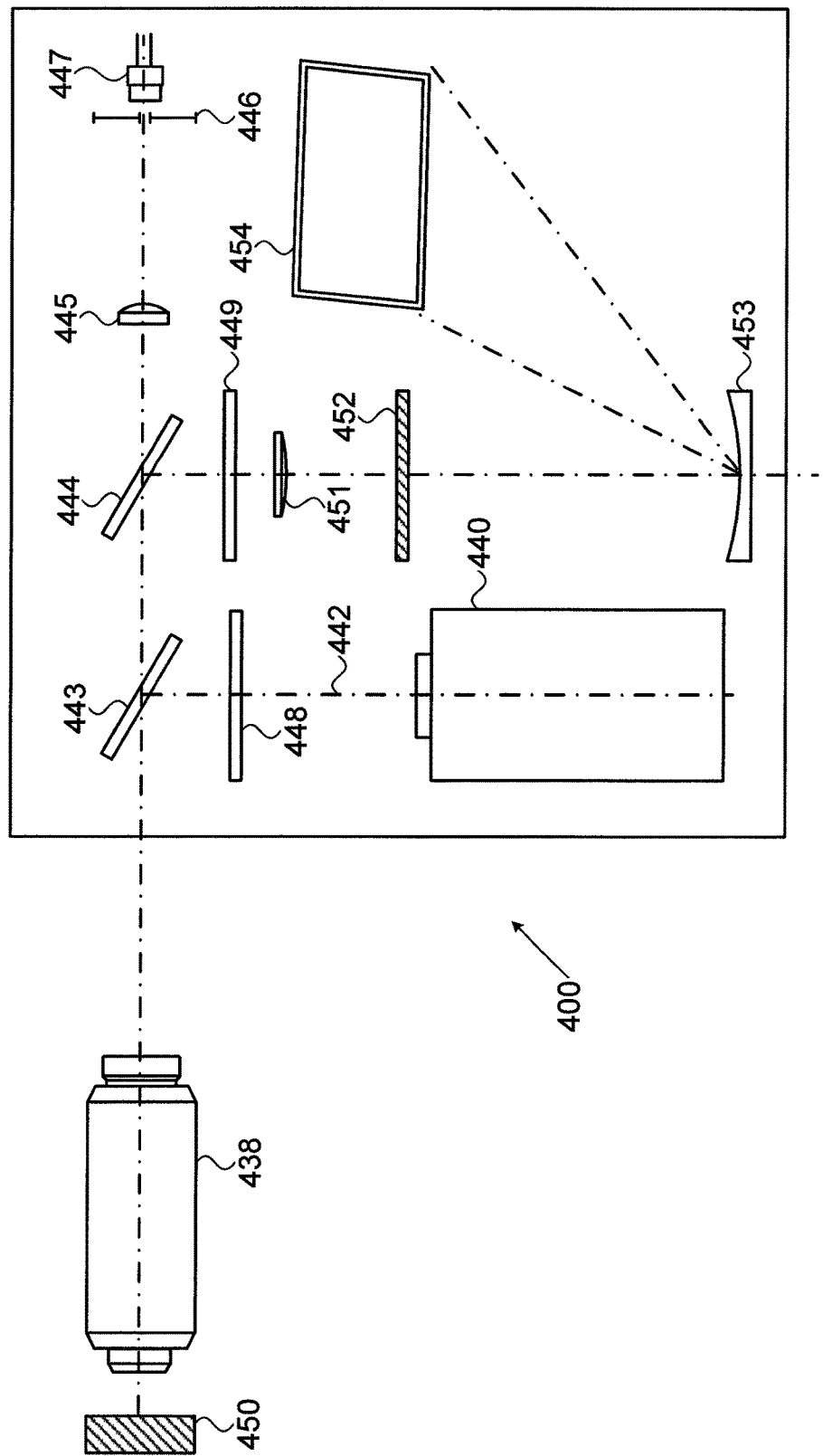
Figure 7B:
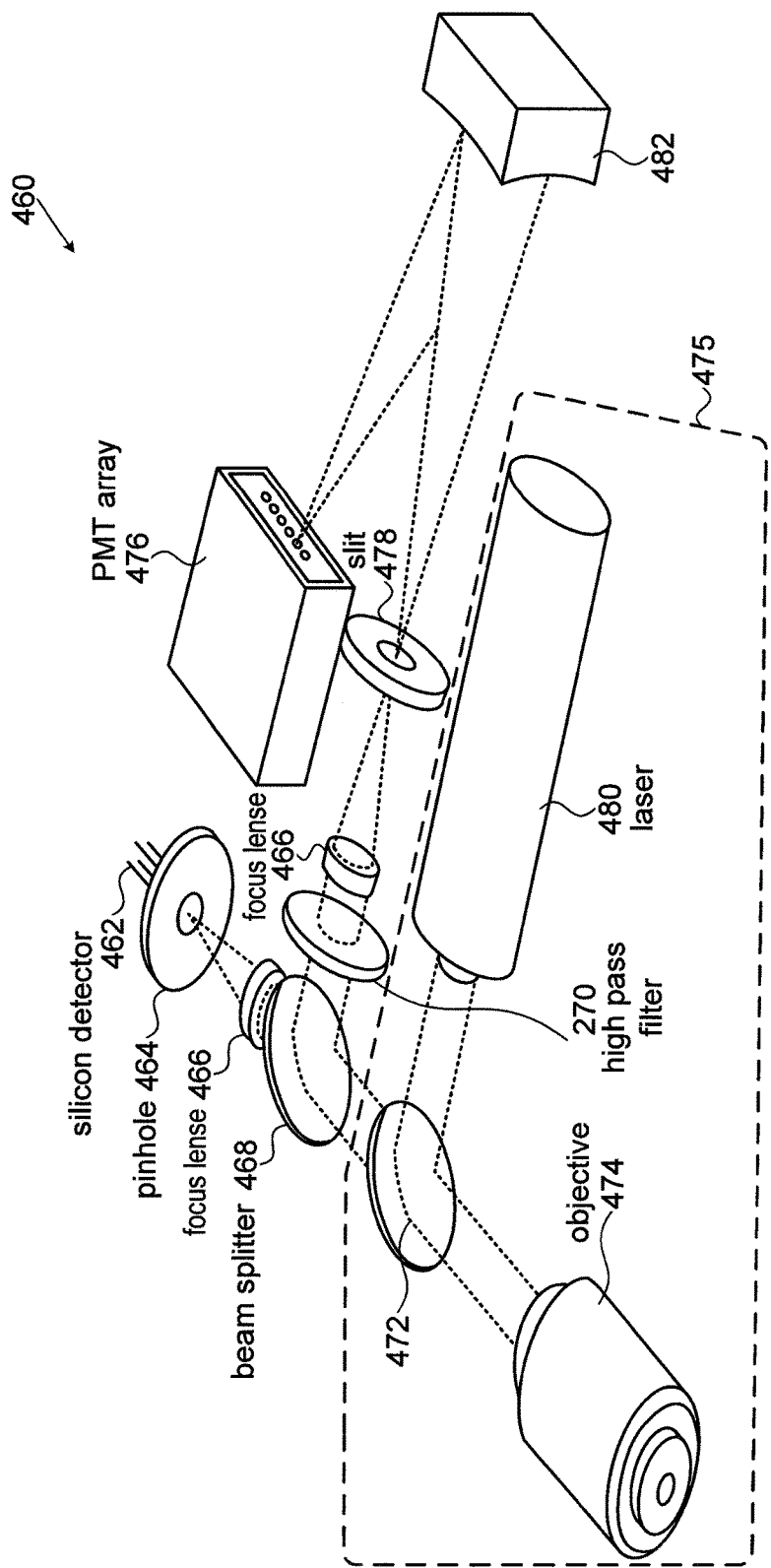
Figure 8A:
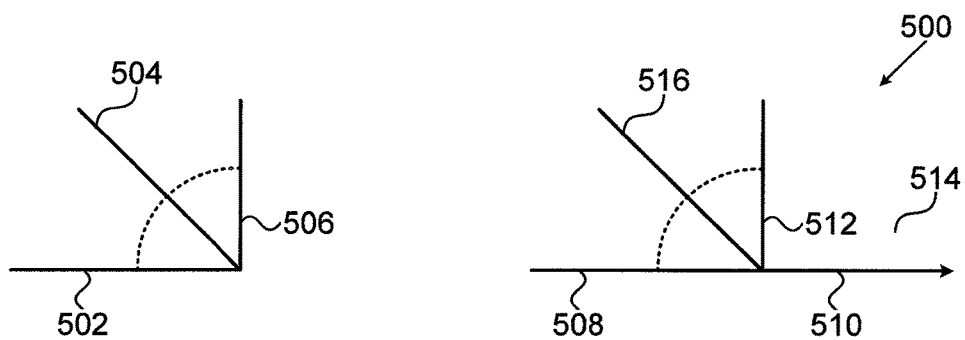
Figure 8B:
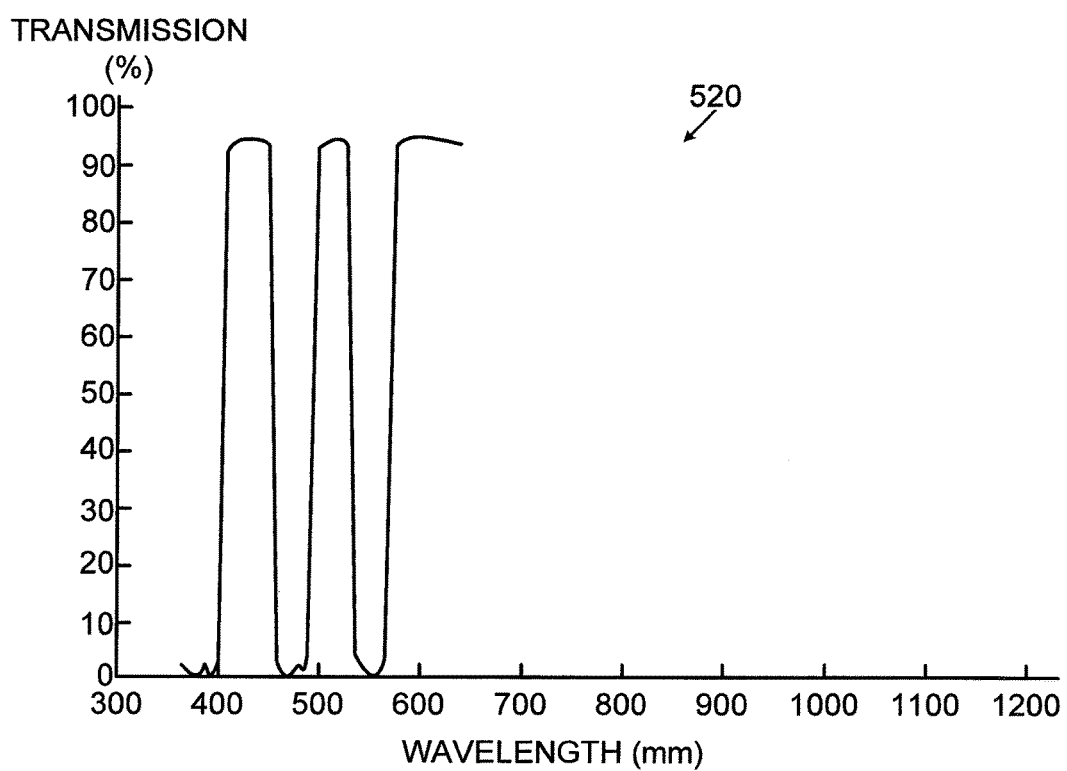
Figure 8C:
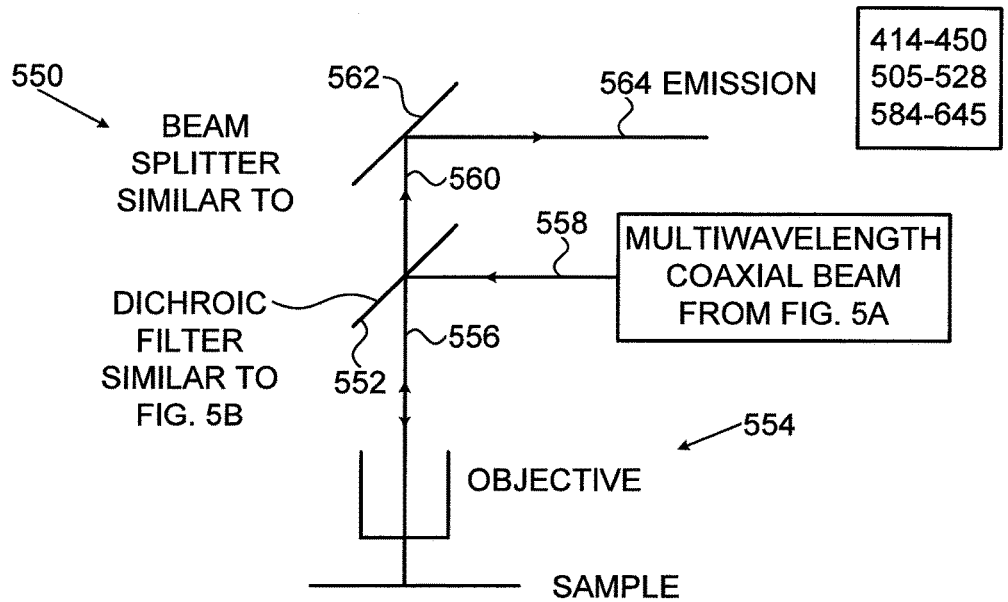

FIG. 4B shows an exploded right side view of a reader assembly, in accordance with an embodiment of the present invention;

FIG. 4C shows a left side blown up view of the reader assembly, in accordance with an embodiment of the present invention;

FIG. 4D shows a rear view of a cartridge handling unit (CHU), in accordance with an embodiment of the present invention;

FIG. 4E shows a front view of a cartridge handling unit (CHU), in accordance with an embodiment of the present invention;

FIG. 5 shows an exploded view of a reader optics assembly, in accordance with an embodiment of the present invention;

FIG. 6 is a simplified illustration of a disposable cartridge of the system of FIG. 1A, in accordance with an embodiment of the present invention;

FIG. 7A is a simplified schematic illustration of an optical arrangement of a reader optics assembly, in accordance with an embodiment of the present invention;

FIG. 7B is another simplified schematic illustration of optical arrangement of a reader optics assembly, in accordance with an embodiment of the present invention;

FIG. 8A is a schematic representation of one example of multi-wavelength excitation in the optical unit of FIG. 7A or 7B, in accordance with an embodiment of the present invention;

FIG. 8B shows a graphical output of transmission as a function of wavelength for a dichroic filter of FIG. 7B, employing the multi-wavelength excitation of FIG. 8A, in accordance with an embodiment of the present invention;

FIG. 8C is a schematic representation of part of the optical unit employing multi-wavelength excitation of FIG. 8A and the dichroic filter of FIG. 5B, in accordance with an embodiment of the present invention.

Figure 9A:
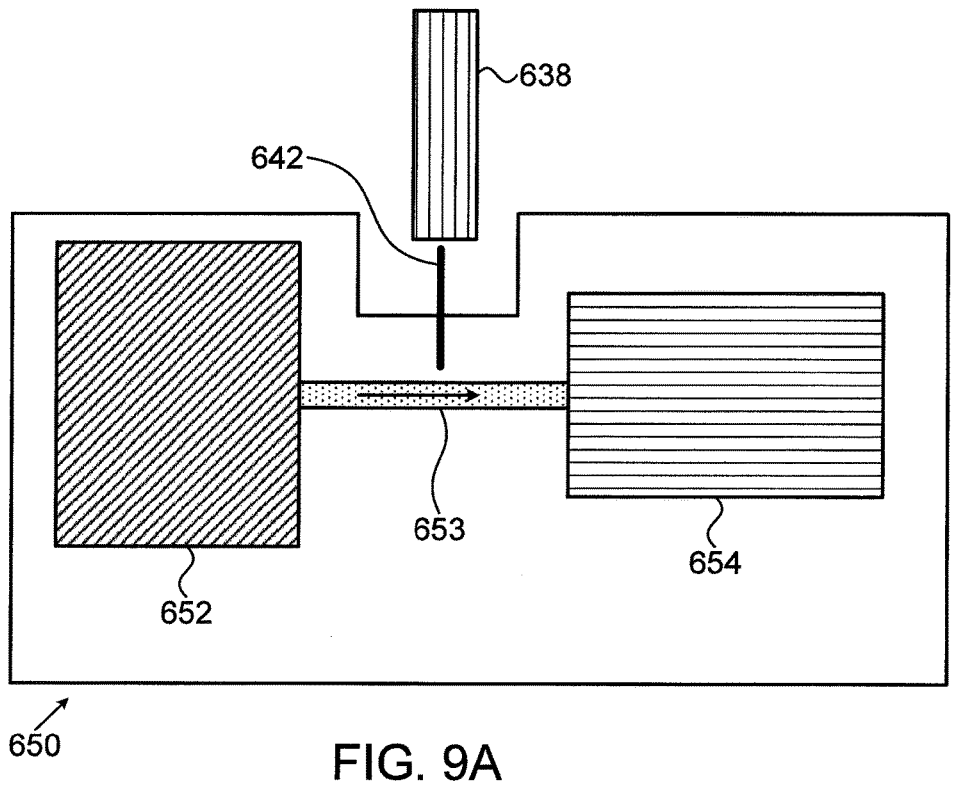
Figure 9B:
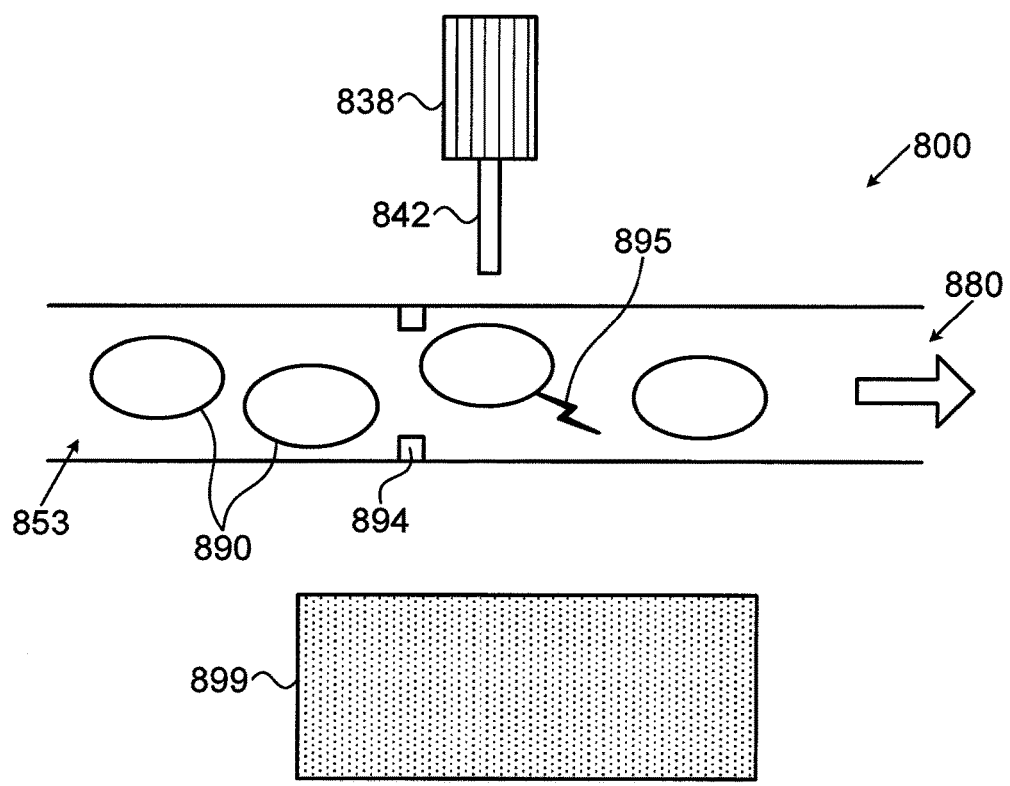
Figure 10:
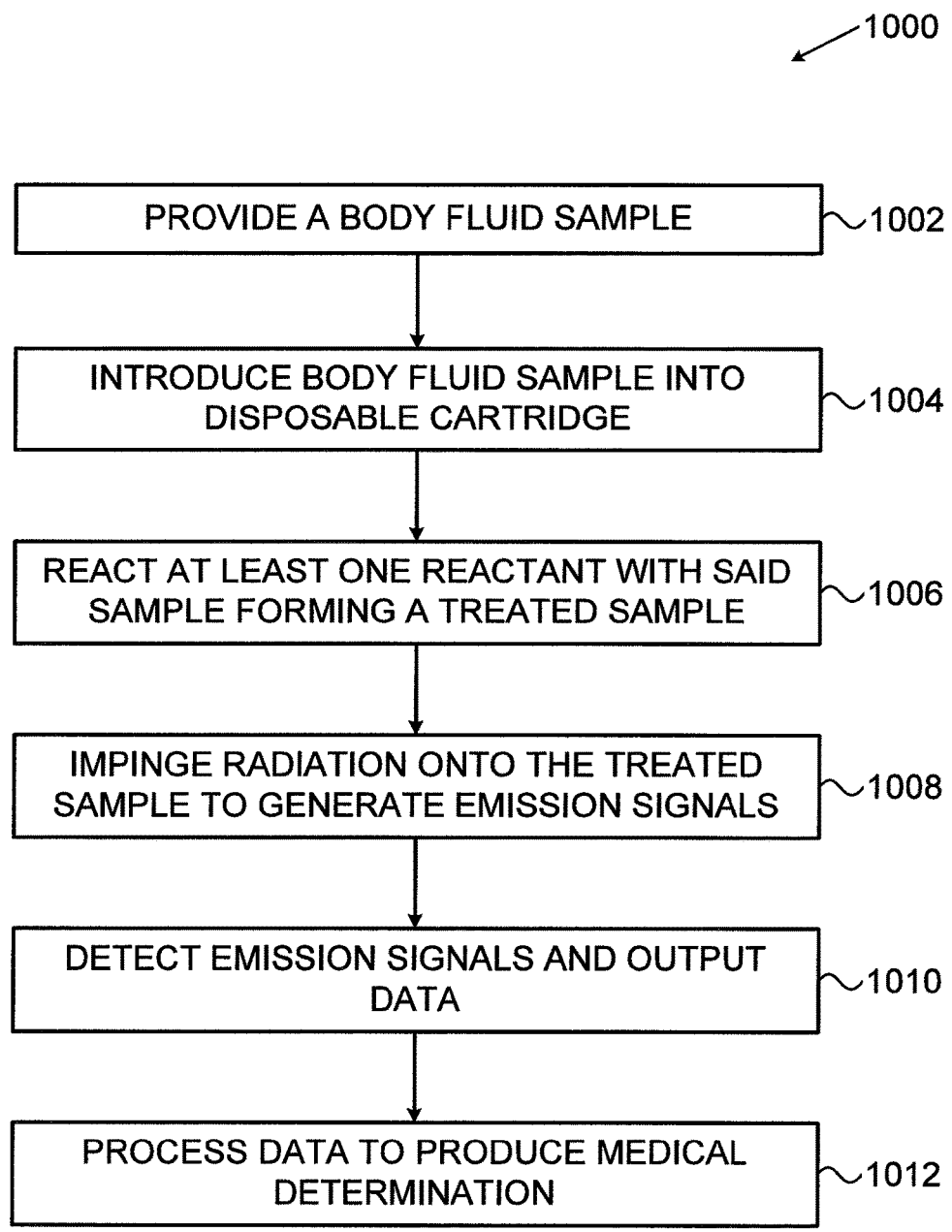
Figure 11:
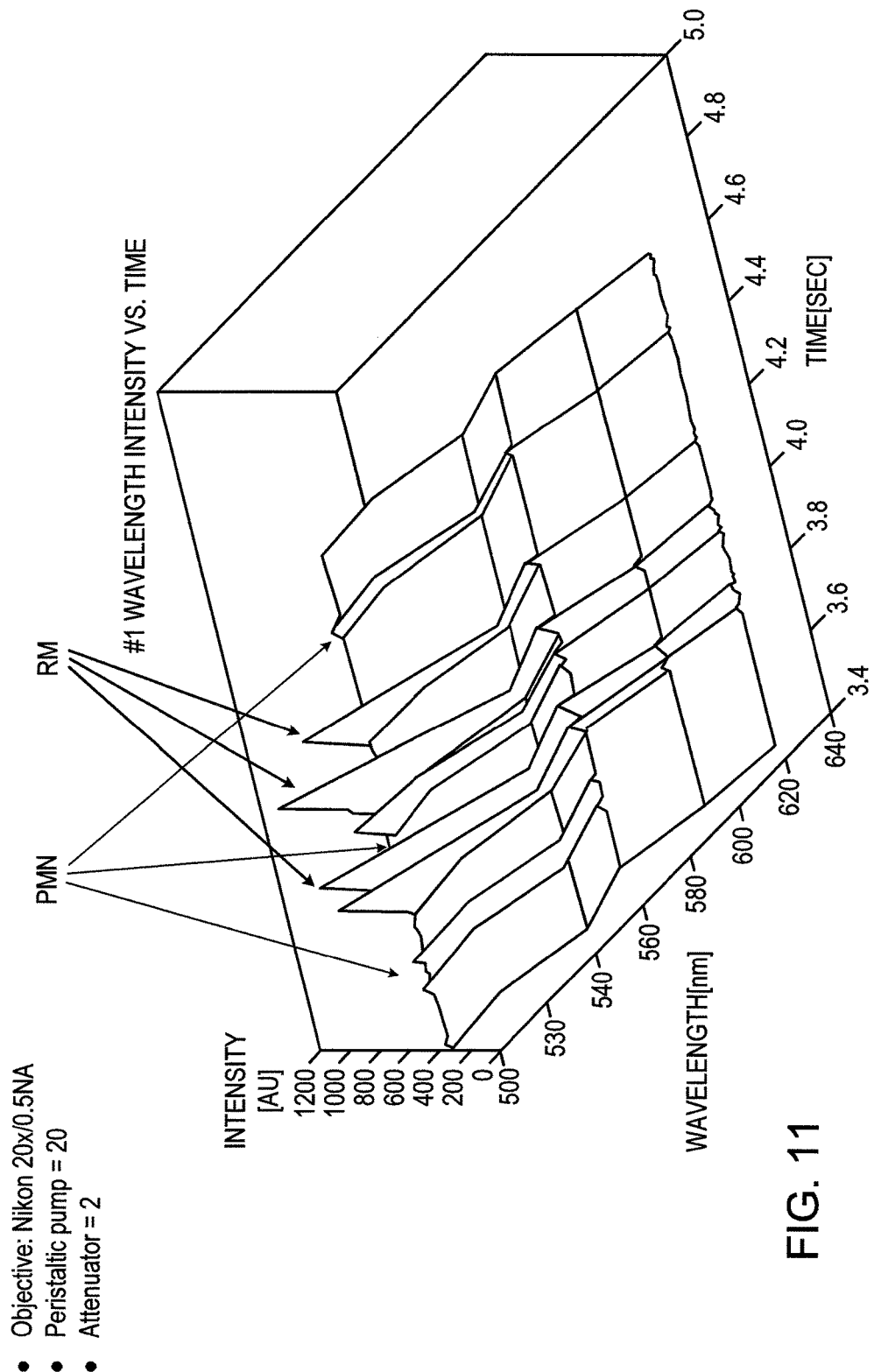
Figure 12A:
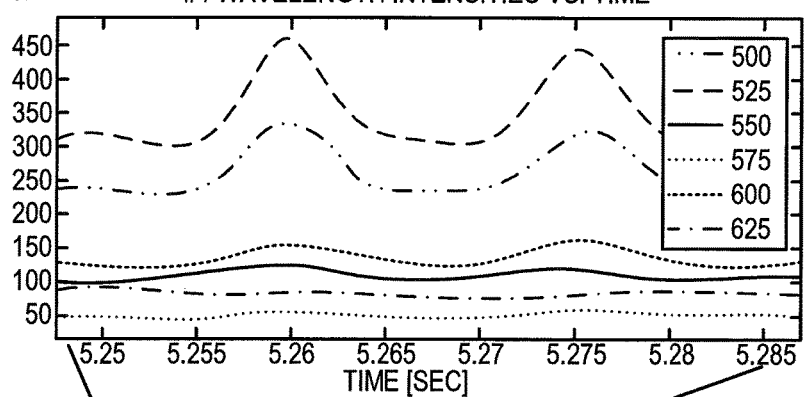
Figure 12B:
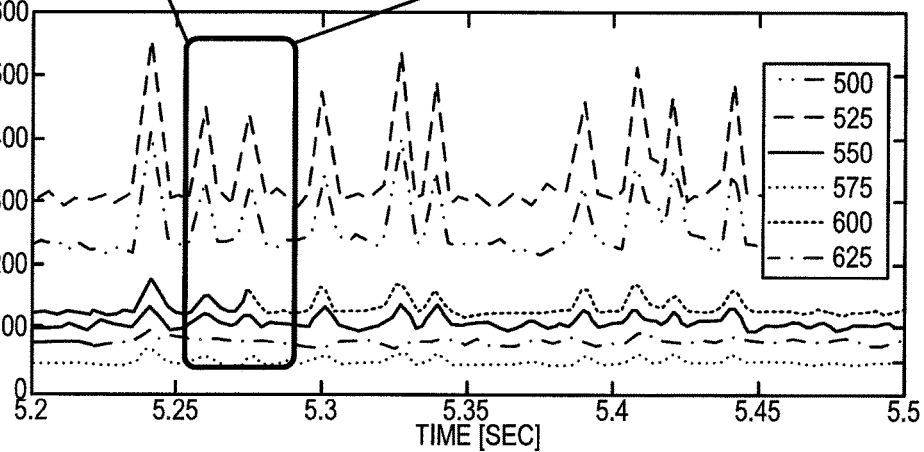
Figure 12C:
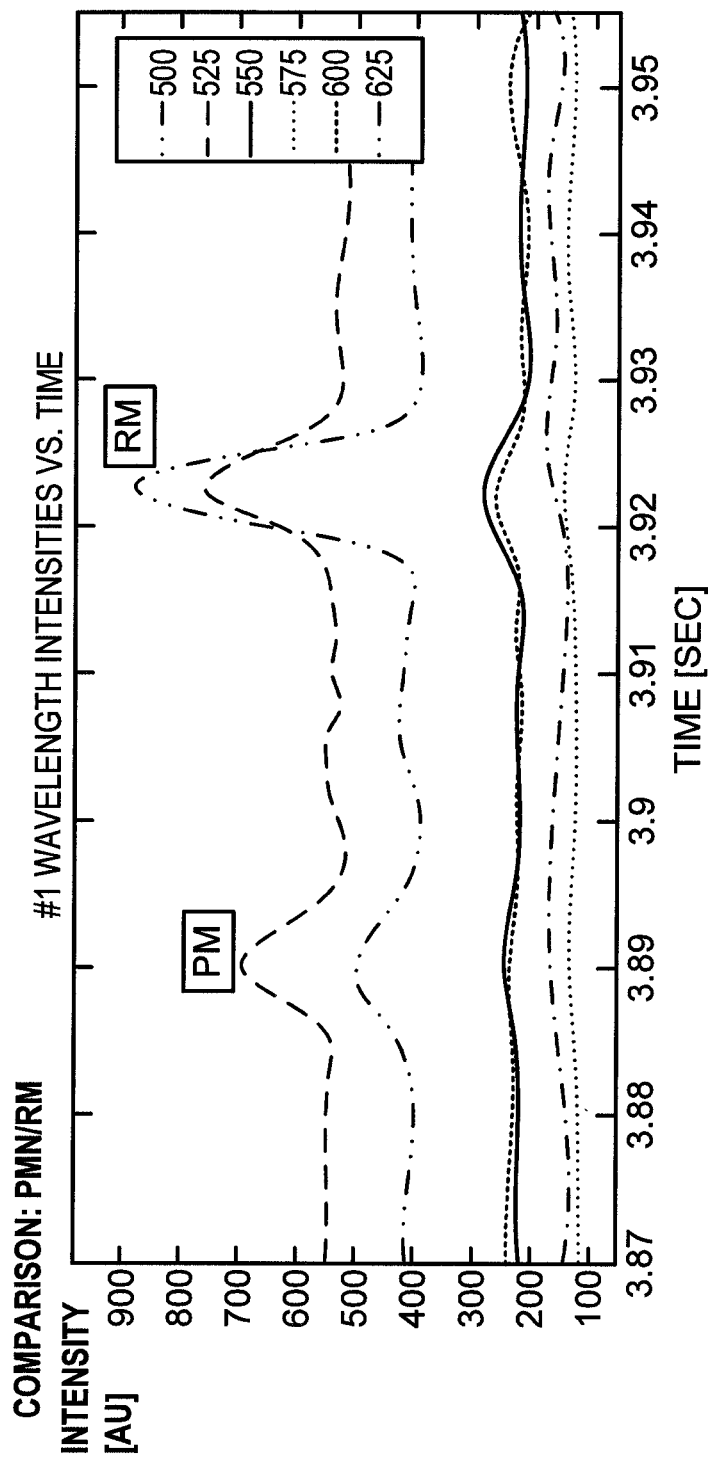
Figure 13A:
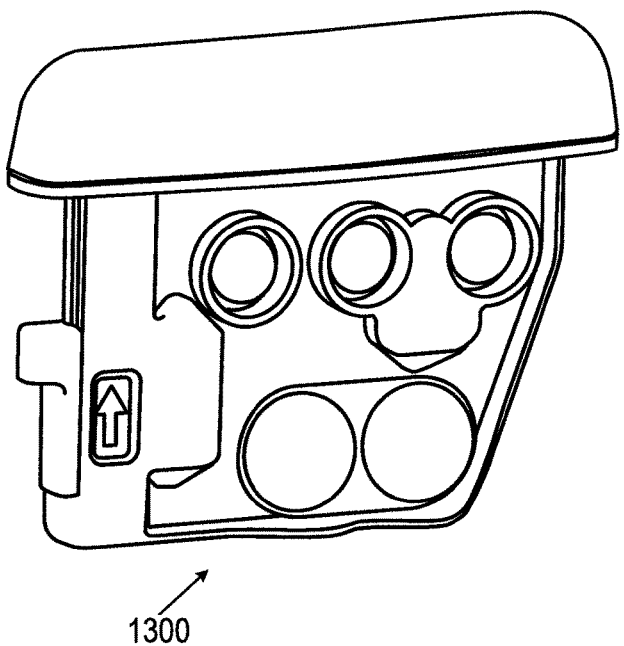
Figure 13B:
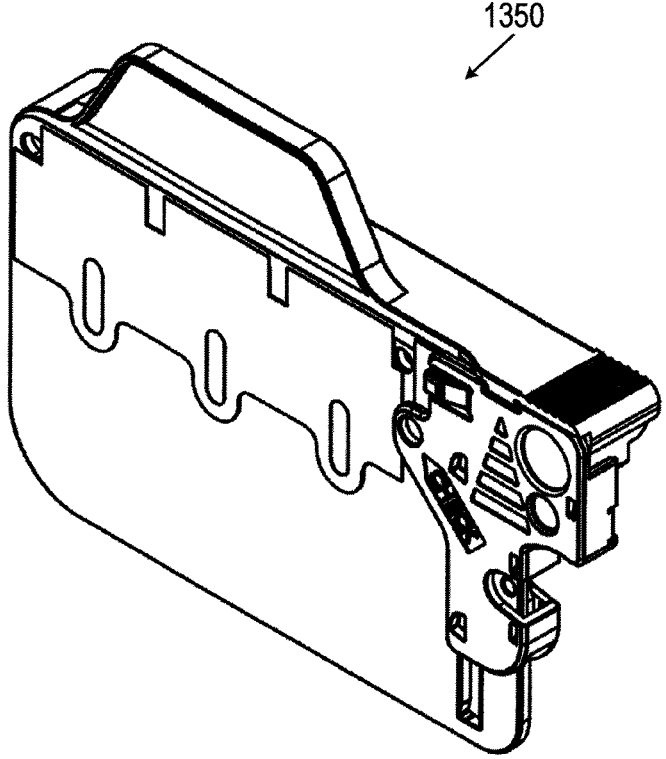
Figure 14A:
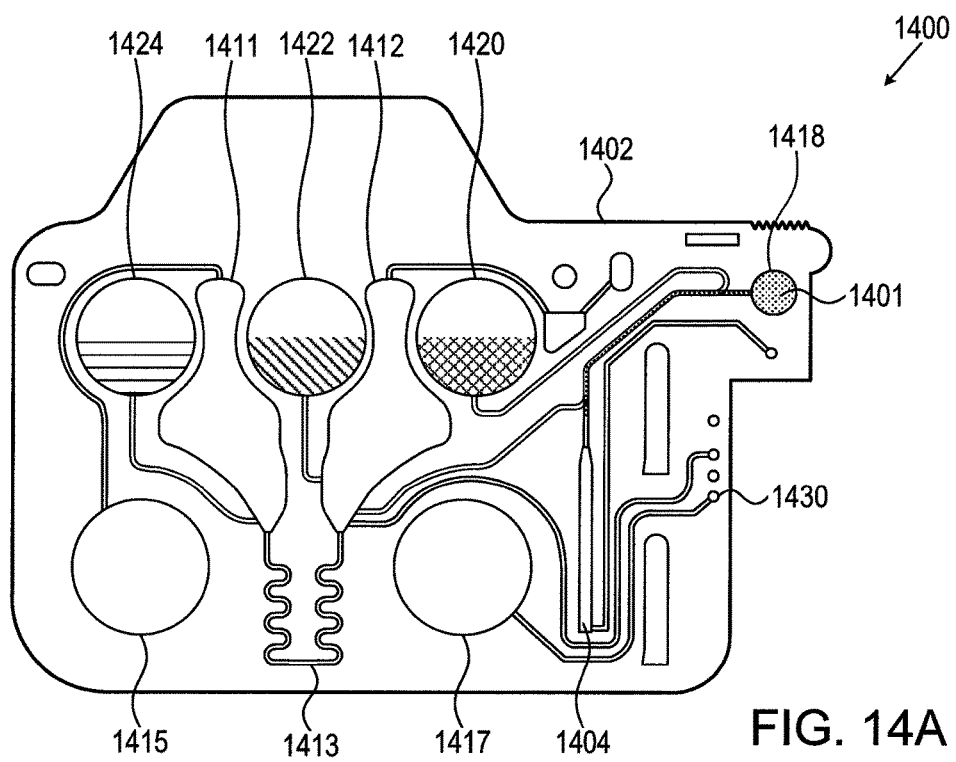
Figure 14B:
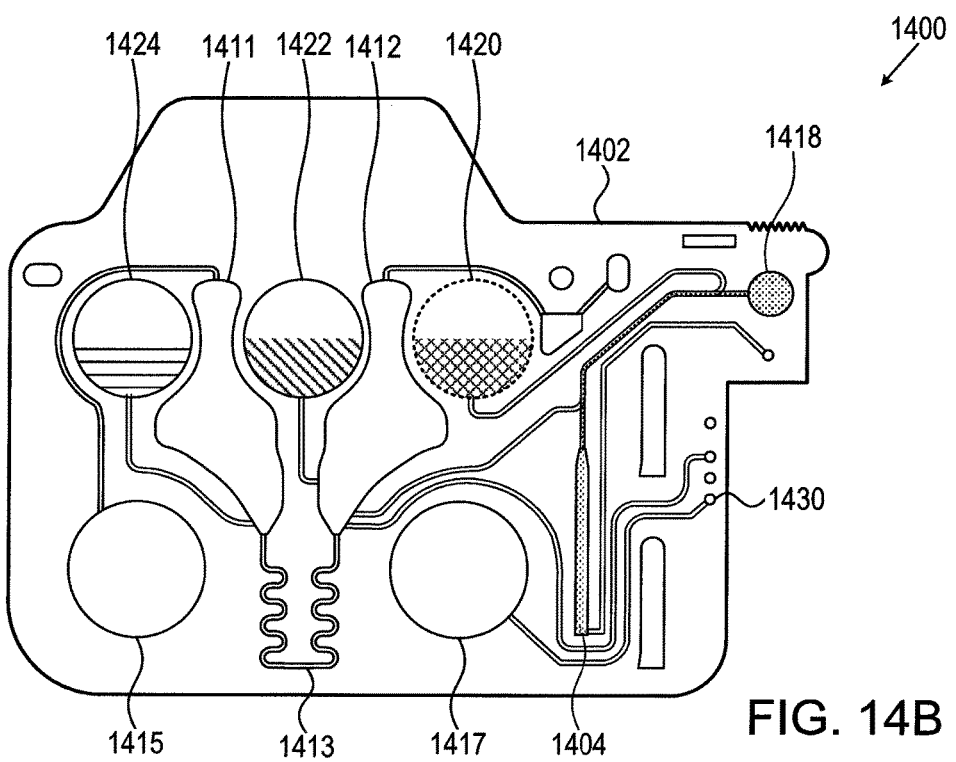
Figure 14C:
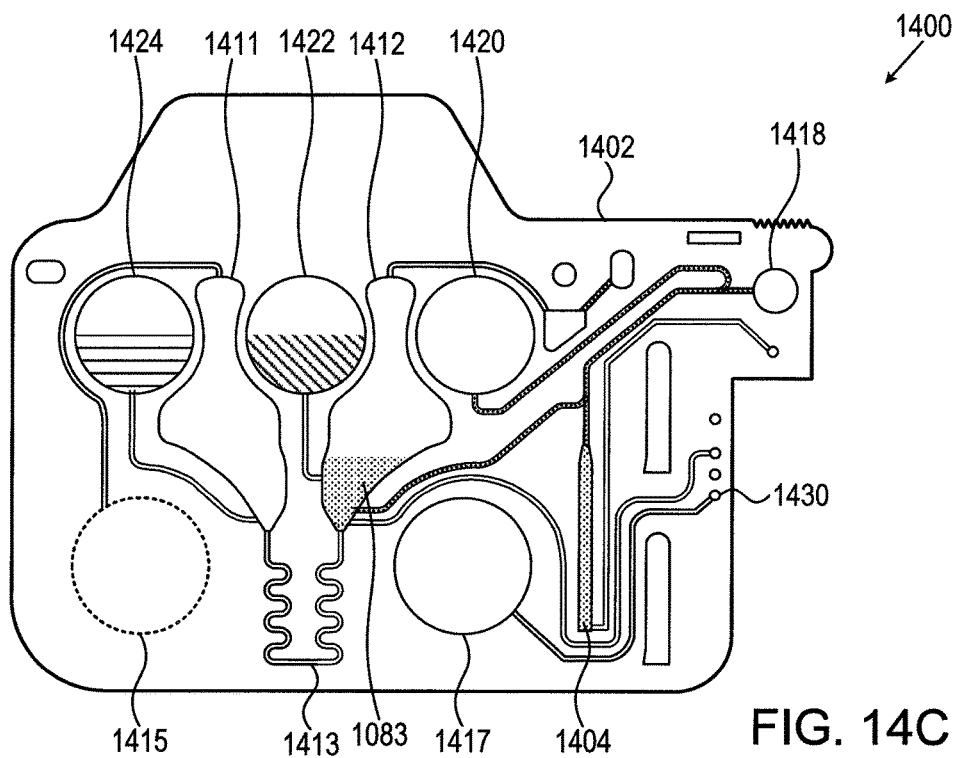
Figure 14D:
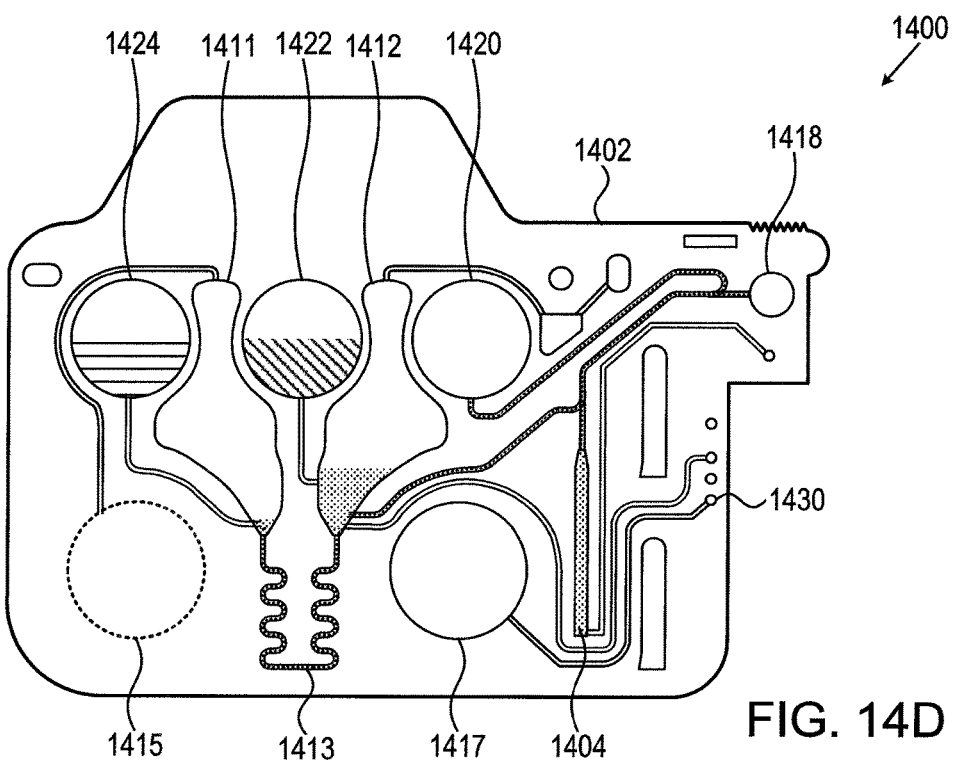
Figure 14E:
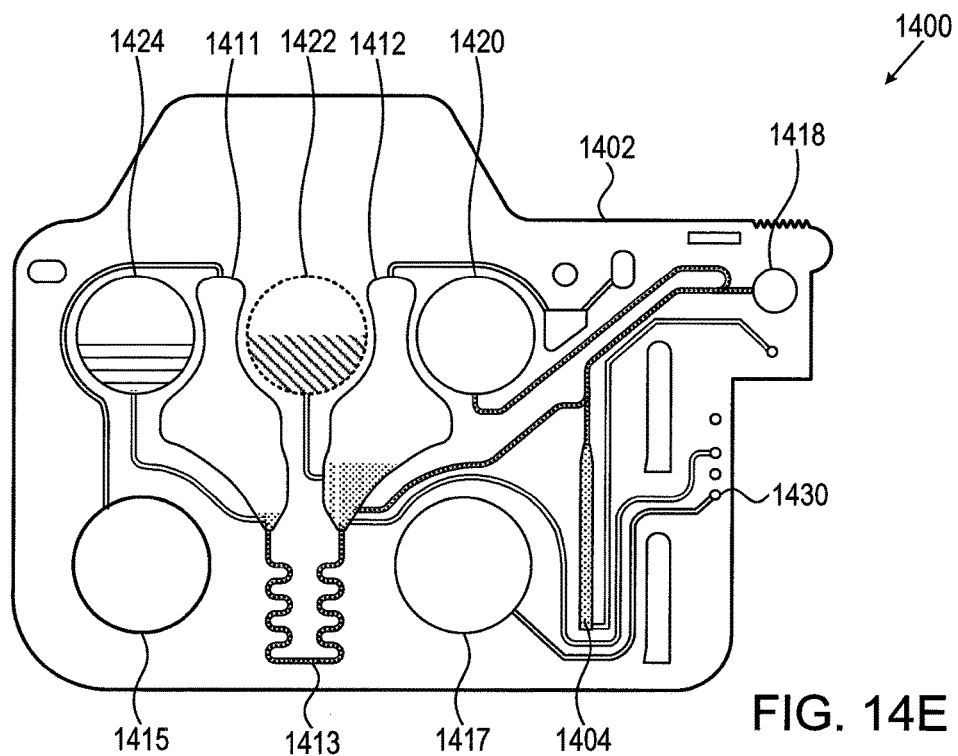
Figure 14F:
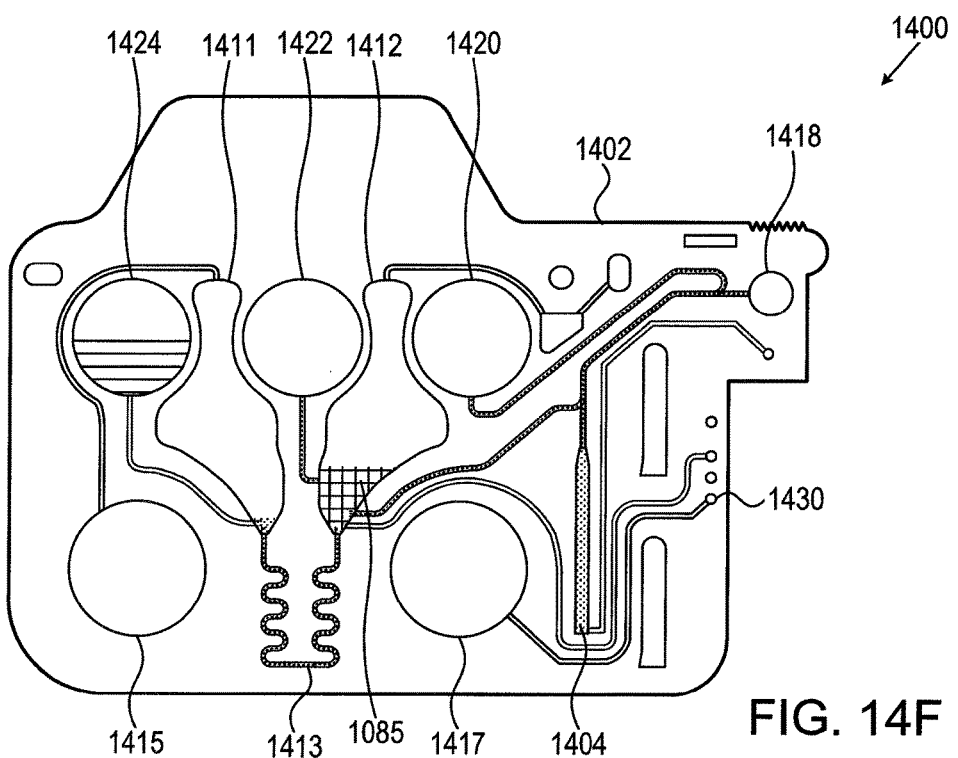
Figure 14G:
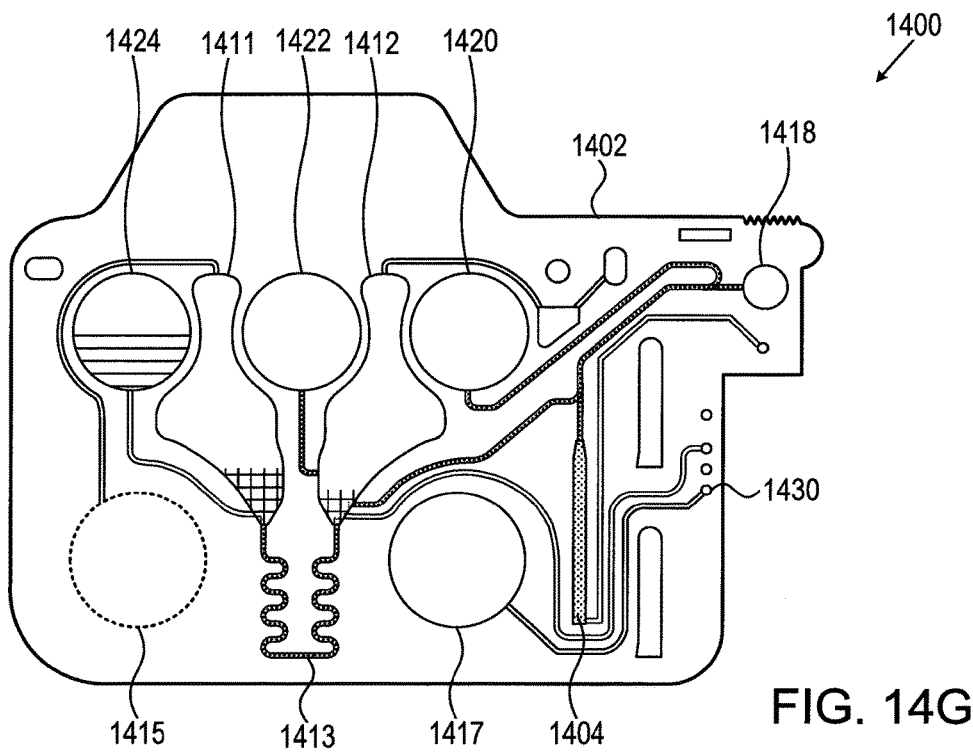
Figure 14H:
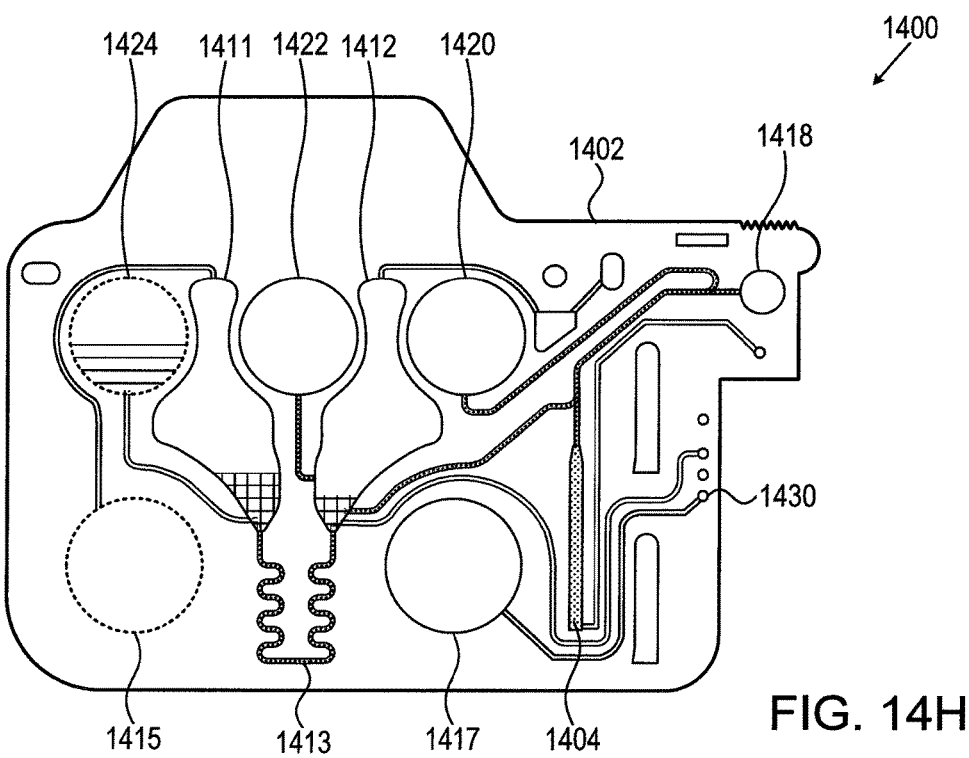
Figure 14I:
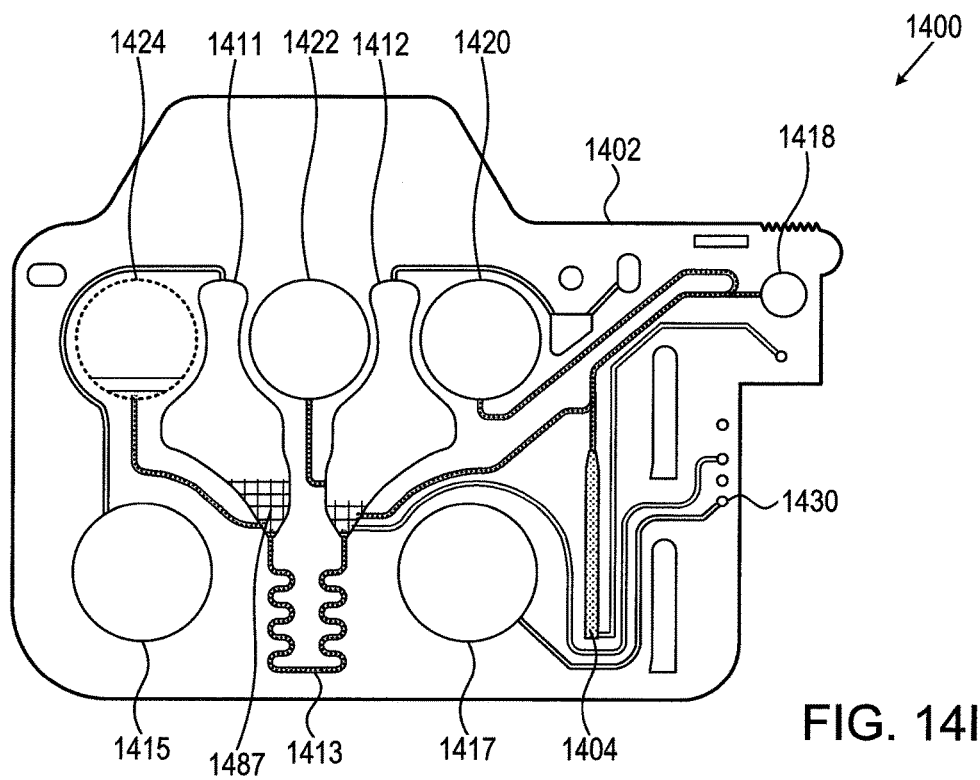
Figure 14J:
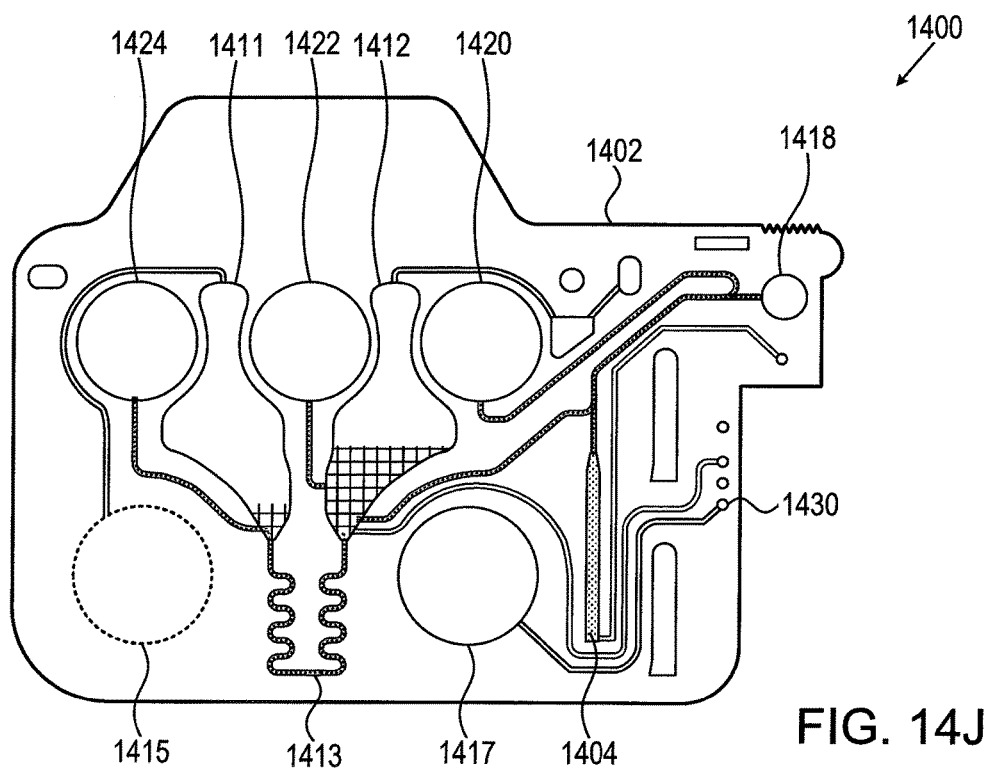
Figure 14K:
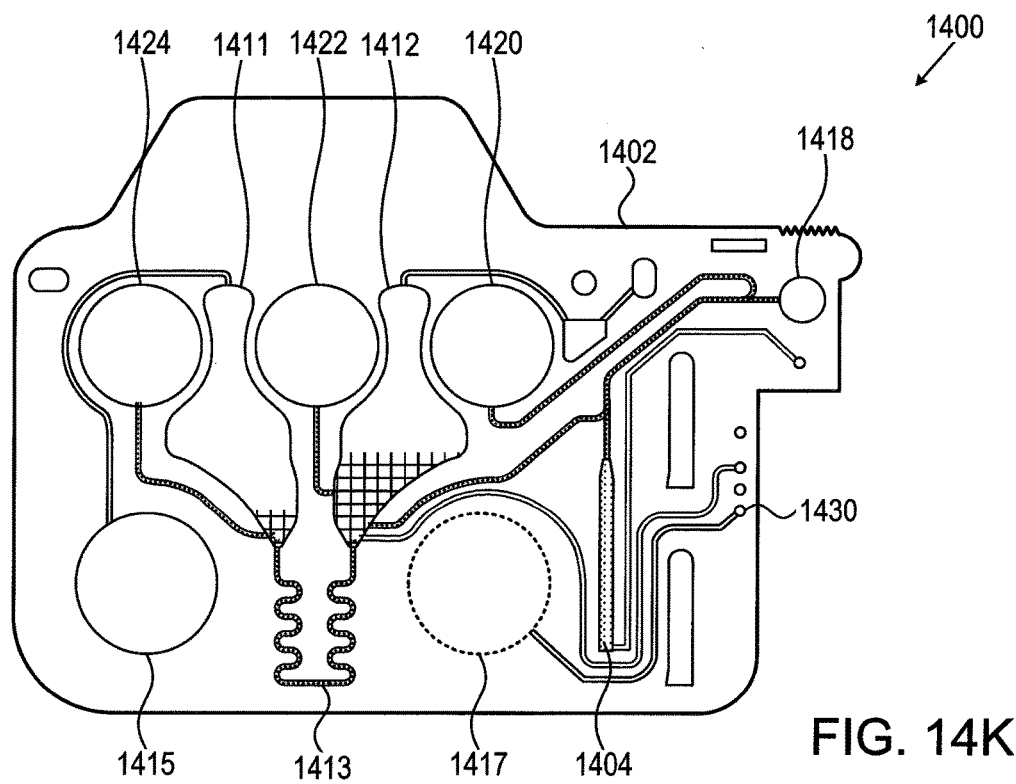
Figure 14L:
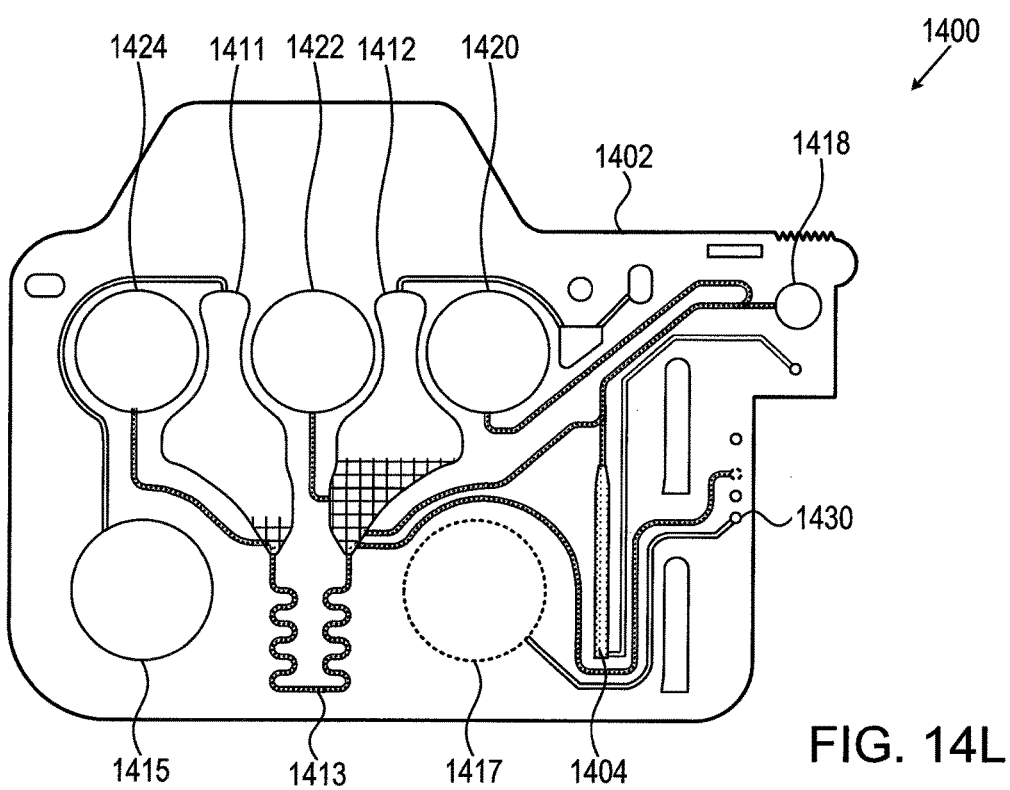
Figure 14M:
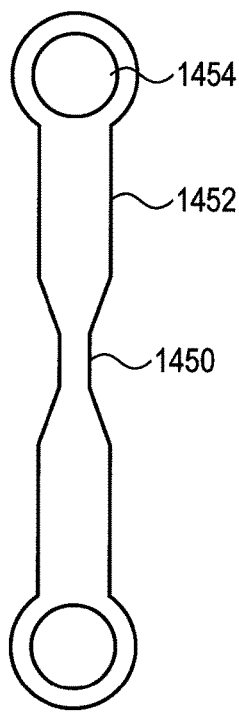
Figure 14N:
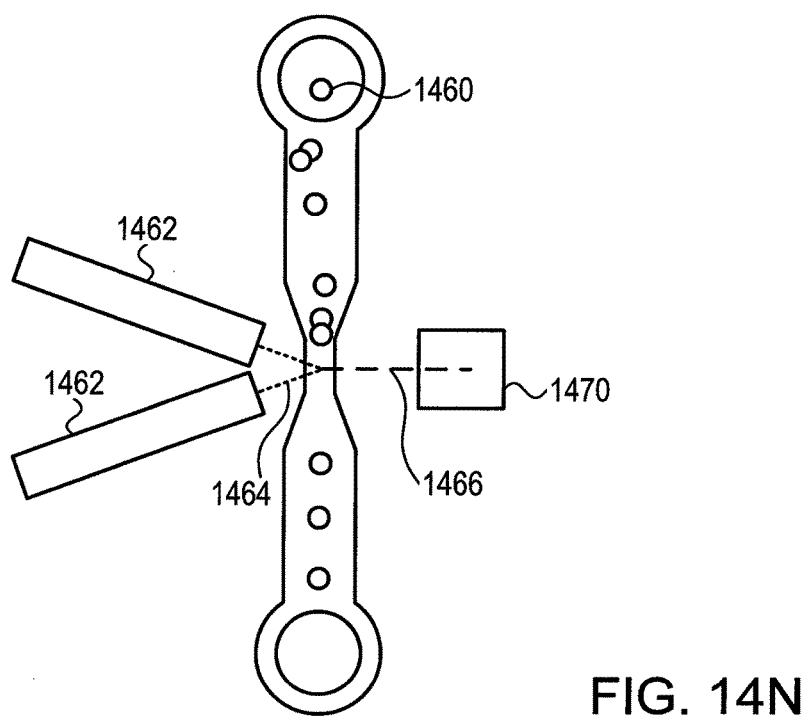
Figure 14O:
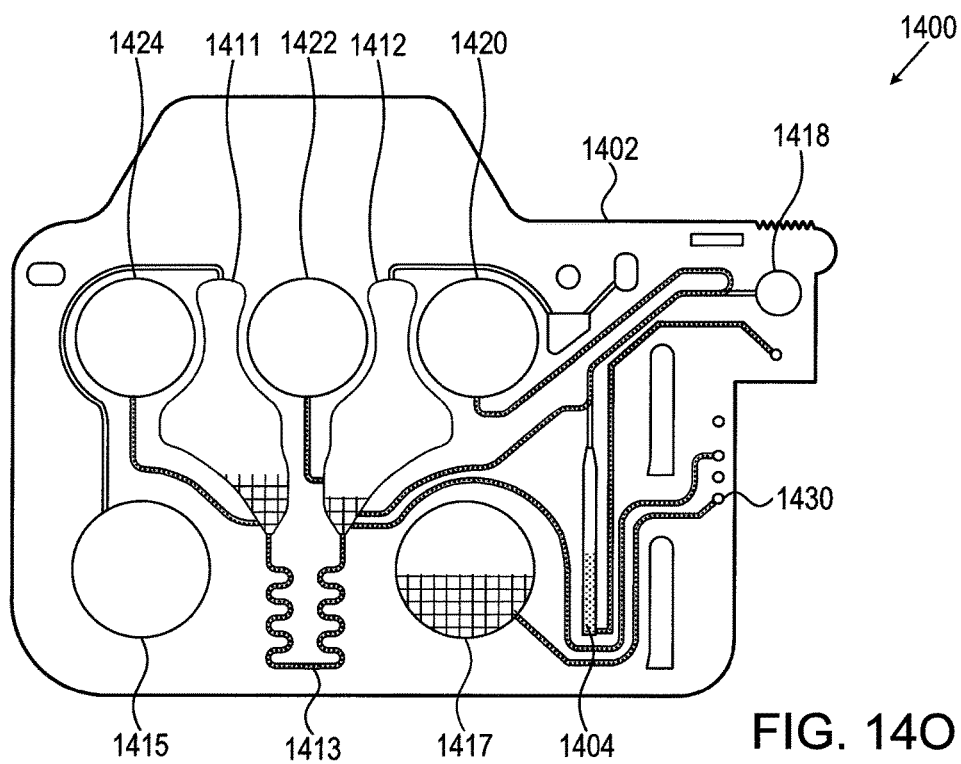
Figure 15:
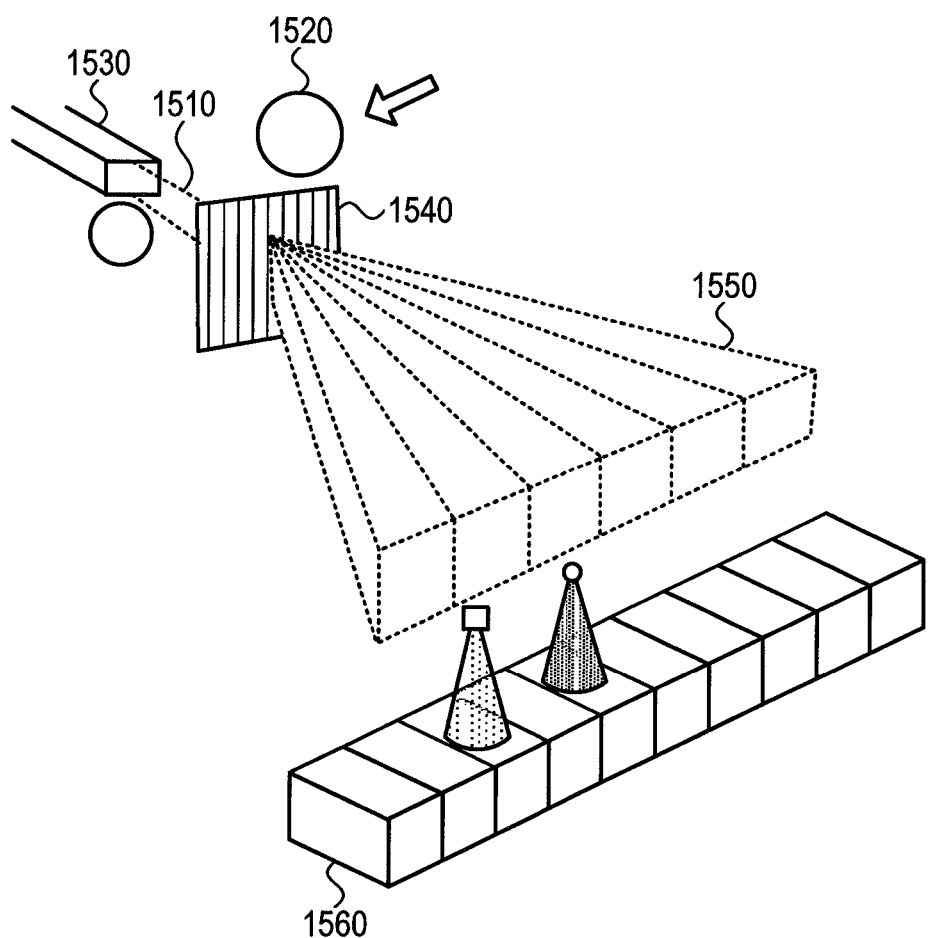
Figure 16:
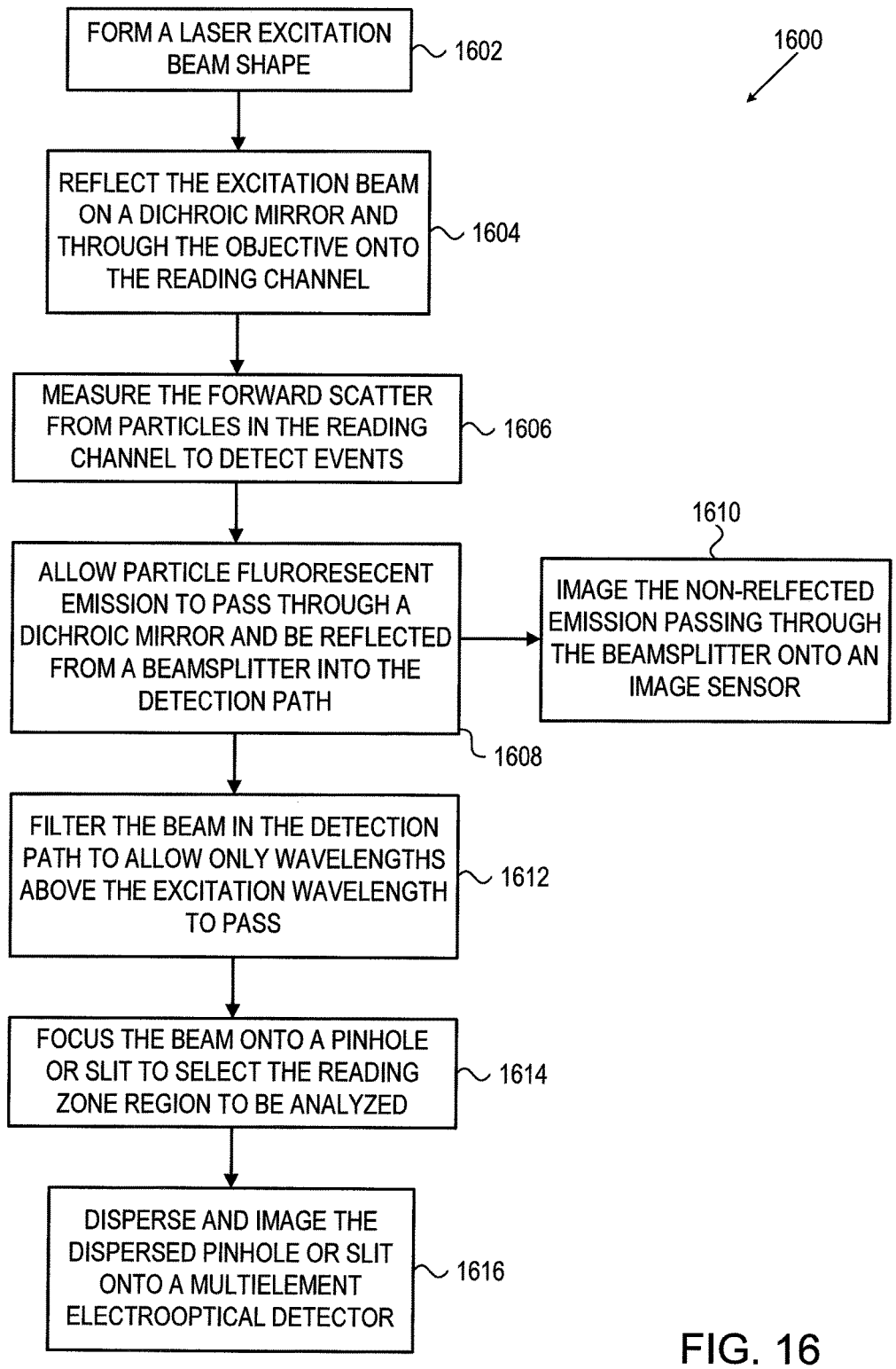
Figure 17A:
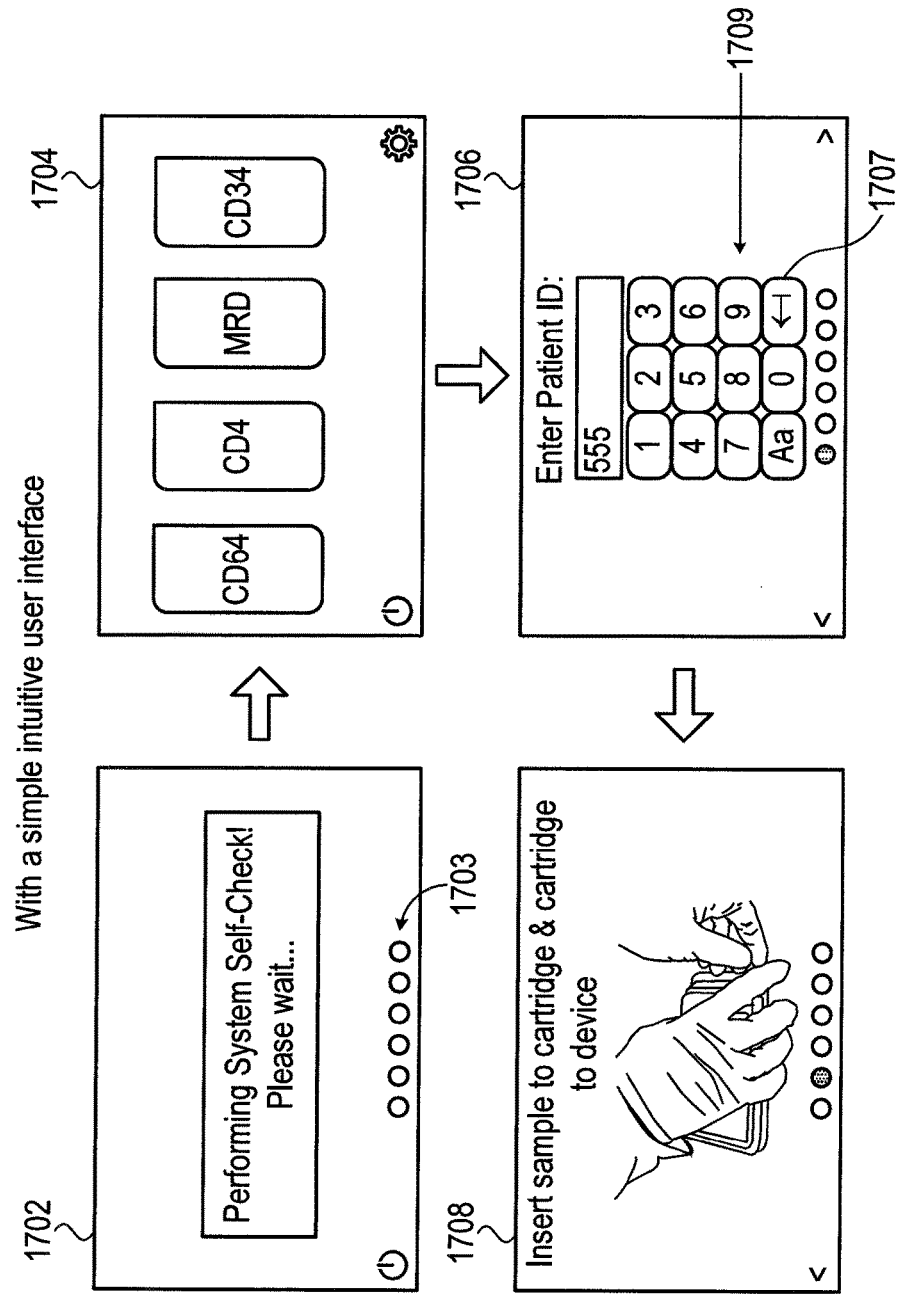
Figure 17B:
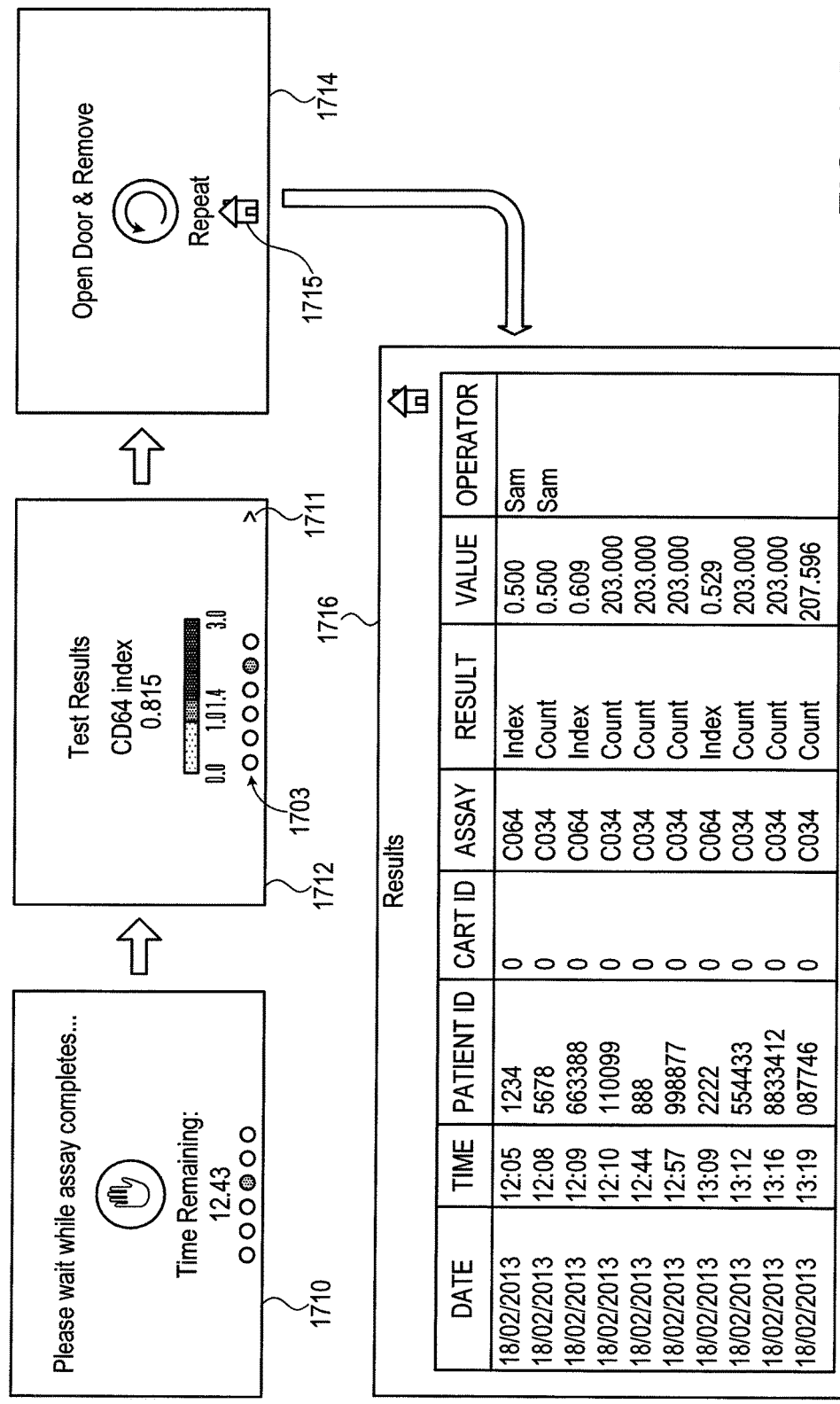
Figure 18:
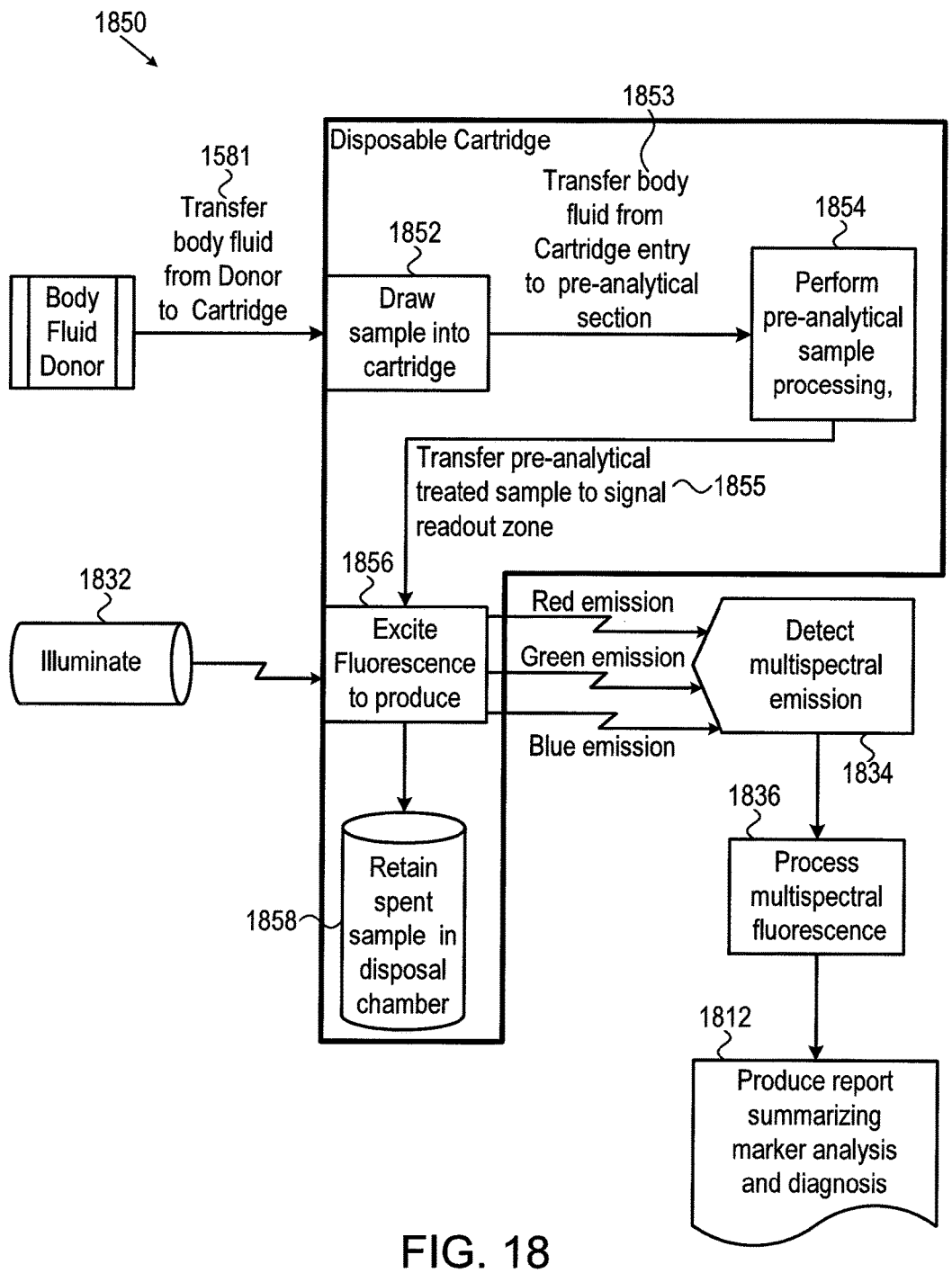
Figure 19A:
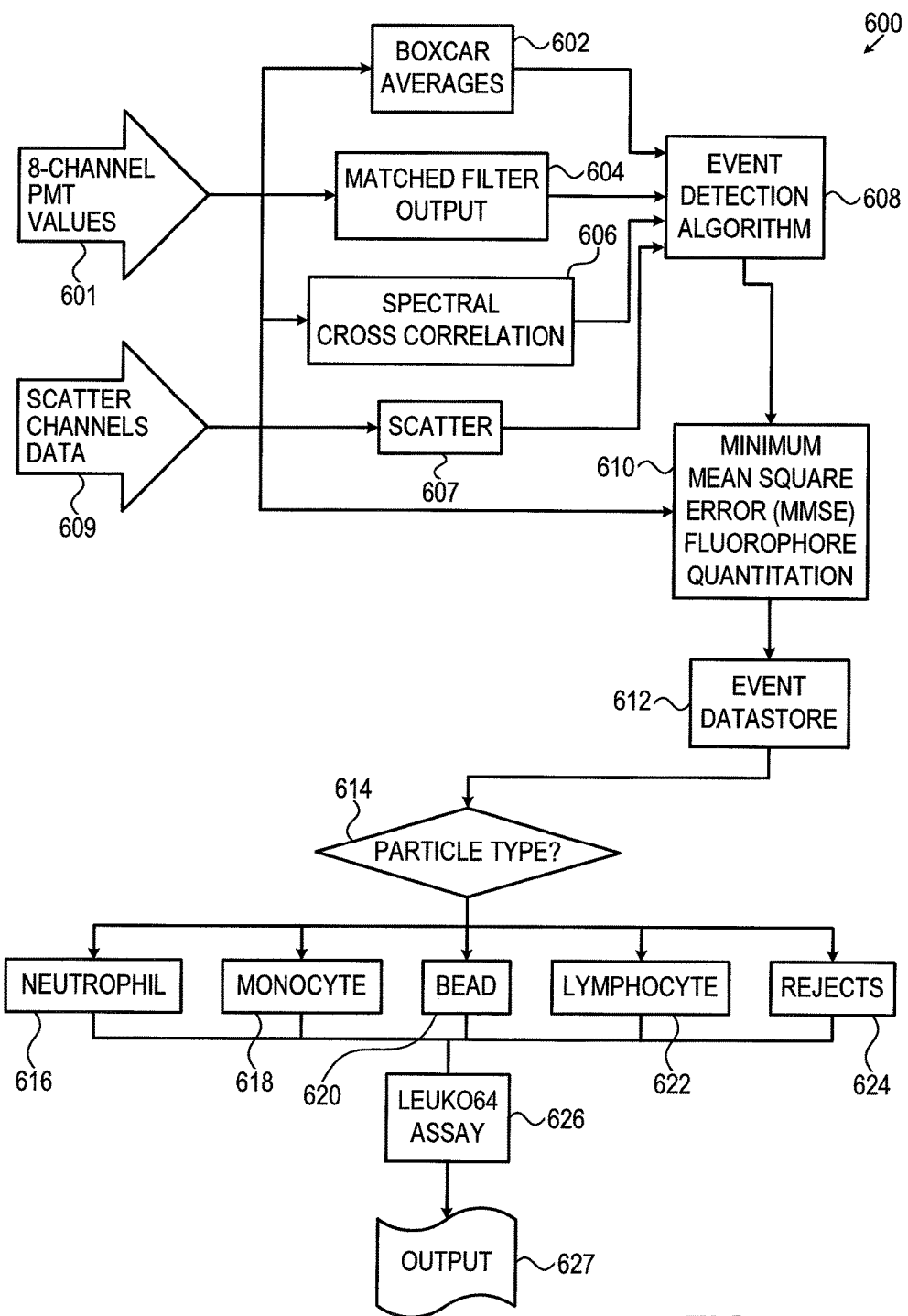
Figure 19B:
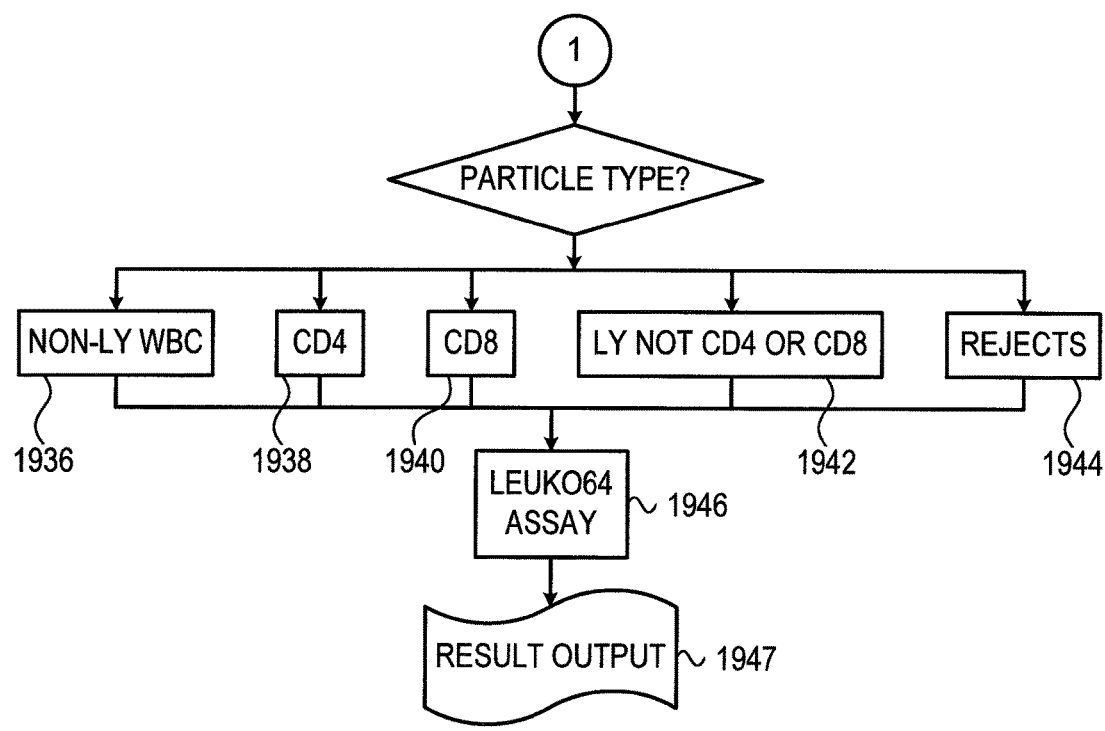
Figure 20A:
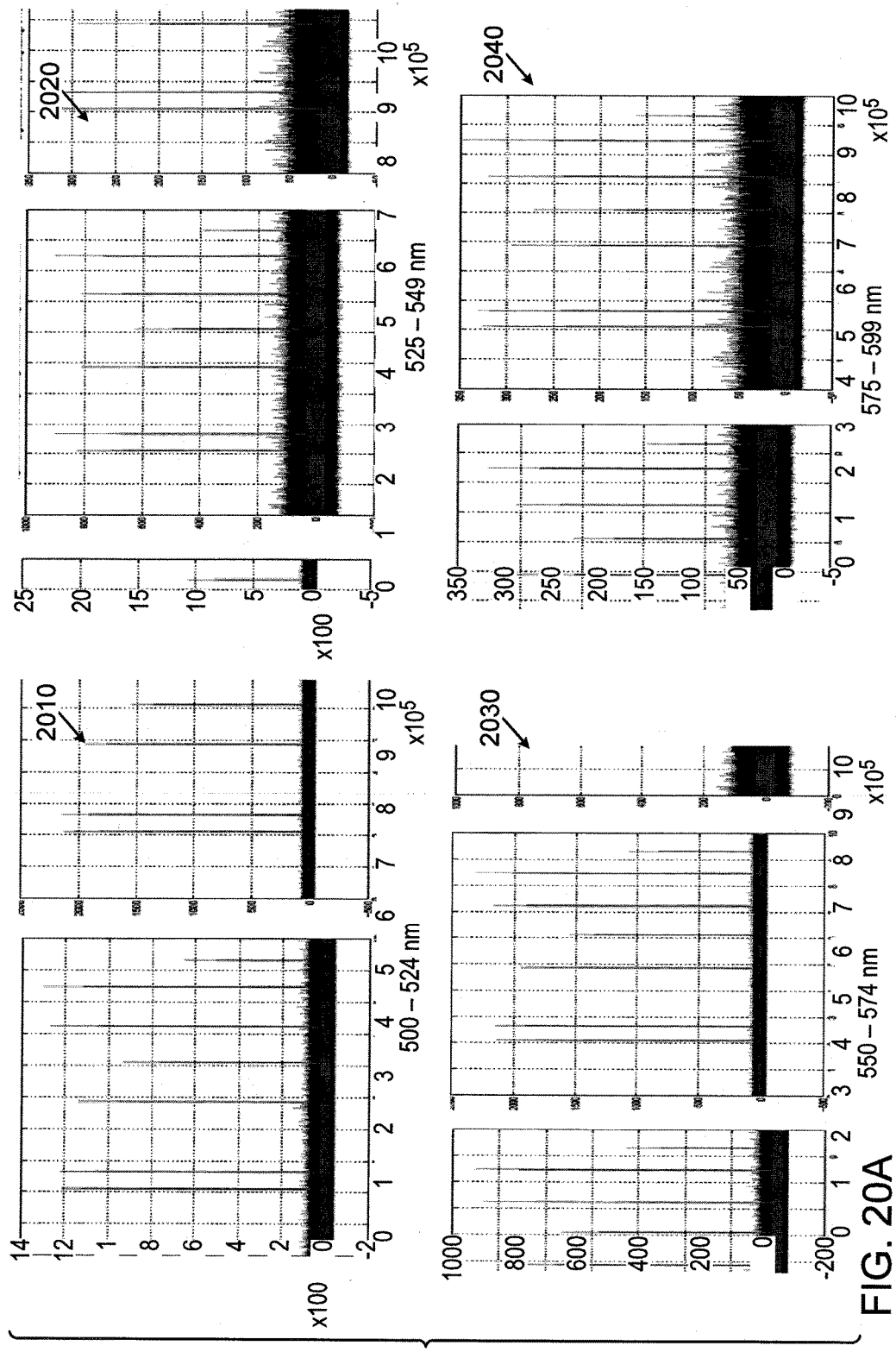
Figure 20B:
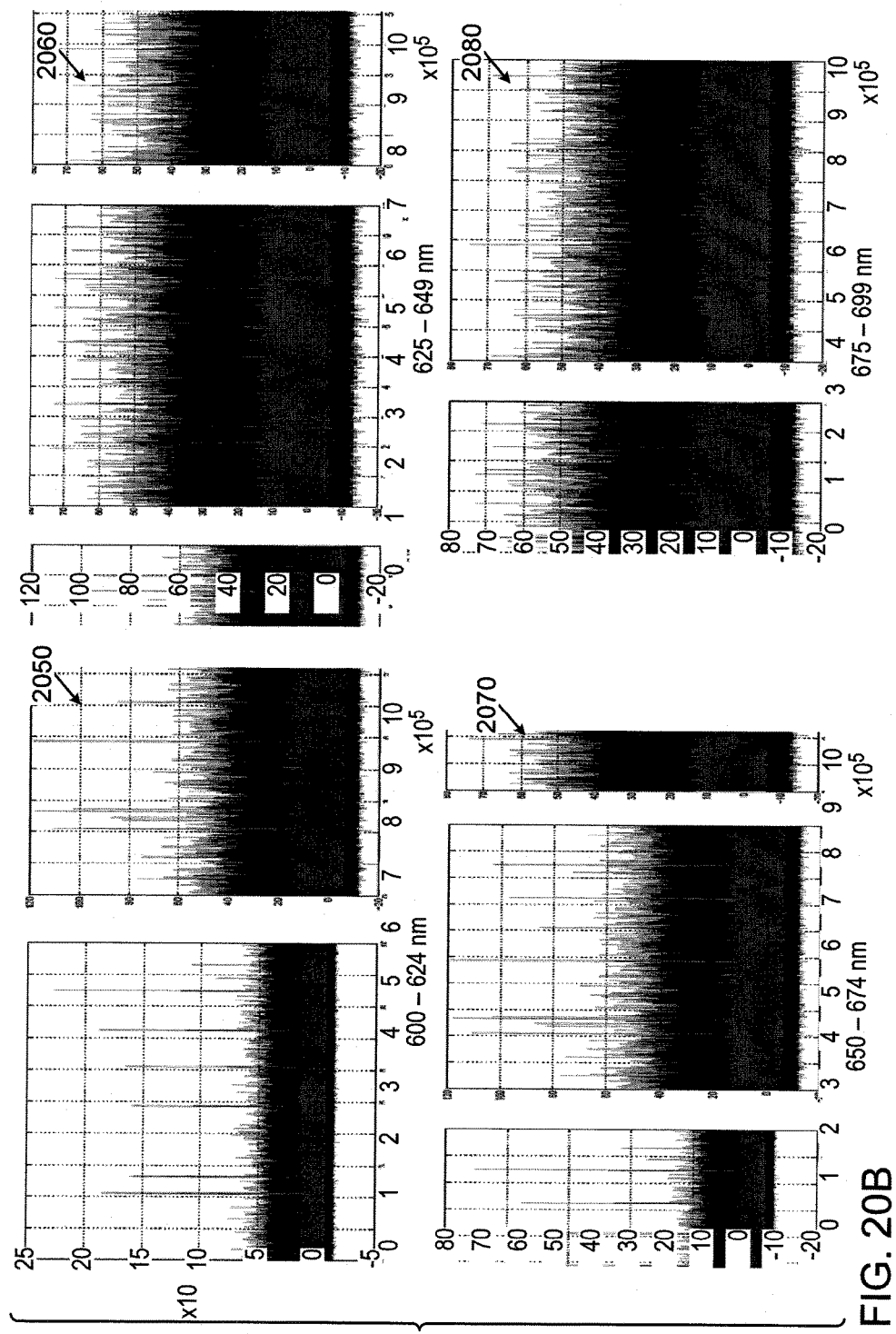
Figure 22A:
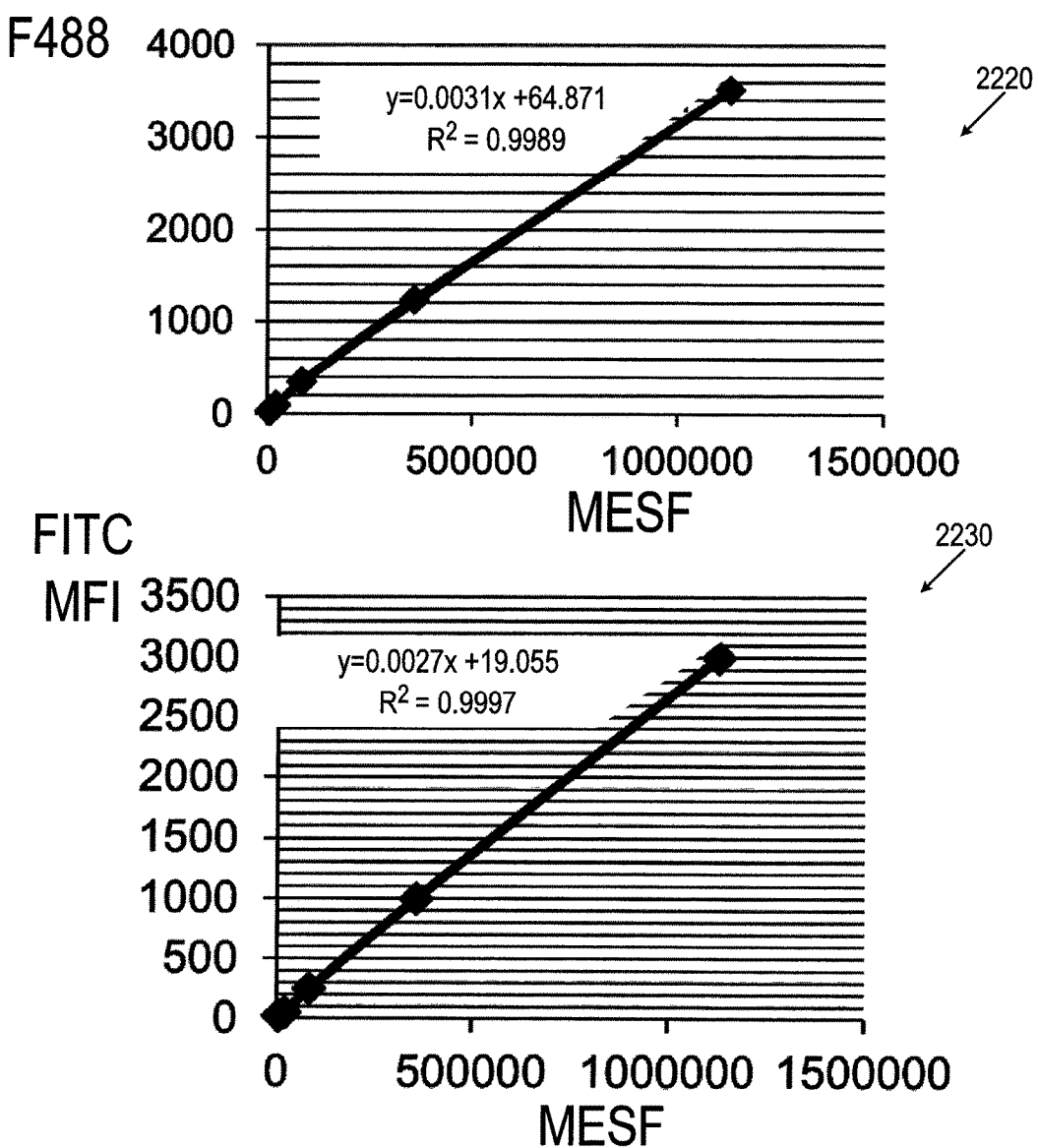
Figure 23A:
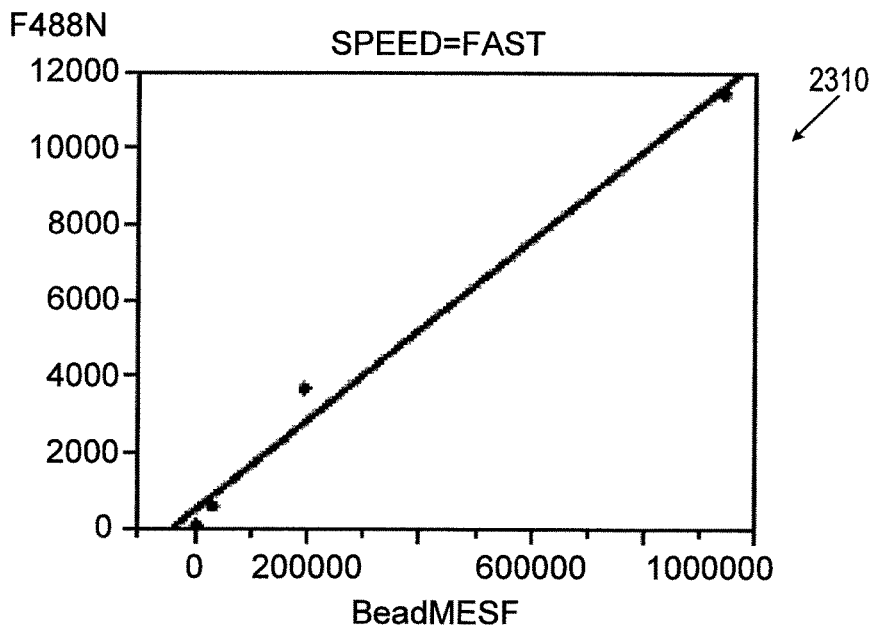
Figure 23B:
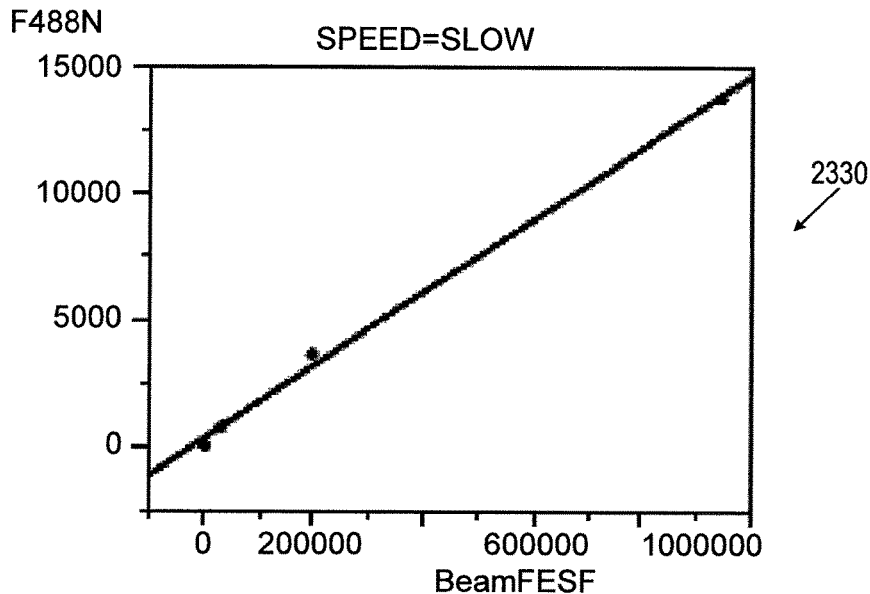
Figure 24:
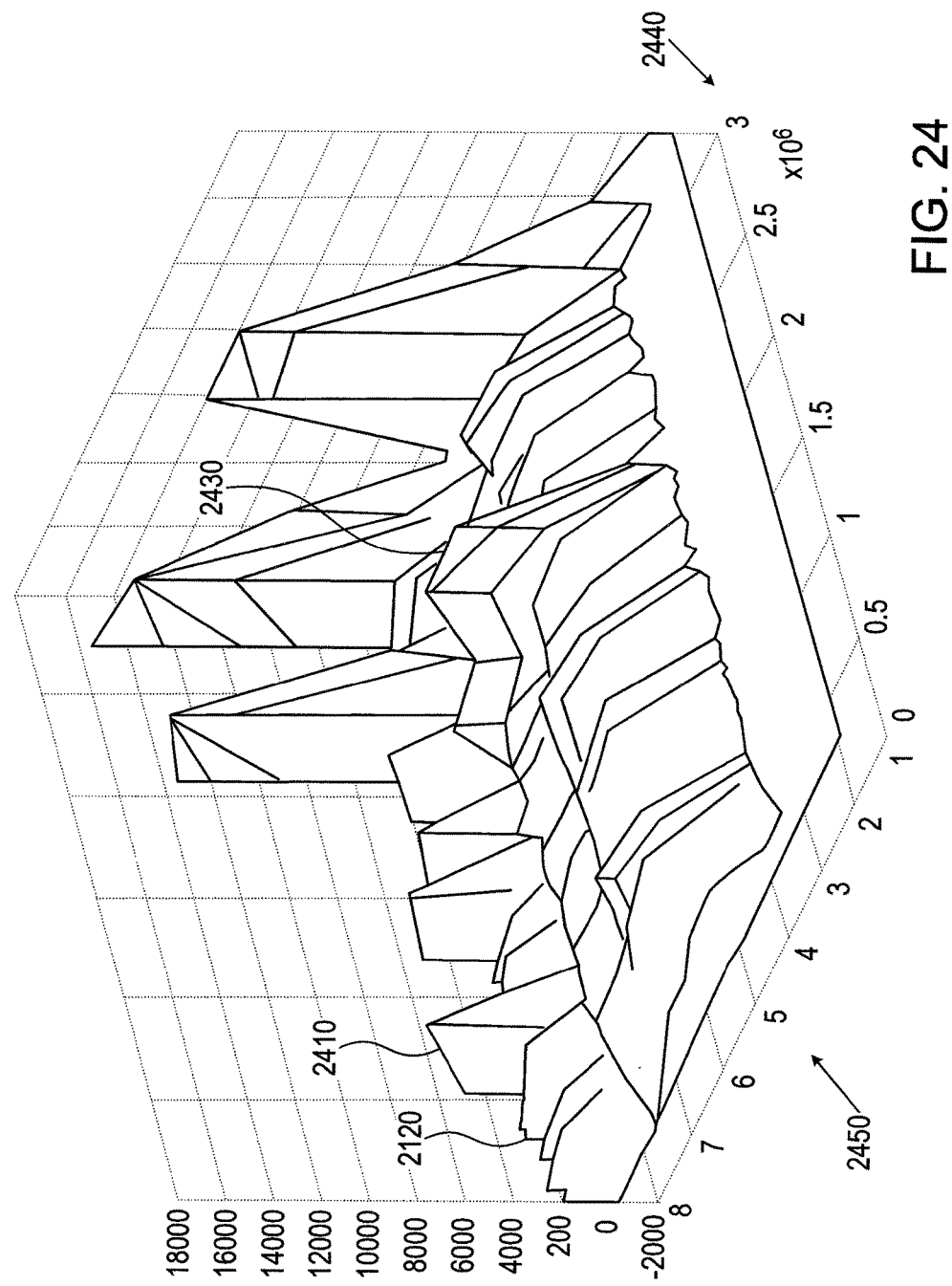
Figure 25:
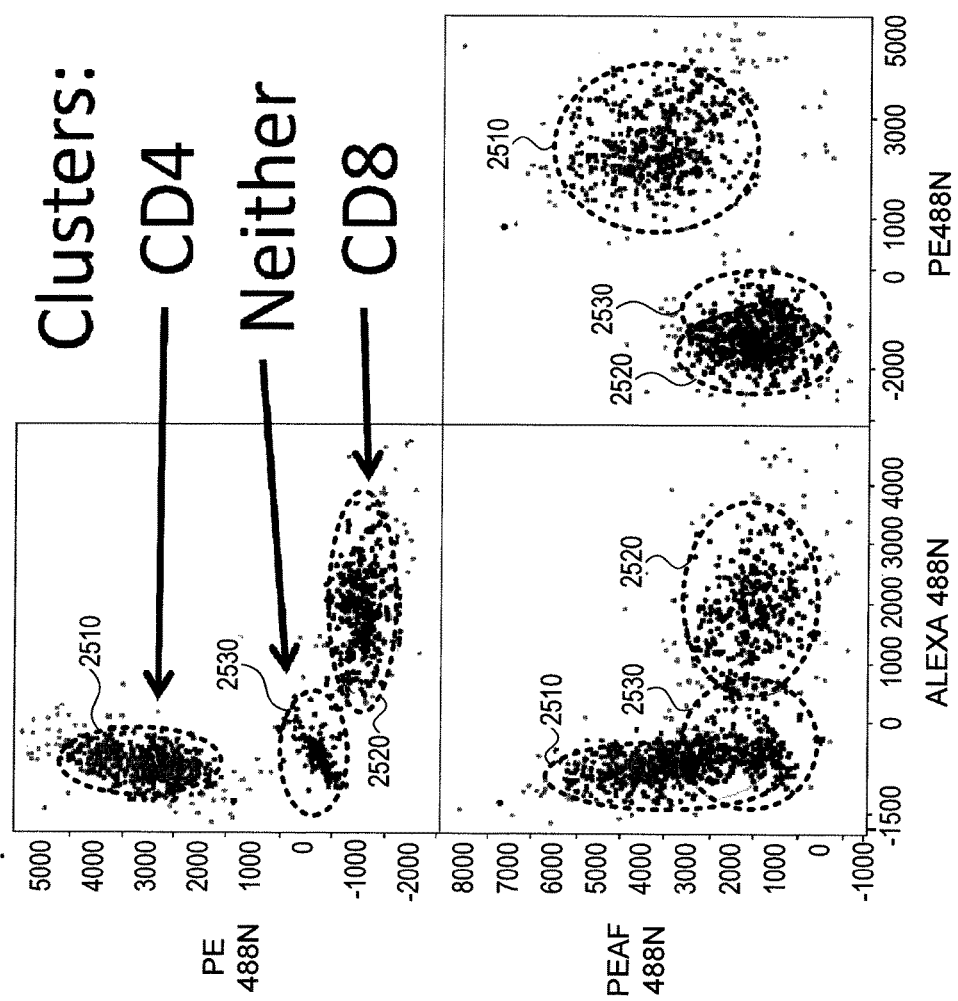
Figures 26, 27:
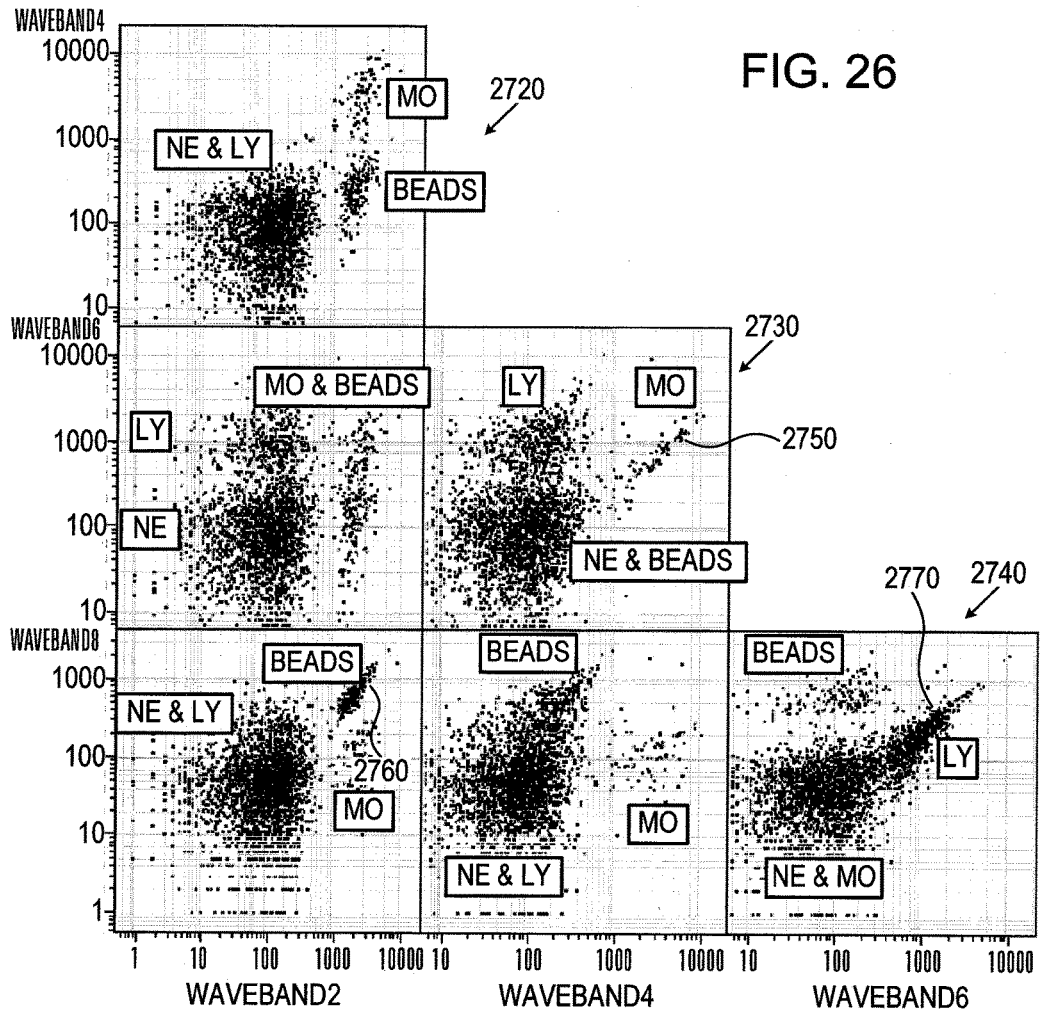

FIG. 9A is a schematic view of a sampling cartridge of the system of FIG. 1A, in accordance with an embodiment of the present invention;

FIG. 9B shows a schematic view of disposable cartridge in flow-cytometer device, in accordance with an embodiment of the present invention;

FIG. 10 is a simplified flowchart of a method for rapid determination of a medical condition, in accordance with an embodiment of the present invention;

FIG. 11 is a three-dimensional graph showing the optical output over time of reference beads (RM) relative to a sample from a human patient (PMN), in accordance with an embodiment of the present invention;

FIGS. 12A-12C show graphs of optical outputs over time of the reference beads and the sample from a human patient, in accordance with an embodiment of the present invention;

FIG. 13A is an outer side view of a cartridge assembly, in accordance with an embodiment of the present invention;

FIG. 13B is an inner side view of a cartridge assembly, in accordance with an embodiment of the present invention;

FIG. 14A-14O show a sequence of process events in a cartridge assembly, in accordance with an embodiment of the present invention;

FIG. 15 is a schematic illustration of a micro flow spectrometer reading, in accordance with an embodiment of the present invention;

FIG. 16 is a flow chart of a method for optical processing, in accordance with an embodiment of the present invention;

FIGS. 17A-17B are schematic illustrations of steps of use of a graphical user interface, in accordance with an embodiment of the present invention;

FIG. 18 is a cartridge block diagram showing a role of signal processing software, in accordance with an embodiment of the present invention;

FIG. 19A is a flow chart of an algorithm for biological detection, in accordance with an embodiment of the present invention;

FIG. 19B is a flow chart of an algorithm for biological detection, in accordance with an embodiment of the present invention;

FIGS. 20A-20B shows bandwidth leveled and smoothed arrays, in accordance with an embodiment of the present invention;

FIGS. 21A-21B are schematics for solving a fluor decomposition of an observed signal, in accordance with an embodiment of the present invention;

FIGS. 22A-22B is a graphical comparison of system performance with FITC beads with MESF detection versus FACS, in accordance with an embodiment of the present invention;

FIGS. 23A-23B show graphical displays of linearity of system performance with Alexa 488 MESF, in accordance with an embodiment of the present invention;

FIG. 24 is a three-dimensional graph showing the optical output over time of a CD4-CD8 assay, in accordance with an embodiment of the present invention;

FIG. 25 is a graphical display showing a cluster analysis of a CD4-CD8 assay, in accordance with an embodiment of the present invention;

FIGS. 26-27 are graphical displays showing cluster separations of the cluster analysis of FIG. 25, in accordance with an embodiment of the present invention; and FIG. 28 is a comparison table of different array options, in accordance with an embodiment of the present invention.

Figure 29A:
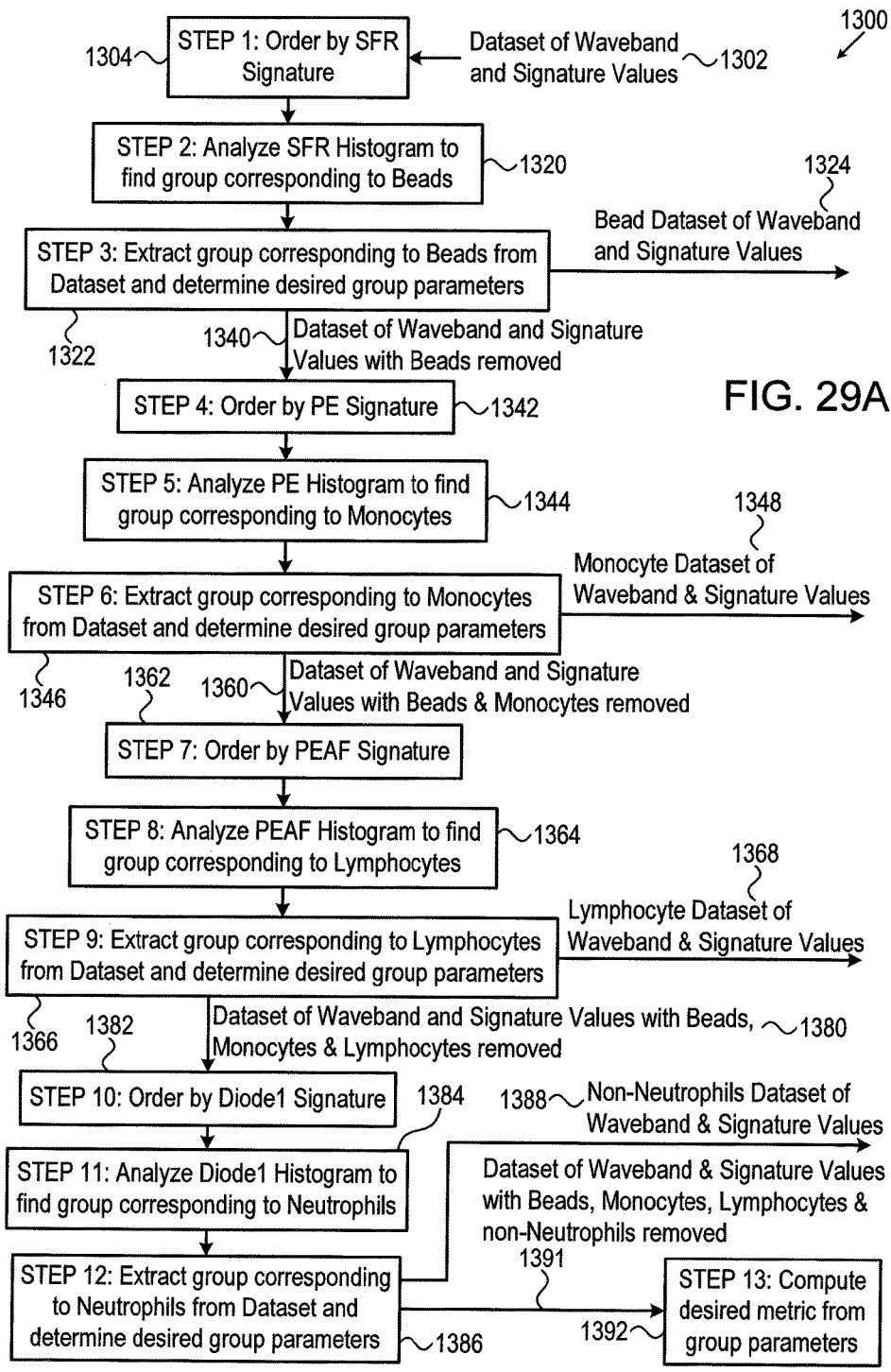
Figure 29B:
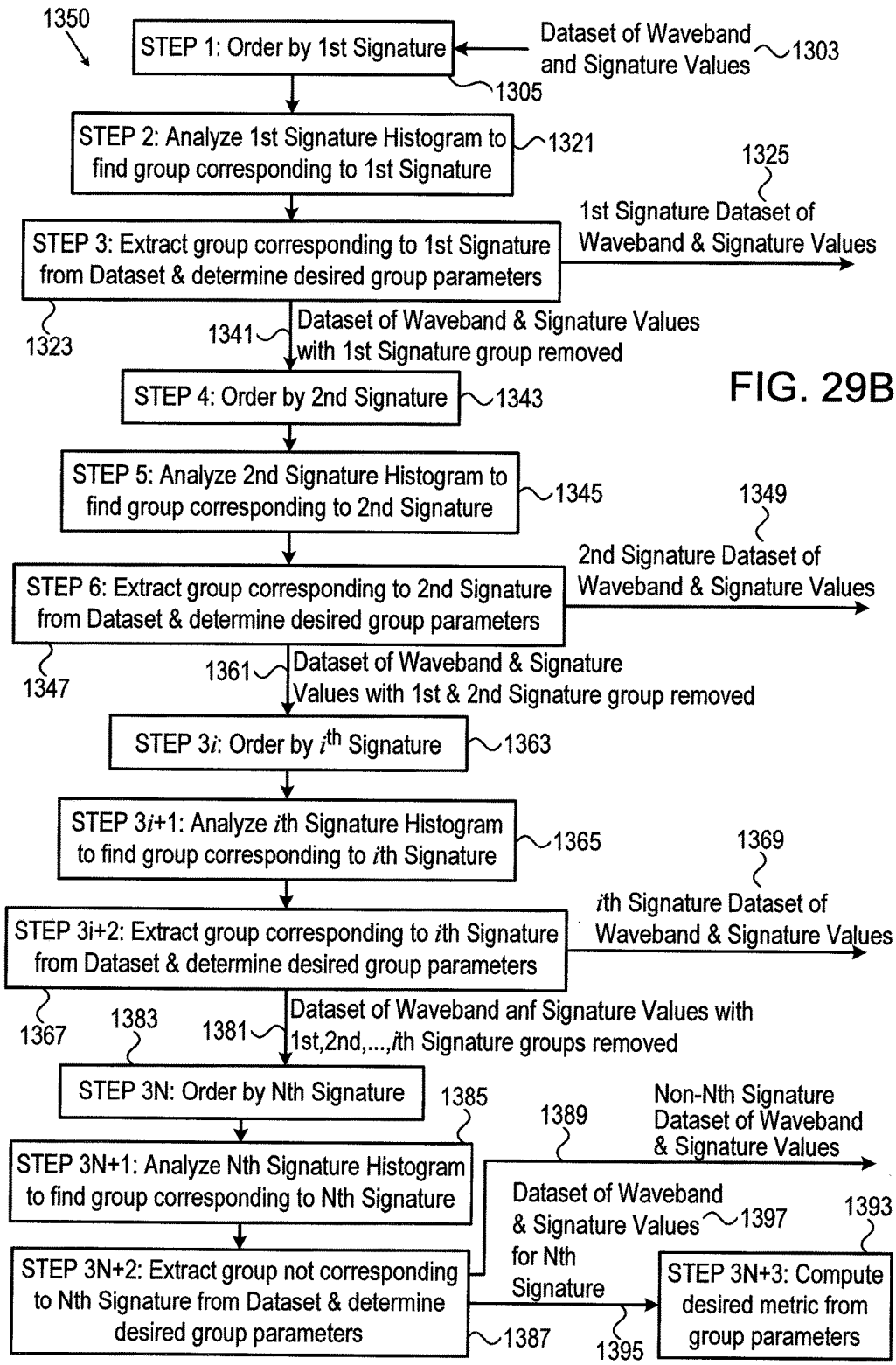
Figure 31A:
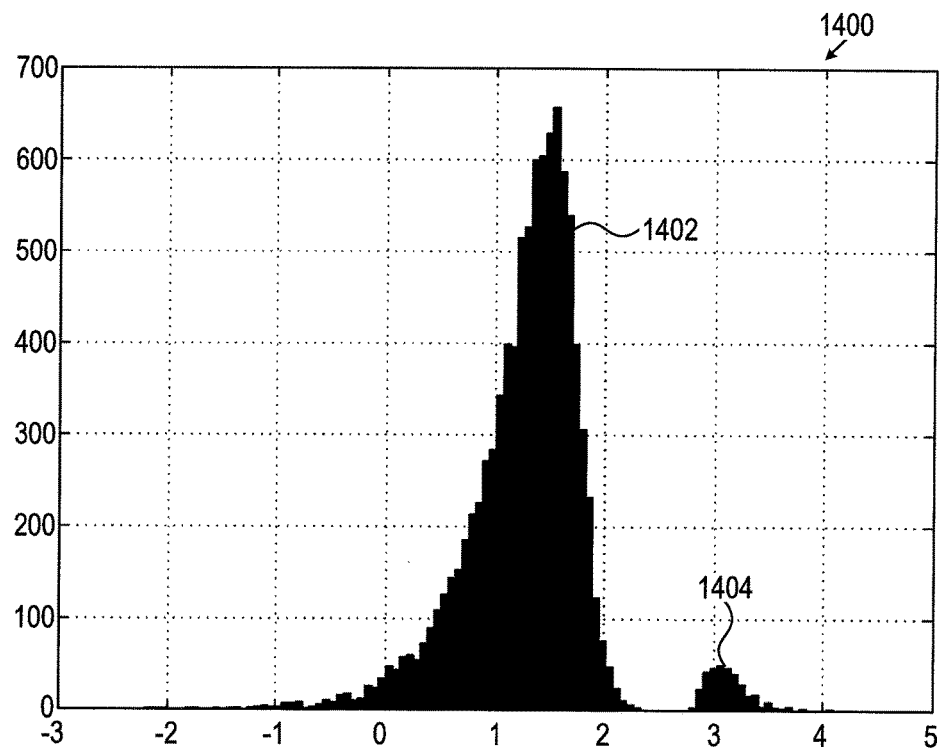
Figure 31B:
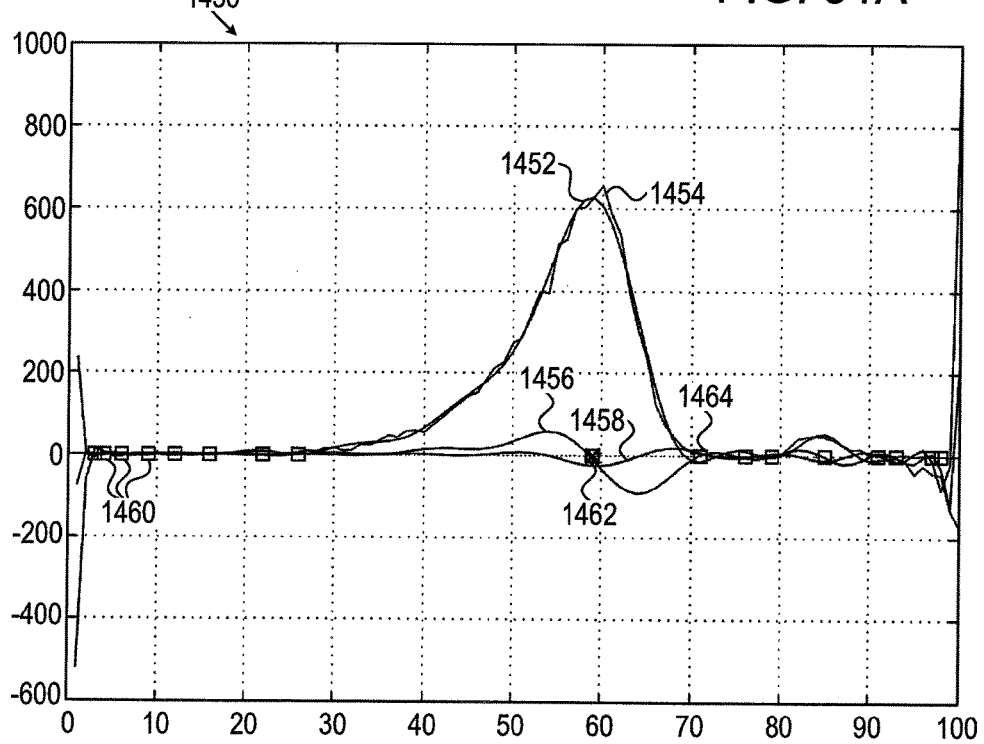
Figure 32A:
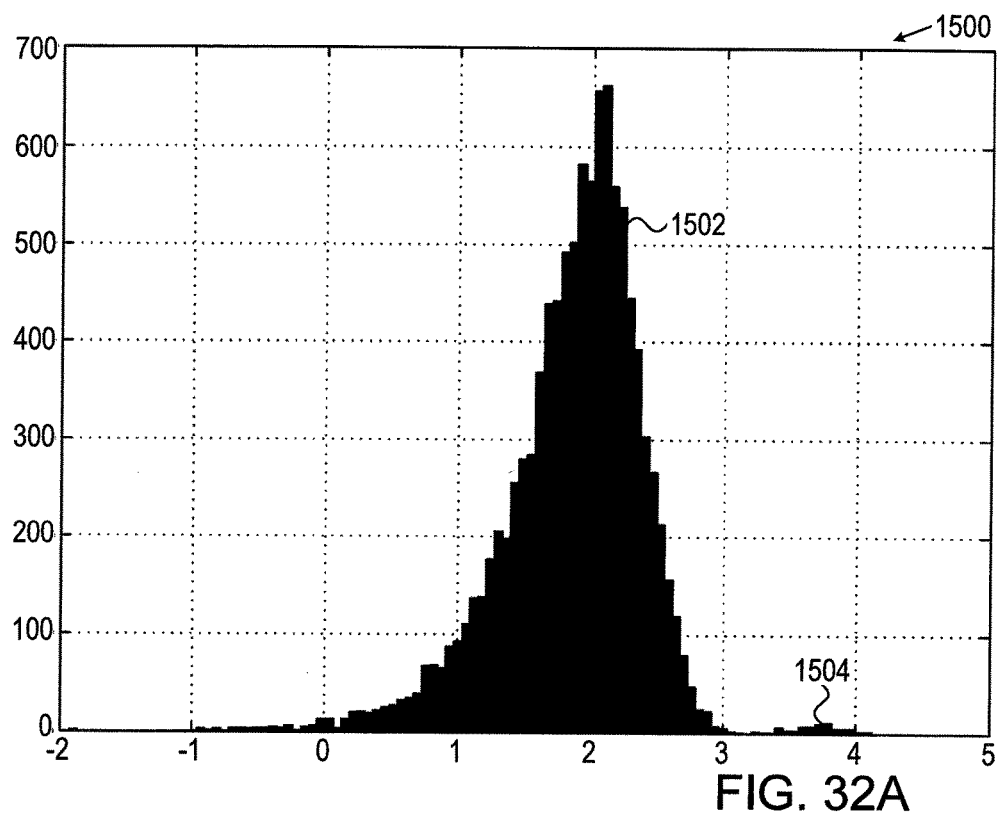
Figure 32B:
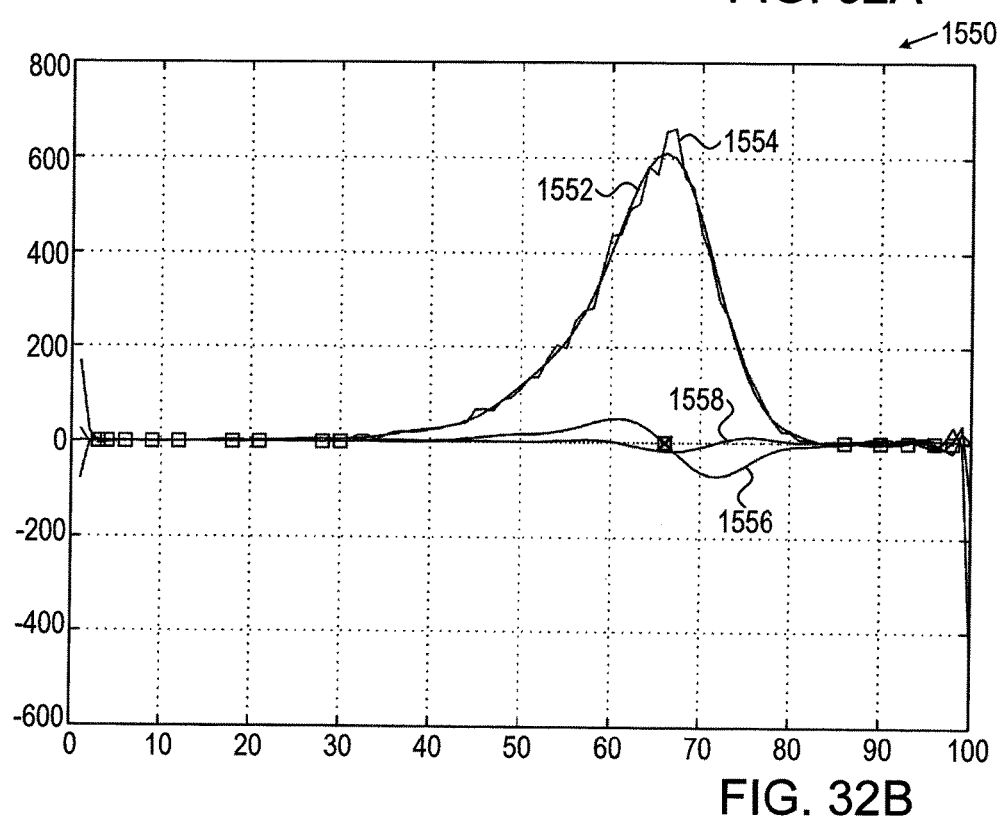
Figure 33A:
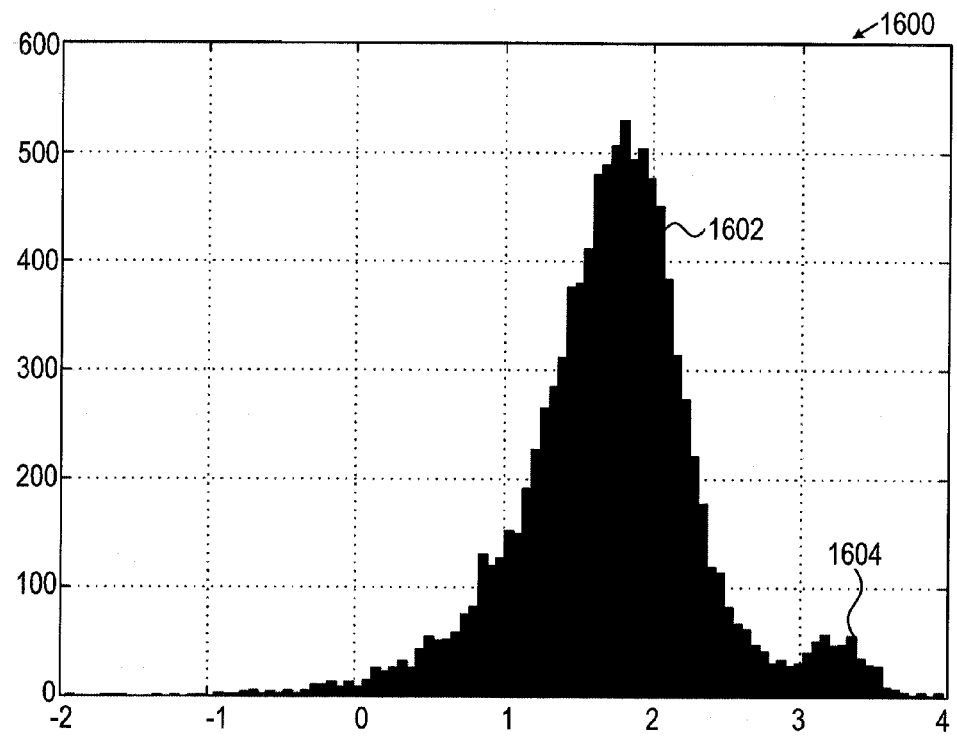
Figure 33B:
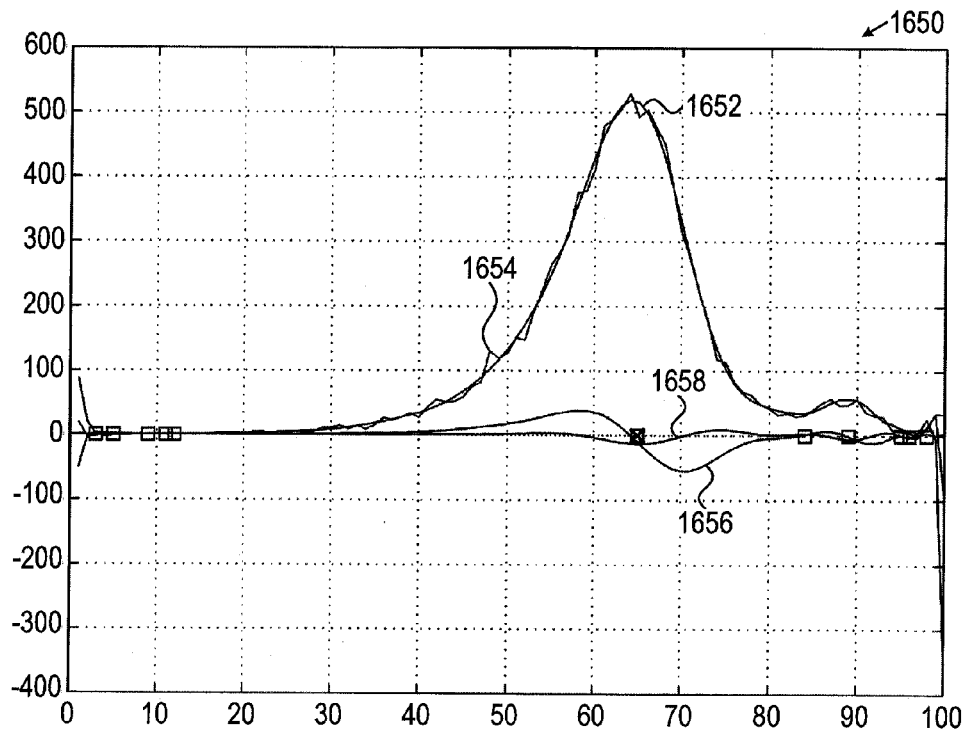

FIG. 29A is a flowchart of a specific implementation of an algorithm for selecting groups of data from a scatterplot, in accordance with an embodiment of the present invention;

FIG. 29B is a flowchart of a general implementation of an algorithm for selecting groups of data from a scatterplot, in accordance with an embodiment of the present invention;

FIG. 30 is a scatterplot matrix of the four fluors signatures showing four distinct event groups, in accordance with an embodiment of the present invention;

FIG. 31A is a histogram of data of Starfire Red (SFR) signature values, in accordance with an embodiment of the present invention;

FIG. 31B is a plot of a polynomial and first and second derivative thereof of the histogram shown in FIG. 31A, in accordance with an embodiment of the present invention;

FIG. 32A is a histogram of data of PE488 signature values, in accordance with an embodiment of the present invention;

FIG. 32B shows a polynomial fitted to the histogram in FIG. 32A as well as corresponding first and second derivatives, in accordance with an embodiment of the present invention;

FIG. 33A is a histogram of data of PEAF488 signature values, in accordance with an embodiment of the present invention;

FIG. 33B shows a polynomial fitted to the histogram in FIG. 33A as well as corresponding first and second derivatives, in accordance with an embodiment of the present invention.

Figure 34A:
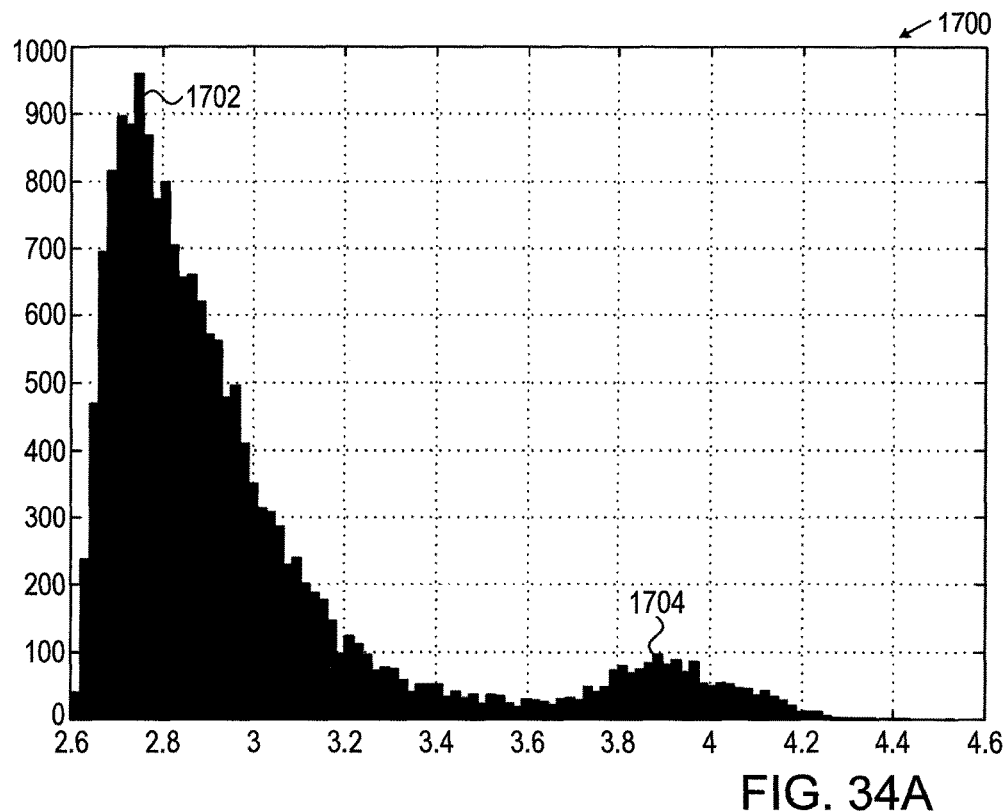
Figure 34B:
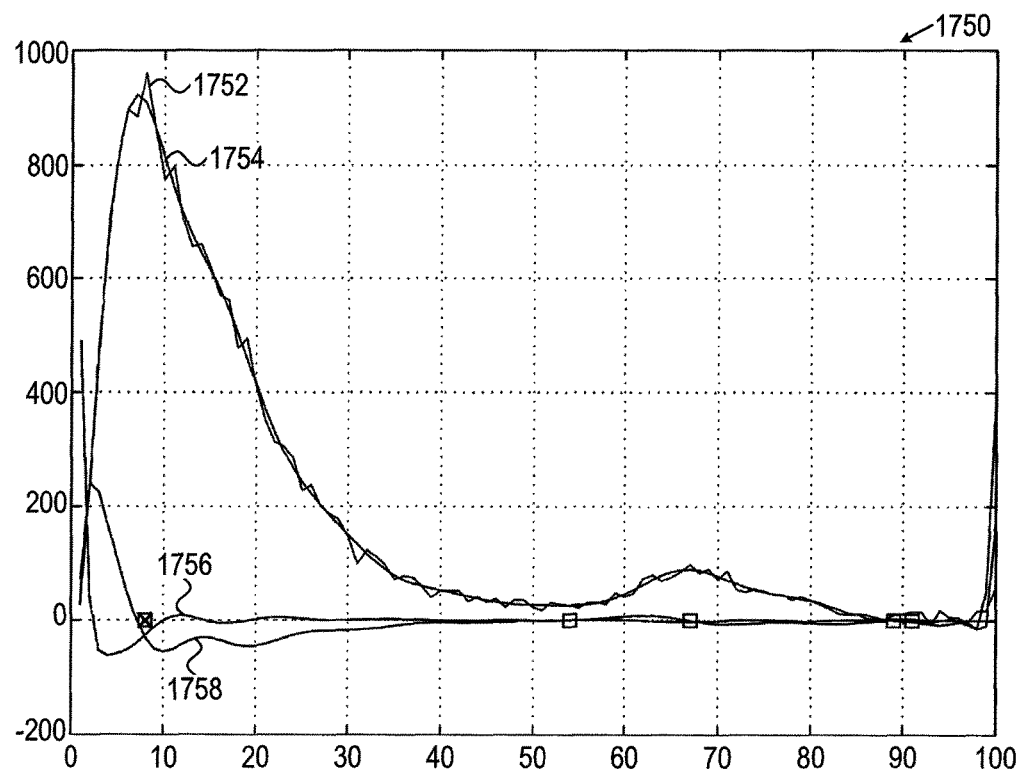

FIG. 34A is a histogram of data of Diode 1 channel signature values, in accordance with an embodiment of the present invention; and FIG. 34B shows the polynomial fitted to the histogram in FIG. 34A as well as the corresponding first and second derivatives, in accordance with an embodiment of the present invention.

In all the figures similar reference numerals identify similar parts.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

International patent application publication no. WO2011/128893 to Kasdan et al., describes a device, system and method for rapid determination of a medical condition and is incorporated herein by reference.

Reference is now made to FIG. 1A, which is a simplified three dimensional front view of a system 101 comprising a reader assembly 100 and a cartridge 110 for detecting a biological condition, in accordance with an embodiment of the present invention.

Shown in FIG. 1A are the reader assembly 100 and the cartridge 110. The cartridge is inserted in the reader assembly as shown. Once the cartridge is inserted in the reader assembly all assay pre-analytical processing and analysis are performed automatically. Results of the analysis are displayed on a user interface touchscreen 115, which is also used to control operation of the reader.

FIG. 1B shows a simplified three dimensional inner front view 103 of reader assembly 100 for detecting a biological condition, in accordance with an embodiment of the present invention.

The internal components of the reader assembly are shown in FIG. 1B. There is seen left side view 120, showing an ITX computer, 122, a Galil motor controller, 124, an electronics power supply 126, cartridge, 110, inserted into a cartridge handling unit (CHU) 128 and a forward scatter detector 130. Also seen, is a right side view 140 showing reader optics 142, a data acquisition board 144 and a general electronics printed circuit board 146.

Figure 2A:
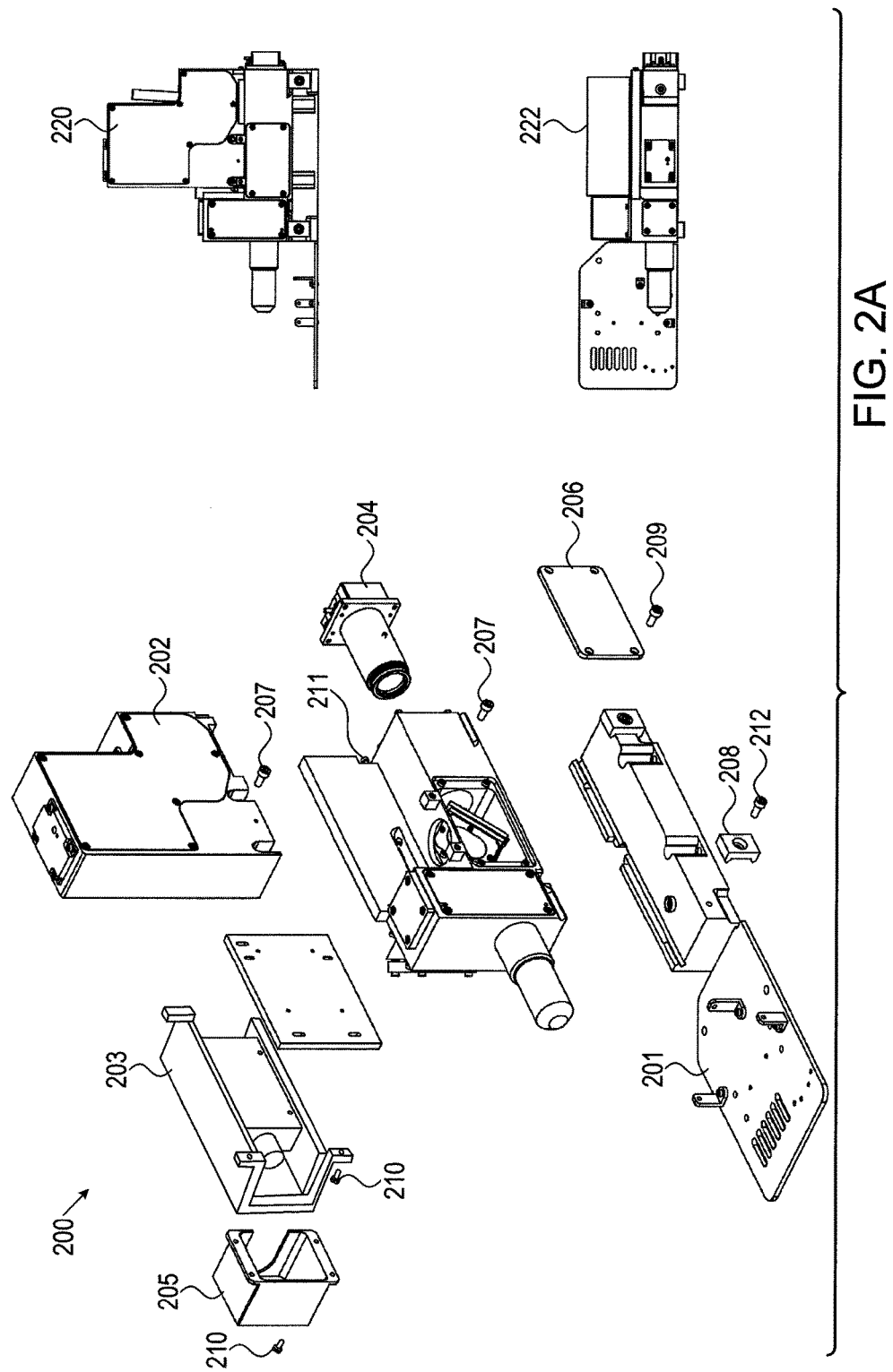
Figure 2B:
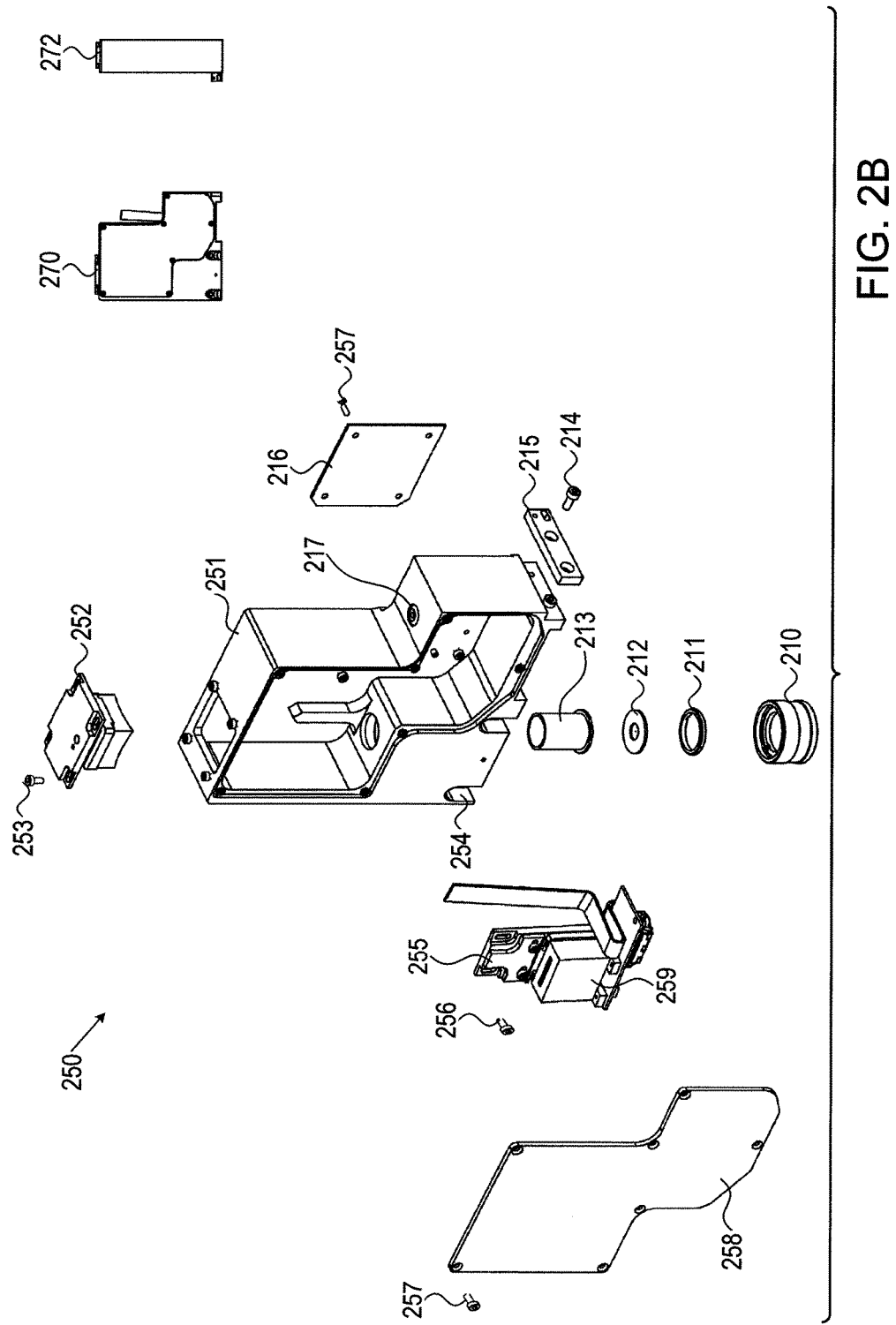

Reference is now made to FIG. 2A, which is a simplified blown up diagram of a reader optics assembly 200 for detecting a biological condition, in accordance with an embodiment of the present invention. FIG. 2B is another simplified blown up diagram of a photomultiplier tube 250 of the optical reader assembly for detecting a biological condition, in accordance with an embodiment of the present invention.

FIG. 2A shows the main modular components of a reader optics assembly 200. A complete side view 220 of the optical assembly is seen, in addition to a top view 222. A laser unit 203 includes a laser and beam expander 223 in its heat sink assembly 221. The assembly further comprises an excitation and emission collection optics 204. The reader optics assembly also comprises a photomultiplier assembly 202, a laser mirror cover 205, a PMT mirror cover 206, a modified M6 set screw 207, a box clamp 208, and various screws 209-211. The reader optics assembly is assembled as shown in FIG. 2A.

FIG. 2B shows details of the PMT assembly. A side view and an end view of the PMT assembly are shown as side view 270 and end view 272 respectively. The major elements of the PMT assembly include a PMT box 251, a PMT grating assembly 252, a PMT bridge assembly 255, a PMT cover 258, a PMT unit 259, a PMT lens assembly 260, a PMT pinhole nut 261, a pinhole 262, a pinhole hood 263 and an adjustment bar 265.

Figure 3A:
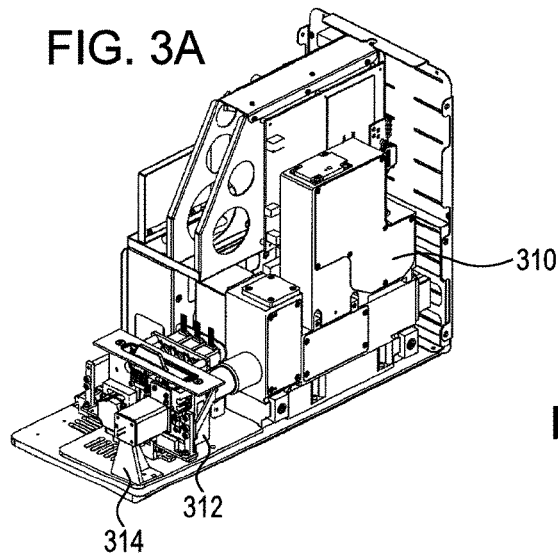

FIG. 3A shows a reader optics assembly 310, a cartridge handling unit 312 and a forward scatter detection unit 314, in accordance with an embodiment of the present invention.

Figure 3B:
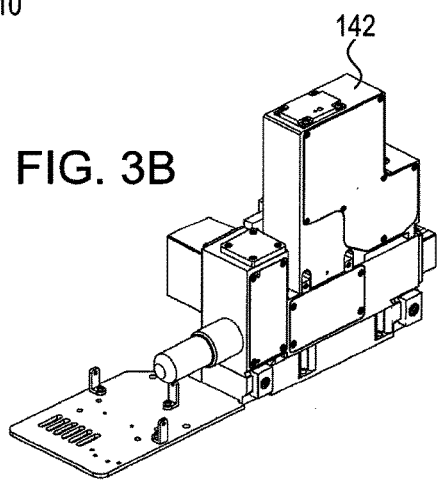

FIG. 3B shows a right side view of a complete reader optics assembly 142, in accordance with an embodiment of the present invention.

Figure 3C:
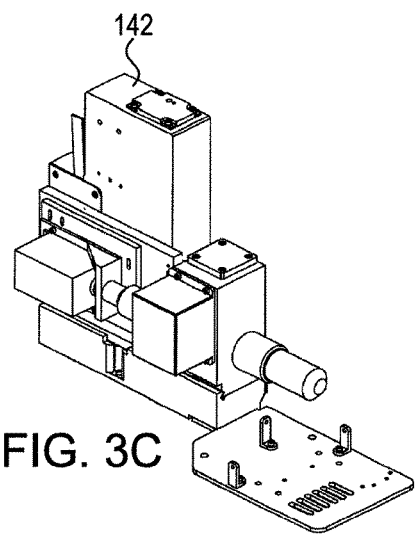

FIG. 3C shows a left side view of the reader optics assembly, in accordance with an embodiment of the present invention.

Figure 3D:
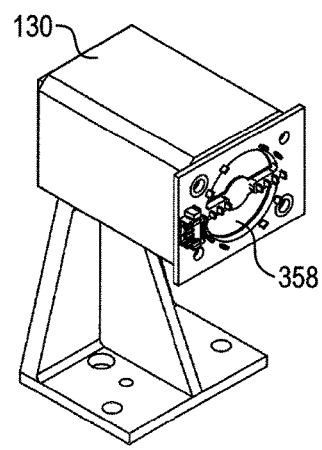

FIG. 3D is a forward scatter detection assembly 130, in accordance with an embodiment of the present invention. This assembly contains LEDs, 352, to illuminate a reading channel (such as reading channel 1452 (FIG. 14M) during an autofocus process, a stop 358, to block low angle scatter and a lens 356 to collect the desired forward scatter for the detection photodiode. (forward scatter detector 130, FIG. 1B).

Figure 3E:
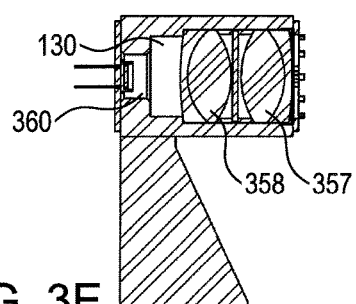

FIG. 3E is a side view of forward scatter detection assembly 130, in accordance with an embodiment of the present invention. Shown in this view are an illumination lens 350, collection lenses 356, 357, and 358, as well as a detection photodiode 360.

FIG. 4A shows a cutaway view of reader assembly 130, in accordance with an embodiment of the present invention. This is cutaway view of the reader assembly showing its components in its front and on a left side. These components include an ITX board 122, a cartridge handling unit 128, and the forward scatter detection assembly, 130.

FIG. 4B shows an exploded right side view of a reader assembly 129, in accordance with an embodiment of the present invention. The three major components in this view are a reader optics assembly 142, a cartridge handling unit 128, and a forward scatter detection module 130.

FIG. 4C shows a left side blown up view of the reader assembly, in accordance with an embodiment of the present invention. Shown in this view are ITX computer board 122, cartridge handling unit 128, forward scatter detection assembly 130, and the other side of the reader optics assembly, 142.

FIG. 4D shows a rear view of cartridge handling unit (CHU) 128, in accordance with an embodiment of the present invention. In this view, a handle 199 of the inserted cartridge, 110, can be seen. Sensors 412 are configured therein to detect the position of motors 410, and actuators 414, which are adapted to crush the blisters, as well as an actuator 416 (940, FIG. 9, 1415, 1417 FIGS. 14A-L), can be seen on the shafts 417 of the motor. An opening 418 is provided for the microscope objective 438 to view the reading channel on the cartridge.

FIG. 4E shows a front view of a cartridge handling unit (CHU), in accordance with an embodiment of the present invention. This figure shows the front view of the cartridge handling unit (CHU) 128. In this view, the handle in the upper portion of cartridge 110 can be seen. A port 420 to view the microfluidic path is provided. This port is viewed by a camera 430, in order to ensure that the correct operation occurs within the cartridge. Another opening 441 is provided for the forward scatter to exit the cartridge handling unit and be observed by the forward scatter detection assembly 130.

FIG. 5 shows an exploded view of a reader assembly 130, in accordance with an embodiment of the present invention.

FIG. 6 is a simplified illustration of a disposable cartridge 6050 for rapid determination of a medical condition, in accordance with an embodiment of the present invention;

Disposable cartridge 6050 is adapted to receive a bodily fluid, such as, but not limited to, blood, urine, serum or plasma. The disposable cartridge is constructed and configured to have several different sections 6052, 6054, 6056 and 6058. Section 6052 is a body fluid aspiration section, which is adapted to receive the body fluid directly or indirectly from the patient (or animal) and this section acts as a reservoir of the body fluid.

Disposable cartridge 6050 comprises fluid conveying means between the sections; such as, but not limited to, air pressure, liquid pressure, mechanical means and combinations thereof. Body fluid aspiration section 6052 is adapted to convey a predetermined quantity of the body fluid (a body fluid sample 6051) to a pre-analytical sample processing section 6054.

In pre-analytical sample processing section 6054, at least one preparatory step is performed on the body fluid such as, but not limited to:
  a) incubation with at least one antibody;
  b) incubation with at least one antigen;
  c) staining of at least one cell type in the body fluid;
  d) enzymatic lysing of at least one cell type of the body fluid;
  e) osmotic lysing of at least one cell type of the body fluid;
  f) heat or cool at least part of the bodily fluid;
  g) addition of reference material to the bodily fluid; and
  h) chemical reaction with at least one element of the body fluid.

The pre-treated sample of bodily fluid is then conveyed from pre-analytical sample processing section 6054 to a sample excitation/interaction zone or section 6056. This pre-treated sample may be conveyed continuously or in a batch mode to sample excitation/interaction section 6056.

FIG. 7A is a simplified schematic illustration of an optical arrangement of a reader optics assembly 400, in accordance with an embodiment of the present invention;

A laser 440 or other appropriate light source provides a light beam 442, which may be directed towards a plurality of optical elements, including a dichroic filter 443, a beam splitter 444, a focusing lens 445, a pinhole 446 and a silicon reader unit 447, for recording a signal from a beam 442 directed through the objective 438 towards a sample 450 and returned to the optical unit. Additional optical elements may include an optional attenuator 448, a high-pass filter 449, a focusing lens 451, a slit 452, a concave grating 453, and a PMT array 454. This arrangement of elements, representing an embodiment of the present invention, allows for generation of excitation light, focusing it on a sample, collecting reflected and emitted light signal resulting from the interaction of the excitation light and fluorophores in the sample and recording said returned light so as to determine fluorescence of sample in response to light illumination from laser 440.

With respect to FIG. 7A, the laser illumination 442 is reflected by the dichroic filter 443 through the objective 438 and focused on the channel containing the flowing particles 458. This illumination excites the fluorophores attached to the protein markers that are bound to the cells.

The resulting fluorescent illumination is collected by the objective 438 and because of the longer wavelength of this emission passes through the dichroic filter 443 and is reflected by the beam splitter 444 through the high pass filter 449. The high pass filter blocks any reflected laser illumination. The focusing lens 451 focuses the multi-wavelength emission illumination on the slit 452. The concave grating 453 images the slit at multiple wavelengths on the elements of the PMT array 454. This completes the process of creating a multispectral detection of the fluorescent emission.

While most of the illumination collected by the objective is reflected by the beam splitter 444 a small fraction is allowed to pass through and is focused by focusing lens 445 through a pinhole 446 on the silicon reader unit 447, which may be a single photodiode or a focal plane array such as CCD sensor. During the focusing operation best focus is achieved when the signal on this reader unit 447 is maximized. When this signal is maximized, the intensity of the signal on the PMT array 454 is also maximized.

Reference is now made to FIG. 7B, which is another simplified schematic illustration of optical arrangement 460 of a reader optics assembly 400 (FIG. 7A), in accordance with an embodiment of the present invention;

With respect to FIG. 7B, as in FIG. 7A, the laser illumination is reflected by the dichroic filter 472 through the objective 476 and focused on the channel containing the flowing particles. This illumination excites the fluorophores attached to the protein markers that are bound to the cells. The resulting fluorescent illumination is collected by the objective 476 and because of the longer wavelength of this emission passes through the dichroic filter 472 and is reflected by the beam splitter 468 through the high pass filter 470. The high pass filter 470 blocks any reflected laser illumination. The focusing lens 466 focuses the multi-wavelength emission illumination on the slit 478. The concave grating 482 images the slit at multiple wavelengths on the elements of the PMT array 476. This completes the process of creating a multispectral detection of the fluorescent emission. While most of the illumination collected by the objective 476 is reflected by the beam splitter 468 a small fraction is allowed to pass through and is focused through a pinhole 464 on the silicon reader unit 462. During the focusing operation best focus is achieved when the signal on this reader unit is maximized. When this signal is maximized, the intensity of the signal on the PMT array 476 is also maximized.

FIG. 8A is a schematic representation of one example of multi-wavelength excitation in the optical unit of FIG. 7A or 7B, in accordance with an embodiment of the present invention;

Reference is now made to FIG. 8A, which is a schematic representation 500 of one example of multi-wavelength excitation in the optical unit of FIG. 7A or 7B, in accordance with an embodiment of the present invention. FIGS. 8A-8C show an extension of the optical configuration in FIGS. 7A and 7B, to allow multiple excitation wavelengths.

FIG. 8A shows the configuration for combining multiple lasers of different wavelengths to yield a single coaxial beam 514 containing all of the wavelengths. Two different wavelengths, such as green 502 and red 506, may be combined using a dichroic mirror 504. One of the beams, red 506 is reflected by the dichroic mirror, while the second beam, green 502 passes through the dichroic mirror to yield a single beam 508, yellow, containing both wavelengths. This combined wavelength beam is now used as one of the inputs to a second dichroic mirror 516 with the third wavelength 512 being reflected by the second dichroic mirror to yield a single coaxial beam 510 containing all three wavelengths.

Reference is now made to FIG. 8B, which shows a graphical output 520 of transmission as a function of wavelength for dichroic filter 500 of FIG. 7B, employing the multi-wavelength excitation of FIG. 8A, in accordance with an embodiment of the present invention.

A multiband dichroic mirror (not shown) similar, or identical to, mirror 552 of FIG. 8C is used to illuminate the sample through an objective 554 (FIG. 8C), while allowing the resulting emission to pass through dichroic mirror 552 at all wavelengths, except those of multibeam excitation 514 (FIG. 8A).

In this way the same epi-configuration used with a single wavelength can, in fact, be used with appropriate changes to dichroic mirror 552 and the addition of multiple lasers 502, 506, 512 to provide multi-wavelength excitation, while maintaining virtually all of the detection wavelengths of a single excitation system.

Turning to FIG. 8C, a schematic representation of part 550 of the optical unit is seen, employing multi-wavelength excitation of FIG. 8A and the dichroic filter of FIG. 5B, in accordance with an embodiment of the present invention. Part 550 may, in some cases, replace subsystem 475 (FIG. 7B).

Table 1 shows representative values for representative components for use in the present invention.

| Laser Wavelength | 405 nm | 488 nm |
|---|---|---|
| Laser Power | 50 mW | 20 mW or 50 mW |
| Sensing Spectral Range | 200 nm | 200 nm |
| Spectral Resolution | 25 nm | 25 nm |
| Number of Detectors | 8 | 8 |
| Collecting Optics | Microscope Objective N.A. > 0.4, W.D. ≈ 6 mm | Microscope Objective N.A. > 0.4, W.D. ≈ 6 mm |
| Detector Type | S.S. PMT 8 ch | S.S. PMT 8 ch |

While much of the previous discussion has focused on the optical elements of some embodiments of the present invention, one of the key components of the diagnostic system herewith presented is a disposable sample cartridge.

Reference is now made to FIG. 9A, which is a schematic view of a sampling cartridge 110 of FIG. 1A, in accordance with an embodiment of the present invention. The cartridge 650 includes a pre-analytical component 652 into which a sample (not shown) may be introduced.

The sample will generally be blood, either whole or a component (serum, etc.) thereof. Other liquid samples may additionally or alternatively be employed. In the pre-analytical component 652, the sample is allowed to interact with chemicals pre-packaged into component 652. The interaction may be either passive or include active mixing. The chemicals included in the analytical component 652 may be either wet or dry, and generally include antibodies associated with fluorescent probes. Antibodies are pre-selected for their ability to bind with predetermined biological markers or the like. In a typical experiment, a predetermined volume (generally less than 50 microliters) of blood is introduced into the pre-analytical component 652 of a disposable cartridge 650. The sample is actively mixed with chemical reagents present in the pre-analytical component 652 for a predetermined period of time, generally less than ten minutes. The sample is then moved through a capillary region 653 by means to be discussed, where it is exposed to a light beam 642 delivered from an objective 638. Direction of sample flow is as shown by the arrow in the capillary region 653.

The capillary region 653 is designed to allow flow of particles in a single-file past the light beam 642. Such an arrangement allows both for counting the number of particles as well as individual interrogation of particles to determine the presence of biological markers (via their associated fluorescent tags) on each particle. Such a physical arrangement allows for detection of one or more biological markers (independent of particle-specific properties such as size, shape, and number) on each particle.

Finally, there is a collection component 654 which receives sample after exposure to light beam 642. This is a waste region and allows for a completely self-contained disposable for sample preparation, analysis and waste collection. It is noted that the disposable cartridge may be of any relevant shape and is shown as it is in FIG. 6 for ease of understanding of its components and functionality.

As mentioned above, the sample, after pre-analytical treatment to allow for binding of fluorescent tag to cells/particles, must flow under a light beam 642, produced by an optical unit (not shown). The flow is generally "single file" so as to allow for accurate determination of cell-specific markers on each analyzed cell. Methods to induce flow include but are not limited to electrical stimulation, chemical induction, and vacuum pull. In an electrical stimulation system, charge is applied across the capillary region 653 so as to induce charged particles to move from the pre-analytical component 652 towards the collection component 654. The charge could be supplied by the cytometer in which the disposable cartridge 650 is placed or from an external source.

Alternatively, the capillary region may include chemical features (hydrophilic/hydrophobic; positive/negative charge) to encourage sample to move from left to right as shown in FIG. 9A. Alternatively, a vacuum from the collection component 654 could be applied to pull sample from the pre-analytical component 652 through the capillary region 653. Other methods may be employed to get liquid sample to move underneath the light beam 642 for analysis.

As described herein, the optics and sample handling have been handled separately. Such an arrangement is not mandatory, as some of the optical features needed for proper sample analysis may be included in a disposable cartridge.

Reference is now made to FIG. 9B, which shows a schematic view of disposable cartridge 800 in flow-cytometer device, such as system 100 in accordance with an embodiment of the present invention. Attention is currently turned to FIG. 9B which shows an expanded view of a capillary region 853.

In the capillary region 853, particles flow in the direction as suggested by the arrow 880. Particles 890 flow past an objective 838 that shines light 842 through the capillary 853. Flow restriction elements 894 may be present in the capillary region 853 so as to encourage particles 890 to move past the light 842 in a nearly single-file manner. Passage of multiple particles together may be resolved through processing software.

A molecular marker 895 on a particle 890 may be illuminated by light 842 and its fluorescence will be captured by a proximate photomultiplier tube 899. The photomultiplier tube 899 may distinguish the wavelength of the fluorescence and thus which biological marker 895 is present on particle 890. Thus, the systems of the present invention may determine which biological markers are present on particles 890, which are detected in the systems of the present invention. A photomultiplier tube 899 may have a plurality of tubes or an array of elements for fine wavelength discrimination and alternatively may be replaced with film, CCD or other appropriate light-receiving reader unit. It should be understood that FIG. 9B shows one embodiment of the configuration of system 101 (FIG. 1) in a transmissive configuration, wherein detector (photomultiplier tube 899) is disposed on an opposing side of the cartridge 800 to objective 838.

The systems of the present invention comprise controller software which are adapted to run a diagnostic process. It is understood that the controller software may be an integral part of the flow-cytometer or alternatively be installed on an associated computing device 122 (FIG. 1B), which may include, but not be limited to, a laptop computer, iPod, iPad, cell phone or mainframe computer.

Reference is now made to FIG. 10, which is a simplified flowchart 1000 of a method for rapid determination of a medical condition, in accordance with an embodiment of the present invention. It is to be understood that the method described herein depicts one non-limiting embodiment of the present invention for determining the health state of a patient. Further embodiments are also construed to be part of the present invention.

In a body fluid provision step 1002, a body fluid, such as blood, urine, serum or plasma is provided from a human or animal patient. Typically, the sample is fresh, but may also be a stored, refrigerated or frozen-thawed sample. The fluid is typically liquid and at a temperature of 4-37° C.

In a body fluid introduction step 1004, part or all of the body fluid sample 6051 (FIG. 6) is introduced into disposable cartridge (110, FIG. 1A).

In a reacting step 1006, the fluid sample is reacted with at least one reactant in the cartridge forming a treated sample. According to some embodiments, this step is performed in pre-analytical sample processing section 6054 (FIG. 6) as described in detail hereinabove.

In an impinging step 1008, radiation is impinged on the treated sample, such as, but not limited to, in a sample excitation/interaction section 6056, thereby generating a plurality of spectrally distinct signals in the direction of optics unit 142 (FIG. 1C, see description hereinabove).

In a spectral emissions detection step 1010, a plurality of spectrally distinct signals is detected by multiple emission detector 454 (FIG. 7A). The detector outputs data.

Thereafter, in a data processing step 1012, the outputted data is processed by signal processor 6036 (FIG. 6) and/or by computer 122 (FIG. 1C) to provide an output indicative of a medical condition.

FIG. 11 is a three-dimensional graph showing the optical output over time of reference beads (RM) relative to a sample from a human patient (PMN), in accordance with an embodiment of the present invention.

FIG. 11 shows a three-dimensional graph showing the optical output over time of reference beads (RM) relative to a sample from a human patient (PMN), in accordance with an embodiment of the present invention. The emission amplitude in the six bands, 500-525 nm, 525-550 nm, 550-575 nm, 575-600 nm, 600-625 nm and 625 to 650 nm is displayed in the graph for each sample time. Different fluorophores have different emission spectra. It can be appreciated that both spectral content or shape and amplitude at individual wavelengths are significantly different for neutrophils stained with Acridine Orange (AO) and reference beads (RM) containing a bright broad spectrum fluorophore. The peak of the AO emission is in the 525-550 nm band, while that of RM is in the 500-525 nm band and is of a significantly greater amplitude than AO in any band.

FIGS. 12A-12C show graphs of optical outputs over time of the reference beads and the sample from a human patient, in accordance with an embodiment of the present invention.

Turning to FIGS. 12A-12C, there can be seen graphs of optical outputs over time of the reference beads and the sample from a human patient, in accordance with an embodiment of the present invention. In these two-dimensional figures, the traces from each of the bands are overlaid on the same graph. FIG. 12A shows the boxed pulses from neutrophils in FIG. 12B. It is clear from these graphs that the amplitude in the 525-550 nm channel exceeds the amplitude in the 500-525 nm channel, which is the characteristic of AO. FIG. 12C shows a comparison of the AO stained neutrophil emission spectrum to that of the RM emission spectrum. The relative amplitude of the spectrum in the 500-525 nm band to that of the amplitude in the 525-550 nm band clearly distinguishes the two fluorophores. In addition, the maximum amplitude of the RM emission is significantly greater than that of AO.

The systems of the present invention, as described and shown herein provide uses, such as, but not limited to, at least one of the four following scenarios:
  a) When multiple pieces of information, such as biological markers and white cell state are required in order to make an accurate diagnostic determination;
  b) When multiple sequential measurements must be made in order to determine the position of a patient on an illness curve;
  c) When white cell and similar data are needed quickly and in a POC environment; and
  d) When fluorescent signals overlap in wavelength and there is need to determine relative contribution of each signal for a given wavelength range.

The instant invention includes software and algorithms for proper data analysis and conversion of raw fluorescence data into actual concentrations of relative biological markers.

FIG. 13A is an outer side view of a cartridge assembly 1300, in accordance with an embodiment of the present invention and FIG. 13B shows an inner side view 1350 of a cartridge assembly 1300, in accordance with an embodiment of the present invention.

FIG. 14A-14O show a sequence of process events in a cartridge assembly, in accordance with an embodiment of the present invention;

FIG. 14A-14O are a sequential set of schematic drawings of the operation of a system 101 (FIG. 1A) for detecting a biological condition, in accordance with an embodiment of the present invention.

In FIG. 14A, a blood sample 1401 enters a specimen receiving element 1418 and fills a chamber 1404.

In FIG. 14B, a blister 1420 comprising a treatment composition 120 (FIG. 1) is pressed and an antibody cocktail is mixed with 10 microliters of the blood sample.

In FIG. 14C, a mixing bellows 1415 is pressed and this effects mixing of the antibody cocktail and the 10 microliters of the blood sample in a first mixing chamber 1412 to form a first mixture 1403.

In FIG. 14D, the bellows is released and mixture 1403 is siphoned along a tortuous channel 1413 and into a second mixing chamber 1411. Upon release of the bellows, the first mixture returns from the second mixing chamber, back along the tortuous channel to the first mixing chamber. Every time the bellows is pressed the mixture moves towards the second chamber and every time it is released, it returns, wholly or in part to the first chamber. This mixing may be performed multiple times.

In FIGS. 14E-14G, a second composition blister 1422 is pressed, releasing a second composition 122 (FIG. 1), such as a lysis composition thereby forming a second mixture 1405. The second mixture is mixed by pressing of bellows 1415, the second mixture returns from the second mixing chamber, back along tortuous channel 1413 to the first mixing chamber. Every time the bellows is pressed the mixture moves towards the second chamber 1411 and every time it is released, it returns, wholly or in part to the first chamber 1412. This mixing may be performed multiple times.

In FIGS. 14H-14J, a third blister 1424 is released comprising a third composition 124 (FIG. 1), such as a control reference, into the second mixing chamber, thereby forming a third composition 1407. The third mixture is mixed by pressing of bellows 1415, the third mixture returns from the second mixing chamber, back along tortuous channel 1413 to the first mixing chamber. Every time the bellows is pressed the mixture moves towards the second chamber 1411 and every time it is released, it returns, wholly or in part to the first chamber 1412. This mixing may be performed multiple times.

In FIGS. 14J-14M, a reading bellows 1417 is pressed, which forces some of the third composition towards a reading cuvette 1430.

In FIGS. 14N-14O, particles 1460 from the third composition flow from the cuvette 1430 along a reading channel 1452 to a reading region 1450. The cells pass through the reading region and are excited by one or more lasers 1462, 1463. At least one excitation laser beam 1464 impinges on cell 1460 and an emission beam 1466 is detected by a detector 1470. In one example, this is cell emission fluorescence and detector 1470 is a spectrometer.

FIG. 15 is a schematic illustration of a micro flow spectrometer reading, in accordance with an embodiment of the present invention;

An individual cell 1505 flows through a detection region 1510 in a microfluidic channel (seen as 1452, FIG. 14M). Additionally, tagged cells 1520 labeled with antibodies conjugated with multiple wavelength fluorescent tags flow through the detection region. A diode laser 1530 impinges a ray/beam 1510 onto the cells and tagged cells. The cells and tagged cells emit different emission spectra (not shown). An optical grating 1540 disperses emission spectra via a grating 1540 into its constituent wavelengths 1550.

A photomultiplier tube (PMT) array 1560 or avalanche diode array detects fluorescence at 8 different spatial locations corresponding to 8 spectral regions.

FIG. 16 is a flow chart of a method for optical processing 1600, in accordance with an embodiment of the present invention.

In a forming laser step 1602, a laser excitation beam shape is formed.

The excitation beam is reflected from a dichroic mirror 504 (FIG. 8A, or 472 FIG. 7B) and through objective 476 (FIG. 7B) onto a reading channel 1452 (FIG. 14M), in a reflecting step 1604.

In a forward scatter measuring step 1606, the forward scatter from particles 1460 (FIG. 14N) in the reading channel is measured to detect events.

Thereafter, in a passing step 1608, particle fluorescent emission is allowed to pass through a dichroic mirror and be reflected from a beamsplitter 468 into a detection path.

In an imaging step 1610, parts of the beam emission, which are not reflected are passed through the beamsplitter onto an image sensor, such as silicon detector 462 (FIG. 7B).

In parallel to step 1610, the reflected part of the beam is filtered in a beam filtering step 1612 in the detection path to allow only wavelengths above an excitation wavelength to pass through a filter.

In a focusing step 1614, the filtered beam from step 1612 is focused onto a pinhole or slit to select a reading zone region to be analyzed.

Thereafter, in a dispersing step 1616, the dispersed pinhole or slit is dispersed and imaged onto a multi-element electrooptical detector (6034, FIG. 6).

FIGS. 17A-17B are schematic illustrations of steps of use of a graphical user interface, in accordance with an embodiment of the present invention;

Upon powering up the unit a first screen 1702 appears with a message notifying the user that the system is performing a self-check along with a countdown indicator 1703. Once the self-check is complete, an assay selection screen 1704 appears. The user touches the button corresponding to the assay to be performed. The next screen 1706 is used to enter the patient identification. This may be done by touching the numerals of the touchpad 1709 or by scanning a barcode. Once the entry is complete, the user touches the forward button 1707 and a screen requesting the user to enter the cartridge 1708 appears. Once the user inserts the cartridge the system checks to ensure that the cartridge identified by its barcode label corresponds to the selected assay and begins the processing. While processing, a screen 1710 is displayed showing the processing progress and the time remaining. Once the pre-analytical and analytical processing is completed the results are displayed on a screen 1712 with an indication of where the results lie in the range of possible results 1713. After the user touches a "proceed to next screen indicator" 1711 a screen instructing the user to remove the cartridge 1714 appears. The user has the option of repeating this test with another sample by pressing the repeat icon 1715 or displaying the most recent results on a screen 1716.

Reference is now made to FIG. 18, which is a simplified illustration of a method for a disposable cartridge 1850 of system 101 of FIG. 1A for rapid determination of a medical condition, in accordance with an embodiment of the present invention.

When practicing the method of disposable cartridge 1850 a bodily fluid, such as, but not limited to, blood, urine, serum or plasma is transferred from the donor to the cartridge 1851. The disposable cartridge method includes multiple steps to effect the analysis and diagnosis 1852, 1854, 1856 and 1858. In step 1852 a body fluid aspiration step, receives the body fluid directly or indirectly from the patient (or animal) and transfers the body fluid to a reservoir.

The disposable cartridge method 1850 utilizes fluid conveying means, such as, but not limited to, air pressure, liquid pressure, mechanical means and combinations thereof to move fluids. Body fluid aspiration step 1852 is adapted to convey a predetermined quantity of the body fluid (a body fluid sample 1851) for a pre-analytical sample processing step 1854.

In pre-analytical sample processing 1854, at least one preparatory step is performed on the body fluid such as, but not limited to:
i) incubation with at least one antibody;
j) incubation with at least one antigen;
k) staining of at least one cell type in the body fluid;
l) enzymatic lysing of at least one cell type of the body fluid;
m) osmotic lysing of at least one cell type of the body fluid;
n) heating or cooling at least part of the bodily fluid;
o) addition of reference material to the bodily fluid; and
p) chemical reaction with at least one element of the body fluid.

The pre-treated sample of bodily fluid is then transferred (1855) after pre-analytical sample processing step 1854 to a sample excitation/interaction step 1856. This pre-treated sample transfer for excitation/interaction 1856 may be performed continuously or in a batch mode.

Part of sample excitation/interaction 1856 is to position the sample to sit in the light path of an excitation illumination. The excitation illumination passes radiation, such as coherent or incoherent radiation in or outside the visible range into the pre-treated sample. Resultant emission or emissions from the pre-treated sample is detected 1834, and processed 1836 to produce a report 1812 summarizing the analysis and diagnosis.

Multi-spectral emission detection 1834 receives the emission from the pre-treated sample in multiple spectral bands. In some cases these bands are non-overlapping bands. Multi-spectral emission detection 1834 is adapted to pass data representing the spectral bands to multi-spectral fluorescence signal processing 1836.

Multi-spectral fluorescence signal processing 1836 may comprise two or more sub-elements (not shown) including:
a) a photon counting analysis;
b) other detecting analysis elements (not shown) for measuring other optical outputs of multi-spectral emission detection 1834.

The method further comprises a spent sample disposal method 1858, for receiving a sample from the sample excitation/interaction processing.

The method further comprises computer program 1810, the computer program is adapted to receive data related to the plurality of spectrally distinct signals and a processor, adapted to process said data and to output at least one output related to said medical condition. One type of output provided is a visual output which is outputted onto a screen 1812 of the computer.

FIG. 19A is a simplified flow chart of a method 600 for differentiating between different particles, in accordance with an embodiment of the present invention.

The input to the processing is a time series from each of the channels in the eight channel photomultiplier array 601. In addition, data from multiple scatter channels 609 is introduced. Each fluorescent time series and scatter time series may be processed individually employing respective spectral cross-correlation algorithm 606 and scatter algorithm 607 to smooth it and minimize noise. Two possible processing methods are boxcar averaging algorithm 602 and matched filtering algorithm 604. In addition, groups of individual channels may be correlated to yield a multiple spectral crosscorrelations 606. One or more of these derived time series may be used to determine event locations.

Once an event is located in the eight channel time series the composition of that event in terms of known fluorophore signatures is determined using a minimum mean square error fit 610. The event is now described in terms of its composition of known fluors. Each event thus described is stored in an event store, i.e. memory, together with the data from the eight time series for that event and its description 612. Based on the fluor composition for each event in the data store, it is possible to determine the type of particle. For example, a neutrophil 616 is characterized by the single fluor attached to the CD64 antibody shown in FIG. 5 as W1. Thus events that are preponderantly characterized by the single fluor attached to the CD64 antibody are identified as neutrophils.

Similarly, monocytes 618 are characterized by fluors W1 and W2 so that an event with both of these fluor signatures is identified as a monocyte. Similarly, a bead 620 is characterized by an event that has fluors W1 and W3. Lymphocytes 622 do not express significant fluorescence but are identified by their scatter as events. Events that do not match any of the known combinations of the fluorophores are identified as rejects 626.

Given the population of identified events, the median intensity of the neutrophil population and the median intensity of the bead population are determined. The ratio of the neutrophil median to the bead median is the desired Leuko64 index. The positive control value is determined as the median intensity of the CD64 fluorophore bound to monocytes divided by the median intensity of the same fluorophore on the bead population. The negative control value is determined by the median intensity of the CD64 fluorophore bound to lymphocytes. These are the key steps in performing the Leuko64 assay.

FIG. 19B is a flow chart of an algorithm for biological detection 1900, in accordance with an embodiment of the present invention;

FIG. 19B shows schematically that the CD4/CD8 assay is performed by determining a particle type for each event in the event store 1912. One method to accomplish this particle selection is to use K means clustering to determine data clusters in the event store based on the signatures Alexa 488, PE 488N and PEAF 488N as shown in FIG. 25. Based on these three signatures events with large values of PE 488N are classified as CD4 positive lymphocytes 1938 since the phycoerythrin (PE) fluor is attached to the CD4 antibody. Events with large values of Alexa 488 are classified as CD8 positive lymphocytes 1940 since the Alexa 488 fluor is attached to this CD8 antibody. Events with large values of PEAF 488N are classified as lymphocytes since this fluor is attached to the CD3 antibody which is expressed by lymphocytes to the exclusion of other WBC. The group 1942 has large values of PEAF 488N but small values of PE 488N and Alexa 488 which corresponds to lymphocytes not expressing either CD4 or CD8. Finally, non-lymphocytes WBC 1936 may be determined by a pan WBC antibody for those events not expressing CD3, and rejects as those events not expressing the pan WBC antibody.

FIGS. 20A-20B shows bandwidth leveled and smoothed arrays, in accordance with an embodiment of the present invention.

FIGS. 20A and 20B show the typical response of the system to fluorescent beads with an F488 signature. The response in 25 nm bands from 500 nm to 700 nm are respectively 2010, 2020, 2030, 2040, 2050, 2060, 2070, and 2080. The traces represent the outputs from the eight channel fluorescent detector with noise, characterized as the median trace value, subtracted. The large signals above the background level are the raw signal smoothed by a box car averager of length 10. The peak value for the F488 signature occurs in the range 525 to 549 nm, 2020. The next highest value occurs in the range 500 to 524 nm, 2010, with decreasing amplitudes in each 25 nm band, 2030, 2040, 2050, 2060, 2070, and 2080.

FIGS. 21A-21B are schematics for solving a fluor decomposition of an observed signal, in accordance with an embodiment of the present invention.

FIG. 21A is the Matlab function used to solve the matrix equation $Ax=b$ for the signature value vector or vectors b corresponding to the observed eight channel emission values x. The \ function in Matlab is used to solve for x using the Matlab expression $x=A\backslash b$.

FIG. 21 B is a table of fluor signatures use as the matrix A described in FIG. 21A.

FIGS. 22A-22B is a graphical comparison of system performance with FITC beads with MESF detection versus FACS, in accordance with an embodiment of the present invention.

FIG. 22A shows a comparison of the linearity of the instant invention with that of a Becton Dickinson FACS flow cytometer. The tabulated median values for the FITC MESF beads are shown in column 2211 in table 2210. The median fluorescent intensity levels (in arbitrary units) for the FACS flow cytometer are shown in column 2212, while those for the instant invention are shown in column 2213. Column 2214 shows the number of events on which the median value is based for the instant invention. The linearity plot for the full range of values for the instant invention is shown in 2220 while that for the FACS flow cytometer is shown in 2230. Also shown in each of these figures is the best fit line through the points along with the square of the correlation value, $R^2$. Comparison of these plots shows comparable performance of the instant invention and the FACS flow cytometer.

FIG. 22B shows a comparison of the linearity of the instant invention 2240 with that of the FACS flow cytometer 2250 over the range restricted to the first four smallest data points. Again, comparable performance is demonstrated.

FIGS. 23A-23B show graphical displays of linearity of system performance with Alexa 488 MESF, in accordance with an embodiment of the present invention.

FIGS. 23A and 23B shows the linearity performance of the instant invention for the Alexa Fluor 488 MESF bead series when the system is run both add fast speed 2310 and flow speed 2330. In this case the measure of performance is the F488 signature normalized to the length of the event. This normalized signature is designated F488N. The tabular listings 2320 and 2340 summarize the statistics for the regression line fit.

FIG. 24 is a three-dimensional graph showing the optical output over time of a CD4-CD8 assay, in accordance with an embodiment of the present invention.

FIG. 24 is a surface plot showing the relative amplitude of event emission in each of the detectors for a thirty second interval. The scale running from left to right 2440 is in 10 μs intervals. The scale running from right to left 2450 and numbered one through eight are the detector elements. Eight corresponds to waveband 1, seven corresponds to waveband 2, and finally one corresponds to waveband 8. An example of CD4 events tagged with phycoerythrin shown in 2510 in FIG. 25 is the trace 2430. An example of CD8 events tagged with Alexa Fluor 488 shown in 2520 in FIG. 25 is the trace 2410. Finally an example of non-CD4 non-CD8 lymphocytes tagged only with Alexa Fluor 610 shown in the group 2530 in FIG. 25 is the trace 2420.

FIG. 25 is a graphical display showing a cluster analysis of a CD4-CD8 assay, in accordance with an embodiment of the present invention;

FIG. 25 is the scatterplot matrix showing the result of applying K means clustering to the signatures Alexa 488N, PE488N and PEAF488N. The meaning of each of the clusters 2510, 2520 and 2530 is described in the description of FIG. 19 B.

FIGS. 26-27 are graphical displays showing cluster separations of the cluster analysis of FIG. 19A, in accordance with an embodiment of the present invention.

FIG. 26 is a scatterplot matrix showing four-color separation of the neutrophil, monocyte, lymphocyte and reference bead populations required to effect a CD64 assay. The leftmost column 2710 shows the complete 4-color separation. The top frame 2720 shows separation of NE & LY from MO and BEADS based on Waveband2 (Alexa488) and separation of MO from BEADS based on Waveband4 (PE).

The middle frame 2730 shows separation of LY from NE based on Waveband6 (A610).

The bottom frame 2740 shows separation of beads from cells based on Waveband8 (Starfire Red).

Since the separation is based on individual narrow bands (not signatures) 45 degree clusters 2750, 2760, 2770 show emission presence in two bands, which in each case is as expected as can be seen from the emission signatures in the table below.

FIG. 28 is a comparison table of different array options, in accordance with an embodiment of the present invention.

FIG. 28 is a tabular listing of photomultiplier arrays produced by Hamamatsu Corporation. The H95308 channel array is the one used in the current implementation of the extant invention. One skilled in the art will appreciate that finer resolution or greater extent of the spectral sampling can be achieved by using either the 16 or 32 channel array products.

FIG. 29A is a flowchart of a specific implementation of an algorithm 1300 for selecting groups of data from a scatterplot, in accordance with an embodiment of the present invention;

The algorithm in FIG. 29A is a specific implementation of the general algorithm in FIG. 29B to select each of the groups 3010, 3020, 3030 and 3040 (FIG. 30) and determine specific parameter values in each of the groups.

In a first ordering signature step 1304 the Star Fire Red (SFR) signature is used to order (from smallest SFR signature to largest) the entire dataset of waveband and signature values 1302.

In a second step 1320, an analysis of a histogram of an SFR signature values as shown in FIG. 14A to select the group 1210. This is a small group 1404 at the upper end of group 1402 in the histogram 1400 in FIG. 31A. The next step is to remove this group from the overall dataset as shown in FIG. 29A Step 1322. The removed group is the bead dataset 1324.

A dataset of Waveband and Signature values with bead dataset removed 1340 is then manipulated as follows. In an ordering step 1342, the data is organized according to its PE (phycoerythrin) signature from smallest to largest PE (phycoerythrin) signature.

In an analyzing PE histogram set step, 1344, the data is manipulated to find a group corresponding to monocytes.

In an extracting monocytes dataset step 1346, a monocyte dataset of waveband and signature values 1348 is extracted. A dataset of waveband and signature values with beads and monocytes removed 1360 is then further processed as follows. Set 1360 is organized according to its PEAF (full name PEAF®488) (see above for beads and PE) signature in an order according to PEAF signature ordering step 1362.

In an analyzing PEAF histogram to find a group corresponding to lymphocytes step 1364, set 1360 is analyzed to determine if any of the data have behavior corresponding to lymphocytes.

In an extraction step 1366, a lymphocyte dataset of waveband and signature values 1368 is extracted from set 1360 and the remaining dataset is a dataset of waveband and signature values with bead, monocytes and lymphocytes removed 1380.

In an order by Diode1 signature step 1382, dataset 1380 is analyzed according to a Diode1 signature (see above). Dataset 1380 is then analyzed in an analyzing step 1384 to find a group of data having properties of neutrophils.

In an extracting step 1386, a group of data having properties of non-neutrophils 1388 is removed. A remaining group 1391 (assumed to be neutrophils) is used in a computing step 1392 to compute desired metric from the group parameters.

Reference is now made to FIG. 29B, which is a flowchart of a general implementation of an algorithm 1350 for selecting groups of data from a scatterplot, in accordance with an embodiment of the present invention.

In a first ordering signature step 1305 a first signature is used to order the dataset of waveband and signature values 1303.

In a second step 1321, an analysis of a histogram of a 1st signature values to find the group corresponding to $1^{st}$ signature 1325, as exemplified in FIG. 31A to select the group 3010. This is a small group 1404 at the upper end of group 1402 in the histogram 1400 in FIG. 31A. It should be noted that this is but one way to select the group and other methods employing additional data set values in combination may be used. The next step is to remove this group from the overall dataset as shown in FIG. 31B Step 1323. A removed group is a 1st signature dataset 1325.

A dataset of Waveband and Signature values with 1st dataset removed 1341 is then manipulated as follows. In an ordering step 1343, the data is organized according to its 2nd signature.

In an analyzing $2^{nd}$ signature histogram set step, 1345, the data is manipulated to find a group corresponding to the $2^{nd}$ signature.

In an extracting $2^{nd}$ signature dataset step 1347, a $2^{nd}$ signature dataset of waveband and signature values 1349 is extracted. A dataset of waveband and signature values with $1^{st}$ and $2^{nd}$ signatures groups removed 1361 is then further processed as follows. Set 1361 is organized according to its $i^{th}$ signature in an order according to $i^{th}$ signature ordering step 1363.

In an analyzing $i^{th}$ histogram to find a group corresponding to $i^{th}$ signature step 1365, set 1361 is analyzed to determine if any of the data have behavior corresponding to the $i^{th}$ signature.

In an $i^{th}$ signature extraction step 1367, an $i^{th}$ signature dataset of waveband and signature values 1369 is extracted from set 1381 and the remaining dataset is a dataset of waveband and signature values with $1^{st}$ $2^{nd}$ and $i^{th}$ a signature groups removed 1381.

In an order by $N^{th}$ signature step 1383, dataset 1381 is analyzed according to an $N^{th}$ signature. Dataset 1381 is then analyzed in an analyzing step 1385 to find a group of data having properties of not having Nth signature properties.

In an extracting step 1387, a group of data having properties of non-Nth signatures 1397 is removed. A remaining group 1395 (assumed to be Nth group) is used in a computing step 1393 to compute desired metric from the group parameters.

FIG. 31A is a histogram 1400 of data of Starfire Red (SFR) signature values, in accordance with an embodiment of the present invention.

FIG. 31B shows a plot 1450 of a polynomial 1452 and first derivative thereof 1456 and second derivative thereof 1458 of histogram 1400 shown in FIG. 31A, in accordance with an embodiment of the present invention.

Referring to FIG. 31B, the method of determining an upper group 1404 in FIG. 31A is as follows. A polynomial 1452 of sufficient degree is fitted to the histogram data 1454 (as shown in FIG. 13A, set 1324) is shown in FIG. 14B. The first derivative 1456 and the second derivative 1458 of this polynomial are computed. A plurality of zeros 1460 of the first derivative are indicated by the square boxes along the zero line. A point where the polynomial is both maximum and has a zero derivative 1462 is indicated by the box with an X in it. This point in the histogram corresponds to the peak of the large group 1402 (FIG. 31A). A next zero 1464 of the derivative of the polynomial corresponds to the end of the large group in the histogram. All points in the histogram above this value are in the small group. Since the dataset has been ordered from smallest to largest based on the value of SFR488, and the histogram horizontal axis is also ordered from smallest to largest value of SFR488 the point at which the large group ends is the value of SFR488 above which records in the SFR488 ordered dataset are to be removed and identified as the bead dataset 1324 of waveband and signature values as indicated in FIG. 13A.

FIG. 32A is a histogram 1500 of data of PE488 signature values, in accordance with an embodiment of the present invention.

FIG. 32B shows a polynomial fitted to the histogram in FIG. 32A as well as a corresponding first derivative 1556 and a second derivative 1558, in accordance with an embodiment of the present invention.

The records remaining in the dataset are now reordered using the PE488 signature from smallest to largest. Histogram 1500 of the PE488 signature values 1502 is shown in FIG. 32A. Again in this case, there is a small group 1504 to the right of the large group 1502 which corresponds to the desired monocyte population. FIG. 32B shows the polynomial 1552 fitted to data 1554 of histogram 1500 in FIG. 32A as well as the corresponding first and second derivatives. The upper group 1504 is determined in the same way as the upper group of the SFR488 histogram as was described previously. It should be noted that while in both of these cases only a one dimensional histogram was analyzed and used as the basis for selecting the desired population, multiple fields from each record in the dataset may be used to effect a group selection.

As noted in FIG. 31A, the monocyte group 1504 is removed from the dataset which now contains primarily lymphocytes, neutrophils and other particles such as unlysed erythrocytes and other debris.

FIG. 33A is a histogram 1600 of data 1602 of PEAF488 signature values, in accordance with an embodiment of the present invention.

FIG. 33B shows a polynomial 1652 fitted to histogram data 1654 from FIG. 33A as well as a corresponding first derivative 1656 and a second derivative 1658, in accordance with an embodiment of the present invention.

The records remaining in the dataset are now reordered using a PEAF488 signature corresponding to lymphocytes. A histogram 1600 of the PEAF488 signature is shown in FIG. 33A and the corresponding polynomial fit with its first and second derivatives are shown in FIG. 33B. The process outlined above is applied in this case as well to identify and remove a small group 1604 appearing at an upper end of the histogram, from a large group 1602. The lymphocyte group is now removed as shown in FIG. 29A leaving a dataset 1380 which now contains primarily neutrophils and other particles such as unlysed erythrocytes and other debris.

While neutrophils 1391 are tagged with a fluorophore with an F488 signature, other particles appear to express this signature because of the unbound fluorophore in solution. The other particles, however, are smaller than neutrophils, which now comprise the group with the largest forward scatter as measured by a Diode1 (forward scatter detector) channel. A histogram of the Diode1 channel is shown in FIG. 34A.

FIG. 34A is a histogram 1700 of data of Diode 1 channel signature values, in accordance with an embodiment of the present invention.

FIG. 34B shows a polynomial 1752 fitted to data 1754 from the histogram in FIG. 34A, as well as a corresponding first derivative 1756 and a second derivative 1758, in accordance with an embodiment of the present invention.

As described above, an upper group 1704 (FIG. 34A) corresponding to larger particles, which are the neutrophils is selected. This completes the decomposition of the original dataset 1302 into the four distinct event groups (1324, 1348, 1368, 1391) shown in FIG. 29A.

Within each group various parameters may be computed from the fields in the dataset. An example is shown in the following table.

| Observations | NAM | MEDUG | MEDF488 | MEDWaveband2 | MEDWaveband2N | INDEX488 | INDEXWaveband2 | INDEXWaveband2N |
|---|---|---|---|---|---|---|---|---|
| SFR488 | 166 | 978.72 | 3395.26 | 3062.00 | 503.80 | 1.00 | 1.00 | 1.00 |
| PE488 | 73 | 3851.88 | 5968.83 | 5843.50 | 723.66 | 1.76 | 1.91 | 1.44 |
| PEAF488 | 332 | 1164.38 | −4.36 | 37.00 | 4.63 | 0.00 | 0.01 | 0.01 |
| F488 | 620 | 379.98 | 379.98 | 361.00 | 37.92 | 0.11 | 0.12 | 0.08 |
| Diode1 | 59 | 7027.00 | −113.54 | −73.00 | −6.81 | −0.03 | −0.02 | −0.01 |

The observations column contains the name of the group. The NAM column is the number of events in the group. The MEDUG column is the median value of the signature for that group. For example in the SFR488 row the median SFR488 signature value is 978.72. The MEDF488 column contains the median value of the F488 signature for the specified group. The MEDWaveband2 column contains the median value of the Waveband2 values in the group. The MEDWaveband2N column contains the median value of the Waveband2N values in the group. The INDEX488 column contains the ratio of the MEDF488 value for the group to that of the SFR488 group. Similarly, INDEXWaveband2 and INDEXWaveband2N are the ratios of the Waveband2 and Waveband2N medians for the group to that of the SFR488 group.

Although, specific groups corresponding to leukocyte subsets and a specific algorithm to compute a specific index based on these groups has been illustrated, one skilled in the art can use this basic approach whenever it is necessary to select groups from a dataset and compute numeric values based on parameters associated with these groups as shown in the general diagram of FIG. 29B.

Other suitable operations or sets of operations may be used in accordance with some embodiments. Some operations or sets of operations may be repeated, for example, substantially continuously, for a pre-defined number of iterations, or until one or more conditions are met. In some embodiments, some operations may be performed in parallel, in sequence, or in other suitable orders of execution.

Discussions herein utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Some embodiments may take the form of an entirely hardware embodiment, an entirely software embodiment, or an embodiment including both hardware and software elements. Some embodiments may be implemented in software, which includes but is not limited to firmware, resident software, microcode, or the like.

Some embodiments may utilize client/server architecture, publisher/subscriber architecture, fully centralized architecture, partially centralized architecture, fully distributed architecture, partially distributed architecture, scalable Peer to Peer (P2P) architecture, or other suitable architectures or combinations thereof.

Some embodiments may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some embodiments, the medium may be or may include an electronic, magnetic, optical, electromagnetic, InfraRed (IR), or semiconductor system (or apparatus or device) or a propagation medium. Some demonstrative examples of a computer-readable medium may include a semiconductor or solid state memory, magnetic tape, a removable computer diskette, a Random Access Memory (RAM), a Read-Only Memory (ROM), a rigid magnetic disk, an optical disk, or the like. Some demonstrative examples of optical disks include Compact Disk-Read-Only Memory (CD-ROM), Compact Disk-Read/Write (CD-R/W), DVD, or the like.

In some embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some embodiments, input/output or I/O devices (including but not limited to keyboards, displays, pointing devices, etc.) may be coupled to the system either directly or through intervening I/O controllers. In some embodiments, network adapters may be coupled to the system to enable the data processing system to become coupled to other data processing systems or remote printers or storage devices, for example, through intervening private or public networks. In some embodiments, modems, cable modems and Ethernet cards are demonstrative examples of types of network adapters. Other suitable components may be used.

Some embodiments may be implemented by software, by hardware, or by any combination of software and/or hardware as may be suitable for specific applications or in accordance with specific design requirements. Some embodiments may include units and/or sub-units, which may be separate of each other or combined together, in whole or in part, and may be implemented using specific, multi-purpose or general processors or controllers. Some embodiments may include buffers, registers, stacks, storage units and/or memory units, for temporary or long-term storage of data or in order to facilitate the operation of particular implementations.

Some embodiments may be implemented, for example, using a machine-readable medium or article which may store an instruction or a set of instructions that, if executed by a machine, cause the machine to perform a method and/or operations described herein. Such machine may include, for example, any suitable processing platform, computing platform, computing device, processing device, electronic device, electronic system, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit; for example, memory, removable or non-removable media, erasable or non-erasable media, writeable or re-writeable media, digital or analog media, hard disk drive, floppy disk, Compact Disk Read Only Memory (CD-ROM), Compact Disk Recordable (CD-R), Compact Disk Re-Writeable (CD-RW), optical disk, magnetic media, various types of Digital Versatile Disks (DVDs), a tape, a cassette, or the like. The instructions may include any suitable type of code, for example, source code, compiled code, interpreted code, executable code, static code, dynamic code, or the like, and may be implemented using any suitable high-level, low-level, object-oriented, visual, compiled and/or interpreted programming language, e.g., C, C++, Java, BASIC, Pascal, Fortran, Cobol, assembly language, machine code, or the like.

Functions, operations, components and/or features described herein with reference to one or more embodiments, may be combined with, or may be utilized in combination with, one or more other functions, operations, components and/or features described herein with reference to one or more other embodiments, or vice versa.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described herein with reference to flow chart illustrations and/or block diagrams of methods, apparatus (systems) and computer program products according to embodiments of the invention. It will be understood that each block of the flow chart illustrations and/or block diagrams, and combinations of blocks in the flow chart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flow charts and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flow charts and/or block diagram block or blocks.

The flow charts and block diagrams in the Figures illustrate the architecture, functionality, and operation of possible implementations of systems, methods and computer program products according to various embodiments of the present invention. In this regard, each block in the flow charts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustrations, and combinations of blocks in the block diagrams and/or flow chart illustrations, can be implemented by special purpose hardware-based systems that perform the specified functions or acts, or combinations of special purpose hardware and computer instructions.

Although the embodiments described above mainly address assessing test coverage of software code that subsequently executes on a suitable processor, the methods and systems described herein can also be used for assessing test coverage of firmware code. The firmware code may be written in any suitable language, such as in C. In the context of the present patent application and in the claims, such code is also regarded as a sort of software code.

The cartridges of the present invention may be constructed and configured such that the treatment composition comprises proteins attached to a surface, such as to beads. A plurality of beads or other structural elements with proteins attached to their surfaces can be made by any one or more of the following methodologies:— simple attachment such as by adsorption via electrostatic or hydrophobic interactions with the surface, entrapment in immobilized polymers, etc.

non-covalent or physical attachment;

covalent bonding of the protein to the bead surface biological recognition (e.g., biotin/streptavidin).

requires two steps: a first layer is formed by silane chemistry such that the surface presents a reactive group (e.g., epoxy, amino, thiol, etc.), and a second layer (e.g., the protein to be immobilized or a linker molecule) is covalently attached via the immobilized reactive groups.

covalent attachment to functionalized polymer coatings on the interior of the device or linkage to the free end of a self-assembled monolayer (SAM) on a gold surface.

The reaction type may include any one or more of antigen-antibody binding, sandwich (such as antibody-antigen-antibody), physical entrapment, receptor-ligand, enzyme-substrate, protein-protein, aptamers, covalent bonding or biorecognition.

Table 2 shows some representative applications of apparatus 100 and methods of the present invention.

TABLE 2

Applications of the apparatus and methods of this invention.

| Application | Type of Test | Relevant FIGS. in this invention | Typical Prior Art Laboratory Turnaround time (TAT)- see references | This invention Turnaround time (TAT) | References |
|---|---|---|---|---|---|
| Application #1 - CD64 Infection & Sepsis | Surface Marker | FIGS. 1-2 and 3-5D | 4 hours | 10 minutes | U.S. Pat. No. 8,116,984, Davis, B H et al., (2006) |
| 1 - Fetal Hemoglobin Test | Plasma Protein | FIGS. 1-2 and 6-8D | 4 hours | 10 minutes | Dziegiel et al. (2006) |
| 2 - Low Platelet Count | Surface Marker | FIGS. 1-2 and 3-5D | 4 hours | 10 minutes | Segal, H. C., et al. (2005): |
| 3 - Resolving BLAST Flag for hematology Lab | Surface Marker | FIGS. 1-2 and 3-5D | 4 hours | 10 minutes | Guerti, K., et al. |
| 4 - CD34 Stem Cell Enumeration Assay | Surface Marker | FIGS. 1-2 and 3-5D | 4 hours | 10 minutes | Sutherland et al. (1996) |
| 5 - Platelets Activation Assay CD62 | Surface Marker | FIGS. 1-2 and 3-5D | 4 hours | 10 minutes | Graff et al. (2002) Divers, S. G., et al. (2003) |
| 6 - D-dimer (Bead based protein) | Plasma Protein | FIGS. 1-2 and 6-8D | 4 hours | 10 minutes | Stein et al. (2004) Rylatt, D. B., et al. (1983): |
| 7 - Chorioamnioitis CD64 | Surface Marker | FIGS. 1-2 and 3-5D | 4 hours | 10 minutes | Hillier et al. (1988) |
| 8 - CD20 Cell Quantitation (Therapy Monitoring) | Surface Marker | FIGS. 1-2 and 3-5D | 4 hours | 10 minutes | Rawstron et al. (2001) Cheson et al. (1996) |
| 9 - CD52 Cell quantitation (Therapy Monitoring) | Surface Marker | FIGS. 1-2 and 3-5D | 4 hours | 10 minutes | Rawstron et al. (2001) |
| 10 - Circulating Tumor Cells | Surface Marker | FIGS. 1-2 and 3-5D | 4 hours | 10 minutes | Cristofanilli et al. (2004 |
| 11 - Reticulated Platelet Assay | Surface Marker | FIGS. 1-2 and 3-5D | 4 hours | 10 minutes | Matic et al. (1998) Ault et al (1993) Wang et al. (2002) |
| 12 - Bacteria Detection in platelet packs | | | 4 hours | 10 minutes | Blajchman et al (2005) McDonald et al. (2005) |
| 13 - Platelet Associated Antibodies | Surface Marker | FIGS. 1-2 and 3-5D | 4 hours | 10 minutes | Michelson (1996) |
| 14 - Residual Leukocyte Count in blood products | Surface Marker | FIGS. 1-2 and 3-5D | 4 hours | 10 minutes | Bodensteiner, (2003) |
| 15 - CD4 HIV AIDS | Surface Marker | FIGS. 1-2 and 3-5D | 4 hours | 10 minutes | Rodriguez (2005). Dieye et al. (2005) |
| 16 - Leukemia Panels - Very complex | Surface Marker | FIGS. 1-2 and 3-5D | 4 hours | 10 minutes | Drexler et al (1986) |
| 17 - Bladder Cancer Screening in Urine - Urine sample | Surface Marker | FIGS. 1-2 and 3-5D | 4 hours | 10 minutes | Ramakumar et al (1999) Lotan et al. (2009) |
| 18 - HLA DR Sepsis and Immunosuppression | Surface Marker | FIGS. 1-2 and 3-5D | 4 hours | 10 minutes | Hershman et al. (2005) Perry et al (2003) |
| 19 - RECAF Protein for Canine and other Cancers | Plasma Protein | FIGS. 1-2 and 6-8D | 4 hours | 10 minutes | Moro et al. (2005). |

TABLE 2-continued

Applications of the apparatus and methods of this invention.

| Application | Type of Test | Relevant FIGS. in this invention | Typical Prior Art Laboratory Turnaround time (TAT)- see references | This invention Turnaround time (TAT) | References |
|---|---|---|---|---|---|
| 20 - CytoImmun - Cervical Screening | | | 4 hours | 10 minutes | Hilfrich et al. (2008) |
| 21 - Procalcitonin (Bead Based Protein) + Feasibility | Plasma Protein | FIGS. 1-2 and 6-8D | 4 hours | 10 minutes | Assicot et al. (1993) Christ-Crain et al. (2004) |

It should be understood that each of the steps of the method may take a predetermined period of time to perform, and in between these steps there may be incubation and/or waiting steps, which are not shown for the sake of simplicity.

According to some embodiments, the volume of the specimen or sample is less than 200 μL, less than 100 μL, less than 50 μL, less than 25 μL or less than 11 μL.

Typically, the total sample volumes are in the range of 10 to 1000 μL, 100 to 900 μL, 200 to 800 μL, 300 to 700 μL, 400 to 600 μL, or 420 to 500 μL.

According to some embodiments, the volume of the treatment composition chambers 106, 108, 110 (also called blisters) is from about 1 μL to 1000 μL. According to other embodiments, the volume of the specimen is from about 10 μL to 200 μL. According to other embodiments, the volume of the specimen is about 1, 10, 20, 30, 40, 50, 60, 70, 80, 90, 100, 120, 140, 160, 180, 200, 250, 300, 350, 400, 450, or 500 μL.

According to some embodiments, the volume of the treatment compositions 120, 122, 124 is at most about 500 μL. According to other embodiments, the volume of the specimen is at most about 200 μL. According to other embodiments, the volume of the specimen at most about 500, 450, 400, 350, 300, 250, 200, 180, 160, 140, 120, 100, 90, 80, 70, 60, 50, 40, 30, 20, 10, or 1 μL.

According to some embodiments, the volume of a reactant is at least about 1 μL. According to other embodiments, the volume of the specimen is from about 10 μL. According to other embodiments, the volume of the specimen is at least about 1, 10, 20, 30, 40, 50, 60, 70, 80, 90, 100, 120, 140, 160, 180, 200, 250, 300, 350, 400, 450, or 500 μL.

The sequence of transfer of the various treatment compositions may be important to the reaction sequence and is typically predefined.

The reading region 1450 (FIG. 14M-N) is configured and constructed for one or more evaluation steps. These may include any of the following, or combinations thereof:
  a) transfer of radiation there-through,
  b) impinging radiation thereupon;
  c) detecting reflected, refracted, and/or transmitted radiation,
  d) detecting emitted radiation;
  e) capturing one or more images thereof;
  f) performing image analysis on the captured images;
  g) measuring electrical characteristics of the treated specimen;
  h) impinging sonic energy thereon;
  i) detecting sonic energy therefrom; and
  j) analyzing the outputs of any one or more of the above steps.

According to some embodiments, the cartridge is introduced into a system as described in International patent application publication no. WO2011/128893 to Kasdan et al., incorporated herein by reference.

According to some embodiments; the apparatus may have on-board means for showing a result, such as a colorimetric strip (not shown). Additionally or alternatively, the results are displayed in a display unit, separate and remote from system 101.

The blood sample is typically whole blood recently removed from a patient. The whole blood comprises mainly red blood cells (also called RBCs or erythrocytes), platelets and white blood cells (also called leukocytes), including lymphocytes and neutrophils. Increased number of neutrophils, especially activated neutrophils are normally found in the blood stream during the beginning (acute) phase of inflammation, particularly as a result of bacterial infection, environmental exposure and some cancers.

CD64 (Cluster of Differentiation 64) is a type of integral membrane glycoprotein known as an Fc receptor that binds monomeric IgG-type antibodies with high affinity. Neutrophil CD64 expression quantification provides improved diagnostic detection of infection/sepsis compared with the standard diagnostic tests used in current medical practice.

CD163 (Cluster of Differentiation 163) is a human protein encoded by the CD163 gene. It has also been shown to mark cells of monocyte/macrophage lineage.

Typically, the total sample volumes are in the range of 10 to 1000 μL, 100 to 900 μL, 200 to 800 μL, 300 to 700 μL, 400 to 600 μL, or 420 to 500 μL.

According to some embodiments, the volume of the treatment composition chambers 106, 108, 110 (also called blisters) is from about 1 μL to 1000 μL. According to other embodiments, the volume of the specimen is from about 10 μL to 200 μL. According to other embodiments, the volume of the specimen is about 1, 10, 20, 30, 40, 50, 60, 70, 80, 90, 100, 120, 140, 160, 180, 200, 250, 300, 350, 400, 450, or 500 μL.

According to some embodiments, the volume of the treatment compositions 120, 122, 124 is at most about 500 μL. According to other embodiments, the volume of the specimen is at most about 200 μL. According to other embodiments, the volume of the specimen at most about 500, 450, 400, 350, 300, 250, 200, 180, 160, 140, 120, 100, 90, 80, 70, 60, 50, 40, 30, 20, 10, or 1 μL.

According to some embodiments, the volume of a reactant is at least about 1 μL. According to other embodiments, the volume of the specimen is from about 10 μL. According to other embodiments, the volume of the specimen is at least about 1, 10, 20, 30, 40, 50, 60, 70, 80, 90, 100, 120, 140, 160, 180, 200, 250, 300, 350, 400, 450, or 500 μL.

The time required to complete an assay using system 101 of the present invention varies depending on a number of factors, with non-limiting examples that include described herein. In some embodiments, the time required to complete an assay is from about 0.5 to 100 minutes. In other embodiments, the time required to complete an assay is from about 1 to 20 minutes. In still other embodiments, the time required to complete an assay is from about 1 to 10 minutes. In some examples, the time required to complete an assay is from about 1, 2, 3, 4, 5, 6, 7, 8, 9, 10, 15, 20, 25, 30, 35, 40, 50, 60, 80, or 100 minutes.

Example

Application No. 1—CD64 Infection & Sepsis

A cartridge 110 (FIG. 1A) is prepared for receiving a blood sample. The cartridge comprises a number of treatment composition chambers 106, 108, 110, adapted to respectively house a corresponding number of treatment compositions 120, 122, 124. These compositions are described in further detail in U.S. Pat. No. 8,116,984 and in Davis, B H et al., (2006)), incorporated herein by reference. In brief, Reagent A comprises a mixture of murine monoclonal antibodies (contains buffered saline), Reagent B—10× Concentrated Trillium Lyse solution (contains ammonium chloride), Reagent C—suspension of 5.2 μm polystyrene beads labeled with Starfire Red and fluorescein isothiocyanate (FITC), (contains<0.1% sodium azide and 0.01% Tween 20).

TABLE 3

Time sequences of steps in the methodology of the present invention for detecting sepsis using CD64 and CD163 antibodies. LeukoDx device- present invention

| Step | Description | Volume (uL) | Duration (min) | comments |
|---|---|---|---|---|
| 1 | Mixing blood and antibodies | Blood- 10 Abs- 50 | 4 | |
| 2 | Adding RBC lysis buffer | 250 | 3 | Might require heating the buffer to 37 C. |
| 3 | Incubating, Vortexing | | 3 | |
| 4 | Adding normalization beads | 2 | Less than 1 | |
| 5 | Reading | | Less than 1 | |
| | Total | 312 | 10 | |

In the case of sepsis, by "normalization" is meant taking the ratio of the median of the target population fluorescence emission to the median of the reference bead population fluorescence emission.

According to some embodiments, the readout may comprise an optoelectronics core, which enables identification and detection of fluorescent signals.

The CCD in the core, used for focusing, can also be used to read chemiluminescent signals. The readout to user may also indicate where the result falls relative to reference ranges.

The contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

REFERENCES

Assicot, Marcel, et al. "High serum procalcitonin concentrations in patients with sepsis and infection." *The Lancet* 341.8844 (1993): 515-518.

Aulesa, C., et al. "Validation of the Coulter LH 750 in a hospital reference laboratory." *Laboratory Hematology* 9.1 (2003): 15-28. Hawkins, Robert C. "Laboratory turn-around time." The Clinical Biochemist Reviews 28.4 (2007): 179.

Ault, Kenneth A. "Flow cytometric measurement of platelet function and reticulated platelets." *Annals of the New York Academy of Sciences* 677.1 (1993): 293-308.

Blajchman, Morris A., et al. "Bacterial detection of platelets: current problems and possible resolutions." *Transfusion medicine reviews* 19.4 (2005): 259-272.

Bodensteiner, David C. "A flow cytometric technique to accurately measure post-filtration white blood cell counts." *Transfusion* 29.7 (1989): 651-653.

Cheson, Bruce D., et al. "National Cancer Institute-sponsored Working Group guidelines for chronic lymphocytic leukemia: revised guidelines for diagnosis and treatment." *Blood* 87.12 (1996): 4990-4997.

Christ-Crain, Mirjam, et al. "Effect of procalcitonin-guided treatment on antibiotic use and outcome in lower respiratory tract infections: cluster-randomised, single-blinded intervention trial." *Lancet* 363.9409 (2004): 600-607.

Cristofanilli, Massimo, et al. "Circulating tumor cells, disease progression, and survival in metastatic breast cancer." *New England Journal of Medicine* 351.8 (2004): 781-791.

Davis, Bruce H., et al. "Neutrophil CD64 is an improved indicator of infection or sepsis in emergency department patients." Archives of pathology & laboratory medicine 130.5 (2006): 654-661.

Dieye, Tandakha Ndiaye, et al. "Absolute CD4 T-cell counting in resource-poor settings: direct volumetric measurements versus bead-based clinical flow cytometry instruments." *JAIDS Journal of Acquired Immune Deficiency Syndromes* 39.1 (2005): 32-37.

Divers, S. G., et al. "Quantitation of CD62, soluble CD62, and lysosome-associated membrane proteins 1 and 2 for evaluation of the quality of stored platelet concentrates." *Transfusion* 35.4 (2003): 292-297.

Drexler, Hans G., et al. "Diagnostic value of immunological leukemia phenotyping." *Acta haematologica* 76.1 (1986): 1-8.

Dziegiel, Morten Hanefeld, Leif Kofoed Nielsen, and Adela Berkowicz. "Detecting fetomaternal hemorrhage by flow cytometry." *Current opinion in hematology* 13.6 (2006): 490.

Fischer, Johannes C., et al. "Reducing costs in flow cytometric counting of residual white blood cells in blood products: utilization of a single platform bead free flow rate calibration method." Transfusion 51.7 (2011): 1431-1438.

Graff, Jochen, et al. "Close relationship between the platelet activation marker CD62 and the granular release of platelet-derived growth factor." *Journal of Pharmacology and Experimental Therapeutics* 300.3 (2002): 952-957.

Guerti, K., et al. "Performance evaluation of the PENTRA 60C+ automated hematology analyzer and comparison with the ADVIA 2120." *International journal of laboratory hematology* 31.2 (2009): 132-141.

Hershman, M. J., et al. "Monocyte HLA-DR antigen expression characterizes clinical outcome in the trauma patient." *British Journal of Surgery* 77.2 (2005): 204-207.

Hilfrich, Ralf, and Jalil Hariri. "Prognostic relevance of human papillomavirus L 1 capsid protein detection within mild and moderate dysplastic lesions of the cervix uteri in combination with p16 biomarker." *Analytical and Quantitative Cytology and Histology* 30.2 (2008): 78-82.

Hillier, Sharon L., et al. "A case-control study of chorioamnionic infection and histologic chorioamnionitis in prematurity." *New England Journal of Medicine* 319.15 (1988): 972-978.

Hoffmann, Johannes J M L. "Neutrophil CD64 as a sepsis biomarker." *Biochemia Medica* 21.3 (2011): 282-290.

Kibe, Savitri, Kate Adams, and Gavin Barlow. "Diagnostic and prognostic biomarkers of sepsis in critical care." *Journal of Antimicrobial Chemotherapy* 66.suppl 2 (2011): ii33-ii40.

LaRosa, Steven P., and Steven M. Opal. "Biomarkers: the future." *Critical care clinics* 27.2 (2011): 407.

Liu, N. I. N. G., A. H. Wu, and Shan S. Wong. "Improved quantitative Apt test for detecting fetal hemoglobin in bloody stools of newborns." *Clinical chemistry* 39.11 (1993): 2326-2329.

Lotan, Yair, et al. "Bladder cancer screening in a high risk asymptomatic population using a point of care urine based protein tumor marker." *The Journal of urology* 182.1 (2009): 52-58.

Masse, M., et al. "Validation of a simple method to count very low white cell concentrations in filtered red cells or platelets." *Transfusion* 32.6 (2003): 565-571.

Matic, Goran B., et al. "Whole blood analysis of reticulated platelets: improvements of detection and assay stability." *Cytometry* 34.5 (1998): 229-234.

McDonald, C. P., et al. "Use of a solid-phase fluorescent cytometric technique for the detection of bacteria in platelet concentrates." *Transfusion Medicine* 15.3 (2005): 175-183.

Michelson, Alan D. "Flow cytometry: a clinical test of platelet function." *Open Access Articles* (1996): 290.

Miller, E. M.; Freire, S. L. S.; Wheeler, A. R. "Proteomics in Microfluidic Devices" In *Encyclopedia of Micro-and Nanofluidics*; Li, D. Q., Ed.; Springer: Heidelberg, Germany, 2008; Vol. 3, pp 1749-1758 . . . ."

Moro, Ricardo, et al. "A new broad-spectrum cancer marker." *Vitro Diagnostic Technology* (2005).

Perry, Sara E., et al. "Is low monocyte HLA-DR expression helpful to predict outcome in severe sepsis?." *Intensive care medicine* 29.8 (2003): 1245-1252.

Ramakumar, Sanjay, et al. "Comparison of screening methods in the detection of bladder cancer." *The Journal of urology* 161.2 (1999): 388-394.

Rawstron, Andy C., et al. "Quantitation of minimal disease levels in chronic lymphocytic leukemia using a sensitive flow cytometric assay improves the prediction of outcome and can be used to optimize therapy." *Blood* 98.1 (2001): 29-35.

Rodriguez, William R, et al. "A microchip CD4 counting method for HIV monitoring in resource-poor settings." *PLoS medicine* 2.7 (2005): e182.

Rylatt, D. B., et al. "An immunoassay for human D dimer using monoclonal antibodies." *Thrombosis research* 31.6 (1983): 767-778.

Sacks, David B., et al. "Guidelines and recommendations for laboratory analysis in the diagnosis and management of diabetes mellitus." *Clinical Chemistry* 48.3 (2002): 436-472.

Segal, H. C., et al. "Accuracy of platelet counting haematology analysers in severe thrombocytopenia and potential impact on platelet transfusion." *British Journal of Haematology* 128.4 (2005): 520-525.

Stein, Paul D., et al. "D-dimer for the exclusion of acute venous thrombosis and pulmonary embolism: a systematic review." *Annals of internal medicine* 140.8 (2004): 589.

Sutherland, D. Robert, et al. "The ISHAGE guidelines for CD34+ cell determination by flow cytometry." *Journal of hematotherapy* 5.3 (1996): 213-226.

Wang, Chao, et al. "Reticulated platelets predict platelet count recovery following chemotherapy." *Transfusion* 42.3 (2002): 368-374.

The invention claimed is:

1. A method for determining a biological condition in a subject, the method comprising:
   a) incubating a sample from said subject, in a self-contained stationary cartridge housing at least one composition and at least one reporter functionality, adapted to report a reaction of said at least one composition with said sample, with said at least one composition and with said at least one reporter functionality to report an assay of said reaction;
   b) optically detecting said reaction in a moving fluid comprising,
      1. providing an excitation beam to said cartridge;
      2. measuring a forward scatter measurement from particles in at least one of said sample and said at least composition in an optical reader;
      3. passing a returned beam from said sample via a high-pass filter and a concave grating;
      4. detecting a plurality of at least eight spectrally distinct signals associated with said at least one reporter functionality produced by said concave grating in at least one of photomultiplier array (PMT) and a light-receiving reader unit and scatter channels data;
   c) processing data outputted in said detecting step to determine said assay; and
   d) receiving an indication responsive to said assay, wherein said assay is a flow cytometric assay, thereby providing an indication of the biological condition in said subject, wherein the biological condition is selected from blood diseases, leukemia, thrombocytopenia, immune system disorders, local infections, urinary tract disorders, autoimmune diseases and sepsis;
   wherein said cartridge has a shelf-life of six to twenty four months.

2. A method according to claim 1, wherein said detecting step comprises detecting a signal associated with at least one reporter functionality, said at least one reporter functionality adapted to report a reaction of said at least one composition with said sample, wherein said at least one composition comprises:

i. a cell surface marker;
　　ii. a cell stain;
　　iii. a reagent bound to a solid support;
　　iv. a chemical indicator; and
　　v. a biological cell indicator;
wherein said reagent bound to said solid support is selected from the group consisting of an immobilized enzyme, an immobilized substrate, a plasma protein bead, an antibody bead and an antigen bead.

3. A method according to claim 2, wherein said biological cell indicator is selected from the group consisting of a cell cycle stage indicator, a cell proliferation indicator, a cytokine indicator, a metabolic indicator and an apoptosis indicator.

4. A method according to claim 2, wherein said at least one composition comprises at least two compositions.

5. A method according to claim 4, wherein said at least two compositions comprise at least one of:
　　a. a cell surface marker and a cell element stain;
　　b. a cell surface marker and a plasma protein bead assay;
　　c. a cell surface marker and a solution change marker;
　　d. a cell element stain and a plasma protein bead assay; and
　　e. a cell element stain and a solution change marker.

6. A method according to claim 1, wherein said at least one composition comprises:
　　a) a detection composition comprising at least one of;
　　　　i. at least one target antibody;
　　　　ii. at least one positive control identifying antibody; and
　　　　iii. at least one negative control identifying detection moiety or characteristic; and
　　b) at least one reference composition comprising at least one of;
　　　　i. a target signal reference composition; and
　　　　ii. a reference identifier composition.

7. A method according to claim 1, wherein said at least one composition comprises:
　　a) an antibody composition comprising at least one of;
　　　　ii. at least one target antibody;
　　　　iii. at least one positive control identifying antibody; and
　　　　iv. at least one negative control identifying antibody or characteristic; and
　　b) at least one reference composition comprising at least one of;
　　　　v. a target signal reference composition; and
　　　　vi. a reference identifier composition.

8. A method according to claim 1, wherein said sample comprises at least one of;
　　i. a bodily specimen comprising a target moiety;
　　ii. a positive control moiety; and
　　iii. a negative control moiety.

9. A method according to claim 1, wherein the at least one composition further comprises at least one conditioning moiety comprising;
　　a. at least one lysis reagent; and
　　b. at least one diluent.

10. A method according to claim 1, wherein said providing step further comprises passing said excitation beam via a dichroic mirror through an objective onto a reading channel in said cartridge.

11. A method according to claim 10, further comprising, collecting particle fluorescent emission through said objective, further passing said particle fluorescent emission through said dichroic mirror and reflecting said fluorescent emission from a beamsplitter into a detection path.

* * * * *